(12) United States Patent
Kirsten et al.

(10) Patent No.: US 12,171,709 B2
(45) Date of Patent: Dec. 24, 2024

(54) STIMULATION DEVICE FOR A MALE PENIS

(71) Applicant: NOVOLUTO GmbH, Berlin (DE)

(72) Inventors: Enrico Kirsten, Berlin (DE); Mark Tobias Zegenhagen, Berlin (DE)

(73) Assignee: Novoluto GmbH, Berlin (DE)

( * ) Notice: Subject to any disclaimer, the term of this patent is extended or adjusted under 35 U.S.C. 154(b) by 319 days.

(21) Appl. No.: 16/752,283

(22) Filed: Jan. 24, 2020

(65) Prior Publication Data
US 2020/0237609 A1    Jul. 30, 2020

(30) Foreign Application Priority Data
Jan. 24, 2019 (EP) .................................. 19153494

(51) Int. Cl.
*A61H 19/00* (2006.01)
*A61H 9/00* (2006.01)

(52) U.S. Cl.
CPC ........... *A61H 19/30* (2013.01); *A61H 9/0007* (2013.01); *A61H 9/0057* (2013.01); *A61H 19/32* (2013.01);
(Continued)

(58) Field of Classification Search
CPC .... A61H 19/30; A61H 9/0007; A61H 9/0057; A61H 19/32; A61H 2201/1409;
(Continued)

(56) References Cited

U.S. PATENT DOCUMENTS

| 15,626 A | 8/1856 | Tillotson |
| 787,443 A | 4/1905 | Godman et al. |
(Continued)

FOREIGN PATENT DOCUMENTS

| AU | 2011351297 | 7/2013 |
| AU | 2018200317 | 2/2018 |
(Continued)

OTHER PUBLICATIONS

"Minutes of the Public Hearing in Opposition Proceedings Before the Patent Division 44 of the German Patent and Trademark Office," issued in connection with opposition of German Patent No. 102013110501.7, Apr. 17, 2018, 6 pages (includes English translation).
(Continued)

*Primary Examiner* — Thaddeus B Cox
(74) *Attorney, Agent, or Firm* — Hanley, Flight & Zimmerman, LLC

(57) ABSTRACT

An example stimulation device for a male penis includes a pressure field generation device for generating a pneumatic alternating pressure field, and an applicator for applying the alternating pressure field to a portion of a penis that is to be stimulated. The applicator has a pressure chamber, which can receive an alternating pressure field generated by the pressure field generation device. The pressure chamber has an opening in a contact region of the applicator, so that the alternating pressure field can be applied directly to a portion of the penis that is to be stimulated via the opening. A sealing device is arranged on the applicator, which is configured to seal the pressure chamber against the environment when the applicator is applied to the penis.

21 Claims, 11 Drawing Sheets

(52) U.S. Cl.
CPC ............... *A61H 2201/1409* (2013.01); *A61H 2201/1645* (2013.01)

(58) Field of Classification Search
CPC ... A61H 2201/1645; A61H 9/005; A61F 5/41; A61F 2005/411–418
USPC ......................................................... 600/38
See application file for complete search history.

(56) References Cited

U.S. PATENT DOCUMENTS

| | | | |
|---|---|---|---|
| 809,810 A | 1/1906 | Jost | |
| 847,360 A | 3/1907 | Osius | |
| 907,749 A | 12/1908 | Davenport | |
| 1,042,058 A | 10/1912 | Van Hook | |
| 1,179,129 A | 4/1916 | Maxam | |
| 1,378,922 A | 5/1921 | Ward | |
| 1,502,440 A | 7/1924 | Robert | |
| 1,730,535 A | 10/1929 | Rudolph | |
| 1,732,310 A | 10/1929 | Naibert | |
| 1,762,692 A | 6/1930 | Lair | |
| 1,805,675 A | 5/1931 | Rudolph | |
| 1,882,040 A | 10/1932 | Roehm | |
| 1,898,652 A | 2/1933 | Williams | |
| 1,914,290 A | 6/1933 | Popkin | |
| 1,941,665 A | 1/1934 | De Walt | |
| 1,964,590 A | 6/1934 | Muller | |
| 1,998,696 A | 4/1935 | Andis | |
| 2,017,284 A | 10/1935 | Lembright | |
| 2,052,098 A | 8/1936 | Lockett | |
| 2,064,418 A | 12/1936 | Derringer | |
| 2,076,410 A | 4/1937 | McGerry | |
| 2,112,646 A * | 3/1938 | Biederman | A61H 19/30 601/9 |
| 2,154,427 A | 4/1939 | Andres | |
| 2,189,116 A | 2/1940 | Niemiec | |
| 2,218,081 A | 10/1940 | Brichieri-colombi et al. | |
| 2,218,443 A | 10/1940 | Tweddle | |
| 2,234,102 A | 3/1941 | Andres | |
| 2,314,590 A | 3/1943 | Mccarty | |
| 2,470,660 A | 5/1949 | Snyder | |
| 2,519,790 A | 8/1950 | Quinn | |
| 2,561,034 A | 7/1951 | Phillips | |
| 2,616,417 A | 11/1952 | Holbrook | |
| 2,661,736 A | 12/1953 | Schwartz | |
| 2,674,994 A | 4/1954 | Murphy | |
| 3,396,720 A | 8/1968 | Shigeyuki | |
| 3,818,904 A | 6/1974 | Kawada | |
| 3,841,323 A | 10/1974 | Stoughton | |
| 3,906,940 A | 9/1975 | Kawada | |
| 3,910,262 A | 10/1975 | Stoughton | |
| 4,033,338 A | 7/1977 | Igwebike | |
| 4,088,128 A | 5/1978 | Mabuchi | |
| 4,175,554 A * | 11/1979 | Gerow | A61H 9/0057 600/38 |
| 4,203,431 A | 5/1980 | Abura et al. | |
| 4,312,350 A | 1/1982 | Doan | |
| 4,428,368 A | 1/1984 | Torii | |
| 4,813,403 A | 3/1989 | Endo | |
| 4,900,316 A | 2/1990 | Yamamoto | |
| 5,003,966 A | 4/1991 | Saka et al. | |
| D323,034 S | 1/1992 | Reinstein | |
| D329,563 S | 9/1992 | Rasmussen | |
| 5,336,158 A | 8/1994 | Huggins et al. | |
| D351,236 S | 10/1994 | Held | |
| 5,377,701 A | 1/1995 | Fang | |
| 5,377,702 A | 1/1995 | Sakurai | |
| D359,563 S | 6/1995 | Chi | |
| 5,501,650 A | 3/1996 | Gellert | |
| 5,593,381 A | 1/1997 | Tannenbaum et al. | |
| 5,647,837 A | 7/1997 | McCarty | |
| 5,662,593 A | 9/1997 | Tillman et al. | |
| 5,690,603 A | 11/1997 | Kain | |
| 5,693,002 A | 12/1997 | Tucker et al. | |
| 5,725,473 A | 3/1998 | Taylor | |
| 5,813,973 A | 9/1998 | Gloth | |
| D402,905 S | 12/1998 | Kanza et al. | |
| D414,582 S | 9/1999 | Hwang | |
| D419,893 S | 2/2000 | Cheng | |
| 6,099,463 A | 8/2000 | Hockhalter | |
| 6,183,414 B1 * | 2/2001 | Wysor | G01N 21/49 600/38 |
| D449,690 S | 5/2001 | Hovland et al. | |
| D443,057 S | 10/2001 | Hovland et al. | |
| 6,319,211 B1 | 11/2001 | Ito et al. | |
| D463,862 S | 10/2002 | Lau | |
| 6,464,653 B1 | 10/2002 | Hovland et al. | |
| 6,517,511 B2 | 2/2003 | Yao | |
| D478,385 S | 8/2003 | Dirks et al. | |
| 6,666,875 B1 | 12/2003 | Sakurai et al. | |
| 6,723,060 B2 | 4/2004 | Miller | |
| 6,733,438 B1 | 5/2004 | Dann et al. | |
| 6,758,826 B2 | 7/2004 | Luettgen et al. | |
| D509,301 S | 9/2005 | Talbot et al. | |
| 6,949,067 B1 | 9/2005 | Dann et al. | |
| D510,441 S | 10/2005 | Harris, Jr. et al. | |
| 6,964,643 B2 | 11/2005 | Hovland et al. | |
| D523,561 S | 6/2006 | Telford | |
| D523,562 S | 6/2006 | Telford | |
| D523,963 S | 6/2006 | Telford | |
| 7,079,898 B2 | 7/2006 | Cohn | |
| D545,446 S | 6/2007 | Wu | |
| 7,318,811 B1 | 1/2008 | Corbishley | |
| 7,377,890 B2 | 5/2008 | Liu | |
| 7,431,718 B2 | 10/2008 | Ikadai | |
| 7,530,944 B1 | 5/2009 | Kain | |
| 7,534,203 B2 | 5/2009 | Gil | |
| D609,361 S | 2/2010 | McGarry et al. | |
| D612,510 S | 3/2010 | Byle | |
| 7,682,321 B2 | 3/2010 | Naldoni | |
| D613,417 S | 4/2010 | Imboden et al. | |
| D621,950 S | 8/2010 | Seki et al. | |
| 7,828,717 B2 | 11/2010 | Lee | |
| D637,308 S | 5/2011 | Imboden et al. | |
| D637,309 S | 5/2011 | Park | |
| 7,967,740 B2 | 6/2011 | Mertens et al. | |
| D649,657 S | 11/2011 | Petersen et al. | |
| D652,523 S | 1/2012 | Bradley et al. | |
| 8,100,887 B2 | 1/2012 | Weston et al. | |
| 8,147,399 B2 | 4/2012 | Gloth | |
| D665,091 S | 8/2012 | Mistry et al. | |
| D666,303 S | 8/2012 | Ding et al. | |
| D671,226 S | 11/2012 | Aulwes et al. | |
| 8,382,656 B1 | 2/2013 | Brown | |
| D681,225 S | 4/2013 | Chen | |
| D681,842 S | 5/2013 | Chang | |
| D689,382 S | 9/2013 | Juhng et al. | |
| D692,570 S | 10/2013 | Uzon et al. | |
| 8,556,798 B2 | 10/2013 | Mertens et al. | |
| 8,568,342 B2 | 10/2013 | Shaviv | |
| D693,247 S | 11/2013 | Juhng et al. | |
| 8,579,837 B1 | 11/2013 | Makower et al. | |
| 8,647,255 B2 | 2/2014 | Levy | |
| 8,708,998 B2 | 4/2014 | Weston et al. | |
| D704,345 S | 5/2014 | Tai | |
| D706,440 S | 6/2014 | Hahr et al. | |
| D706,441 S | 6/2014 | Hahr et al. | |
| D706,444 S | 6/2014 | Hahr et al. | |
| D708,440 S | 7/2014 | Owen et al. | |
| 8,784,297 B2 | 7/2014 | Mertens et al. | |
| 8,821,421 B2 | 9/2014 | Imboden et al. | |
| 8,874,215 B2 | 10/2014 | Forsell | |
| 8,876,760 B2 | 11/2014 | Bosman et al. | |
| D723,160 S | 2/2015 | Rodan et al. | |
| D723,707 S | 3/2015 | Matsuura | |
| D723,711 S | 3/2015 | Elliott | |
| 9,022,925 B2 | 5/2015 | Nan | |
| RE45,585 E | 6/2015 | Peddicord | |
| 9,107,797 B2 | 8/2015 | Levy | |
| 9,114,056 B2 | 8/2015 | Imboden et al. | |
| D739,951 S | 9/2015 | Tai | |
| 9,132,058 B2 | 9/2015 | Imboden et al. | |
| D759,256 S | 6/2016 | Chen | |
| D759,261 S | 6/2016 | Son et al. | |

(56) References Cited

U.S. PATENT DOCUMENTS

| | | | |
|---|---|---|---|
| 9,370,656 B2 | 6/2016 | Forsell | |
| RE46,163 E | 9/2016 | Peddicord | |
| D768,309 S | 10/2016 | Hetzel | |
| D768,310 S | 10/2016 | Hetzel | |
| D771,389 S | 11/2016 | Since | |
| D771,828 S | 11/2016 | Sedic | |
| D772,419 S | 11/2016 | Courtion et al. | |
| D773,061 S | 11/2016 | Loebel et al. | |
| D773,065 S | 11/2016 | Driscoll et al. | |
| 9,486,388 B2 | 11/2016 | Wright, Jr. | |
| 9,498,404 B2 | 11/2016 | Murison | |
| D773,823 S | 12/2016 | Wong | |
| D793,571 S | 8/2017 | Iurchenko | |
| D794,854 S | 8/2017 | Zepter | |
| D796,054 S | 8/2017 | Chen | |
| D796,055 S | 8/2017 | Chen | |
| 9,737,457 B2 | 8/2017 | Allen | |
| 9,737,458 B1 | 8/2017 | Olivares et al. | |
| D797,302 S | 9/2017 | Vahlensieck et al. | |
| 9,763,851 B2 | 9/2017 | Lenke | |
| D802,784 S | 11/2017 | Lee | |
| D804,332 S | 12/2017 | Lim et al. | |
| D805,781 S | 12/2017 | Szymanski et al. | |
| 9,849,061 B2 | 12/2017 | Lenke | |
| D809,150 S | 1/2018 | Nolasco et al. | |
| D809,170 S | 1/2018 | Marzynski | |
| 9,855,186 B2 | 1/2018 | Goldenberg et al. | |
| D809,945 S | 2/2018 | Prommel et al. | |
| 9,889,064 B1 | 2/2018 | Olivares et al. | |
| 9,931,271 B2 | 4/2018 | Peter | |
| 9,937,097 B2 | 4/2018 | Lenke | |
| D822,843 S | 7/2018 | Lenke | |
| D825,073 S | 8/2018 | Lenke | |
| 10,085,913 B2 | 10/2018 | Blenk et al. | |
| D846,754 S | 4/2019 | Nelson et al. | |
| 10,342,728 B2 | 7/2019 | Nelson et al. | |
| 10,675,208 B2 | 6/2020 | Nelson et al. | |
| 10,857,063 B2 | 12/2020 | Lenke | |
| 10,973,731 B2 | 4/2021 | Taskinen et al. | |
| 11,039,978 B2 | 6/2021 | Forsell | |
| 11,090,220 B2 | 8/2021 | Lenke | |
| 11,103,418 B2 | 8/2021 | Lenke | |
| 11,484,463 B2 | 11/2022 | Witt | |
| 2001/0041848 A1 | 11/2001 | Ito et al. | |
| 2002/0120219 A1 | 8/2002 | Hovland et al. | |
| 2002/0198488 A1 | 12/2002 | Yao | |
| 2003/0114804 A1 | 6/2003 | Putzer | |
| 2003/0125768 A1* | 7/2003 | Peter | A61F 5/41 607/2 |
| 2003/0176817 A1 | 9/2003 | Chang | |
| 2004/0102822 A1 | 5/2004 | Cohn | |
| 2004/0193079 A1 | 9/2004 | Siddhartha | |
| 2004/0236254 A1 | 11/2004 | Nichols | |
| 2004/0260209 A1 | 12/2004 | Ella et al. | |
| 2004/0260210 A1 | 12/2004 | Ella et al. | |
| 2004/0260212 A1 | 12/2004 | Cho | |
| 2005/0159684 A1 | 7/2005 | Ikadai | |
| 2005/0159760 A1 | 7/2005 | Ikadai et al. | |
| 2005/0203446 A1 | 9/2005 | Takashima | |
| 2005/0256369 A1 | 11/2005 | Gloth | |
| 2006/0089572 A1 | 4/2006 | Byon | |
| 2006/0116612 A1 | 6/2006 | Drysdale | |
| 2006/0229494 A1* | 10/2006 | Wu | A61F 5/41 600/38 |
| 2007/0049792 A1 | 3/2007 | Levy | |
| 2007/0100259 A1 | 5/2007 | Nan | |
| 2007/0185553 A1 | 8/2007 | Kennedy | |
| 2008/0011310 A1* | 1/2008 | Anderson | A61F 2/0054 128/885 |
| 2008/0071138 A1 | 3/2008 | Mertens et al. | |
| 2008/0091060 A1 | 4/2008 | Heilman | |
| 2008/0106896 A1 | 5/2008 | Liu et al. | |
| 2008/0275386 A1 | 11/2008 | Myers | |
| 2008/0304984 A1 | 12/2008 | Chan | |
| 2008/0312674 A1 | 12/2008 | Chen et al. | |
| 2009/0016563 A1 | 1/2009 | Wei et al. | |
| 2009/0038069 A1 | 2/2009 | Heilman | |
| 2009/0048581 A1 | 2/2009 | Sebban | |
| 2009/0069629 A1* | 3/2009 | Uson Calvo | A61H 19/34 600/38 |
| 2009/0099413 A1 | 4/2009 | Kobashikawa et al. | |
| 2009/0118573 A1 | 5/2009 | Tsao | |
| 2009/0275796 A1 | 11/2009 | Gil | |
| 2009/0306577 A1 | 12/2009 | Akridge et al. | |
| 2010/0056963 A1 | 3/2010 | Shaviv | |
| 2010/0298745 A1 | 11/2010 | Liu et al. | |
| 2011/0034837 A1 | 2/2011 | Lee | |
| 2011/0098613 A1 | 4/2011 | Thomas et al. | |
| 2011/0133910 A1 | 6/2011 | Alarcon | |
| 2011/0218395 A1 | 9/2011 | Stout | |
| 2011/0230802 A1 | 9/2011 | Nan | |
| 2011/0288370 A1 | 11/2011 | Orten et al. | |
| 2011/0295162 A1 | 12/2011 | Chang et al. | |
| 2012/0150076 A1 | 6/2012 | Clarvoe | |
| 2012/0330097 A1 | 12/2012 | Lee | |
| 2013/0012769 A1 | 1/2013 | Carlson | |
| 2013/0041295 A1* | 2/2013 | Koenig | A61F 5/41 601/9 |
| 2013/0109913 A1 | 5/2013 | Imboden et al. | |
| 2013/0116503 A1 | 5/2013 | Mertens et al. | |
| 2013/0226050 A1 | 8/2013 | Lee | |
| 2013/0237751 A1 | 9/2013 | Alexander | |
| 2013/0261385 A1 | 10/2013 | Zipper | |
| 2013/0303975 A1* | 11/2013 | Gvodas, Jr. | A61M 35/30 604/23 |
| 2014/0046127 A1 | 2/2014 | Topolovac et al. | |
| 2014/0088351 A1 | 3/2014 | Murison | |
| 2014/0088468 A1 | 3/2014 | Murison | |
| 2014/0088470 A1 | 3/2014 | Topolovac et al. | |
| 2014/0135798 A1 | 5/2014 | David | |
| 2014/0142374 A1 | 5/2014 | Makower et al. | |
| 2014/0179994 A1 | 6/2014 | Topolovac et al. | |
| 2014/0188017 A1 | 7/2014 | Wu | |
| 2014/0194794 A1 | 7/2014 | Sedic | |
| 2014/0228629 A1 | 8/2014 | Baetica et al. | |
| 2014/0236151 A1 | 8/2014 | Lee | |
| 2014/0243590 A1 | 8/2014 | Fang et al. | |
| 2014/0309565 A1 | 10/2014 | Allen | |
| 2014/0350333 A1 | 11/2014 | Stout | |
| 2015/0000678 A1 | 1/2015 | Buckler et al. | |
| 2015/0003644 A1 | 1/2015 | George et al. | |
| 2015/0105609 A1 | 4/2015 | Jochum | |
| 2015/0133832 A1 | 5/2015 | Courtion et al. | |
| 2015/0133833 A1 | 5/2015 | Bradley et al. | |
| 2015/0164678 A1 | 6/2015 | Lee et al. | |
| 2015/0174387 A1 | 6/2015 | McInnes et al. | |
| 2015/0196453 A1 | 7/2015 | Wu | |
| 2015/0196455 A1 | 7/2015 | Mertens et al. | |
| 2015/0257921 A1* | 9/2015 | Sheffy | A61F 5/41 600/38 |
| 2015/0328081 A1 | 11/2015 | Goldenberg et al. | |
| 2015/0351999 A1 | 12/2015 | Brouse | |
| 2015/0366751 A1 | 12/2015 | Stemple | |
| 2016/0000647 A1 | 1/2016 | Eberhardt | |
| 2016/0015595 A1 | 1/2016 | Blenk et al. | |
| 2016/0022533 A1 | 1/2016 | Makower et al. | |
| 2016/0045392 A1 | 2/2016 | Massey et al. | |
| 2016/0058509 A1 | 3/2016 | Van De Wouw et al. | |
| 2016/0058620 A1 | 3/2016 | George et al. | |
| 2016/0074276 A1 | 3/2016 | Scheuring et al. | |
| 2016/0120375 A1 | 5/2016 | Philips | |
| 2016/0120737 A1 | 5/2016 | Sedic | |
| 2016/0128897 A1 | 5/2016 | George et al. | |
| 2016/0136036 A1 | 5/2016 | Cai | |
| 2016/0151236 A1 | 6/2016 | Makower et al. | |
| 2016/0175186 A1 | 6/2016 | Shadduck | |
| 2016/0213557 A1 | 7/2016 | Lenke | |
| 2016/0235621 A1 | 8/2016 | Choe | |
| 2016/0296417 A1 | 10/2016 | Topolovac et al. | |
| 2017/0027809 A1 | 2/2017 | Lenke | |
| 2017/0027810 A1 | 2/2017 | Murison | |
| 2017/0065483 A1 | 3/2017 | Lenke | |
| 2017/0095399 A1 | 4/2017 | Lee | |
| 2017/0100303 A1 | 4/2017 | Kotlov | |

(56) References Cited

U.S. PATENT DOCUMENTS

| | | |
|---|---|---|
| 2017/0135895 A1 | 5/2017 | Jafri |
| 2017/0156971 A1 | 6/2017 | Topolovac et al. |
| 2017/0196801 A1 | 7/2017 | Ghazvini et al. |
| 2017/0202731 A1 | 7/2017 | Goldfarb et al. |
| 2017/0216135 A1 | 8/2017 | Lenke |
| 2017/0281457 A1 | 10/2017 | Witt |
| 2017/0319430 A1 | 11/2017 | Shadduck |
| 2017/0367925 A1 | 12/2017 | Allen |
| 2018/0031089 A1 | 2/2018 | Wong et al. |
| 2018/0031090 A1 | 2/2018 | Wong et al. |
| 2018/0071167 A1 | 3/2018 | Lee |
| 2018/0092799 A1 | 4/2018 | Lenke |
| 2018/0125748 A1 | 5/2018 | Goldenberg et al. |
| 2018/0153764 A1 | 6/2018 | Lenke |
| 2018/0243161 A1 | 8/2018 | Lenke |
| 2018/0243162 A1 | 8/2018 | Lenke |
| 2018/0325769 A1 | 11/2018 | Scheuring et al. |
| 2019/0012884 A1 | 1/2019 | Xu et al. |
| 2019/0015291 A1 | 1/2019 | Sedic |
| 2019/0083354 A1 | 3/2019 | Pahl |
| 2020/0046599 A1 | 2/2020 | Sedic |
| 2020/0069850 A1* | 3/2020 | Beadle .................... A61M 1/90 |
| 2020/0085676 A1 | 3/2020 | Haddock et al. |
| 2020/0093681 A1 | 3/2020 | Haddock et al. |
| 2020/0188221 A1 | 6/2020 | Lenke |
| 2020/0214932 A1 | 7/2020 | Pahl et al. |
| 2020/0281808 A1 | 9/2020 | Kirsten et al. |
| 2020/0330270 A1 | 10/2020 | Foster et al. |
| 2021/0038468 A1 | 2/2021 | Lenke |
| 2021/0038469 A1 | 2/2021 | Zegenhagen et al. |
| 2021/0038470 A1 | 2/2021 | Zegenhagen |
| 2021/0052463 A1 | 2/2021 | Lenke |
| 2021/0128395 A1* | 5/2021 | Witt .................... A61H 9/0057 |
| 2022/0211569 A1 | 7/2022 | Lenke |
| 2022/0211570 A1 | 7/2022 | Zegenhagen |
| 2022/0226186 A1 | 7/2022 | Lenke |

FOREIGN PATENT DOCUMENTS

| | | | | |
|---|---|---|---|---|
| AU | 2014323661 | 3/2018 | | |
| AU | 2015386680 | 3/2018 | | |
| CA | 2923526 | 3/2015 | | |
| CA | 2978495 | 9/2016 | | |
| CA | 2943097 | 10/2017 | | |
| CH | 329193 | 4/1958 | | |
| CN | 2153351 | 1/1994 | | |
| CN | 2157772 | 3/1994 | | |
| CN | 2198900 | 5/1995 | | |
| CN | 2696611 Y | 5/2005 | | |
| CN | 2765609 | 3/2006 | | |
| CN | 1299659 | 2/2007 | | |
| CN | 201067499 | 6/2008 | | |
| CN | 201101685 | 8/2008 | | |
| CN | 201119979 | 9/2008 | | |
| CN | 201139737 | 10/2008 | | |
| CN | 101401739 | 4/2009 | | |
| CN | 101848688 | 9/2010 | | |
| CN | 102151219 | 8/2011 | | |
| CN | 202154785 | 3/2012 | | |
| CN | 102600034 | 7/2012 | | |
| CN | 102743275 | 10/2012 | | |
| CN | 102743276 | 10/2012 | | |
| CN | 202715029 | 2/2013 | | |
| CN | 103070767 A | 5/2013 | | |
| CN | 103517697 | 1/2014 | | |
| CN | 103961246 | 8/2014 | | |
| CN | 104248500 | 12/2014 | | |
| CN | 104284648 | 1/2015 | | |
| CN | 204931954 | 1/2016 | | |
| CN | 105616124 | 6/2016 | | |
| CN | 205494128 | 8/2016 | | |
| CN | 107137218 | 9/2017 | | |
| CN | 108599516 | 9/2018 | | |
| DE | 278733 | 8/1912 | | |
| DE | 538578 | 11/1931 | | |
| DE | 582196 | 8/1933 | | |
| DE | 1463673 | 5/1939 | | |
| DE | 856788 | 11/1952 | | |
| DE | 1703184 | 7/1955 | | |
| DE | 7237890 | 3/1973 | | |
| DE | 3222467 | 12/1983 | | |
| DE | 3515691 A1 | 2/1986 | | |
| DE | 3515691 C2 | 8/1990 | | |
| DE | 9309994 | 10/1993 | | |
| DE | 4243876 | 6/1994 | | |
| DE | 4304091 | 8/1994 | | |
| DE | 4341790 | 6/1995 | | |
| DE | 69108892 | 12/1995 | | |
| DE | 29809041 | 11/1998 | | |
| DE | 29809828 | 11/1998 | | |
| DE | 19853353 | 6/2000 | | |
| DE | 10011289 | 9/2001 | | |
| DE | 20112384 | 10/2001 | | |
| DE | 20106065 | 11/2001 | | |
| DE | 10100795 | 8/2002 | | |
| DE | 10218124 | 11/2003 | | |
| DE | 202005004843 | 7/2005 | | |
| DE | 102004017702 | 10/2005 | | |
| DE | 102006016401 | 8/2007 | | |
| DE | 102005042092 | 10/2007 | | |
| DE | 202007016874 | 2/2008 | | |
| DE | 202007019339 | 1/2012 | | |
| DE | 202012005414 | 6/2012 | | |
| DE | 102012015471 | 2/2014 | | |
| DE | 102013100943 | 7/2014 | | |
| DE | 212013000027 | 8/2014 | | |
| DE | 102013110501 | 3/2015 | | |
| DE | 202015005041 | 10/2015 | | |
| DE | 202015105689 | 11/2015 | | |
| DE | 102016105019 | 7/2017 | | |
| DE | 202016008414 | 11/2017 | | |
| DE | 202016008435 | 12/2017 | | |
| DE | 102017104052 | 8/2018 | | |
| DE | 202017104021 | 10/2018 | | |
| DE | 202019104701 | 11/2019 | | |
| EP | 0251430 | 1/1988 | | |
| EP | 0365230 | 4/1990 | | |
| EP | 472965 | 3/1992 | | |
| EP | 0503027 | 4/1995 | | |
| EP | 1477149 | 11/2004 | | |
| EP | 1554947 | 7/2005 | | |
| EP | 1143909 | 6/2008 | | |
| EP | 2042147 | 4/2009 | | |
| EP | 2645979 | 10/2013 | | |
| EP | 2674142 | 12/2013 | | |
| EP | 2712601 | 4/2014 | | |
| EP | 2777680 | 9/2014 | | |
| EP | 2895135 | 7/2015 | | |
| EP | 3031438 | 6/2016 | | |
| EP | 3153148 | 4/2017 | | |
| EP | 3260106 | 12/2017 | | |
| EP | 3305266 | 4/2018 | | |
| EP | 3357383 | 8/2018 | | |
| EP | 2976057 | 12/2018 | | |
| FR | 2746639 | 10/1997 | | |
| FR | 2746639 A1 * | 10/1997 | ............ | A61H 9/005 |
| GB | 191018973 | 11/1910 | | |
| GB | 1049972 | 11/1966 | | |
| GB | 1060507 | 3/1967 | | |
| GB | 2137097 A * | 10/1984 | ............... | A61F 6/04 |
| JP | S4728781 Y | 8/1972 | | |
| JP | 52-157289 | 11/1977 | | |
| JP | 53135768 | 11/1978 | | |
| JP | 53149442 | 12/1978 | | |
| JP | S547433 Y | 4/1979 | | |
| JP | 54115952 | 9/1979 | | |
| JP | 57099986 | 6/1982 | | |
| JP | H05037234 | 5/1993 | | |
| JP | H6209975 | 8/1994 | | |
| JP | 2555943 | 11/1997 | | |
| JP | 2000197518 | 7/2000 | | |
| JP | 2005288079 | 10/2005 | | |
| JP | 2008125577 | 6/2008 | | |
| JP | 2011-083423 | 4/2011 | | |

(56) References Cited

FOREIGN PATENT DOCUMENTS

| JP | 2011188921 | 9/2011 | | |
|---|---|---|---|---|
| KR | 2000-0002800 | 2/2000 | | |
| KR | 10-2001-0093088 | 10/2001 | | |
| KR | 200439531 | 4/2008 | | |
| KR | 20130068426 A | * 6/2013 | ............... | A61J 9/00 |
| RU | 2014059 | 6/1994 | | |
| RU | 2005134513 | 4/2006 | | |
| TW | 201507719 | 3/2015 | | |
| TW | 201542190 | 11/2015 | | |
| TW | 201603797 | 2/2016 | | |
| WO | WO9205758 | 4/1992 | | |
| WO | 00028939 | 5/2000 | | |
| WO | 2004004610 | 1/2004 | | |
| WO | 2004058134 | 7/2004 | | |
| WO | 2005061042 | 7/2005 | | |
| WO | 2005099366 | 10/2005 | | |
| WO | 2005110331 | 11/2005 | | |
| WO | 2006058291 | 6/2006 | | |
| WO | 2006063461 | 6/2006 | | |
| WO | 2007119034 | 10/2007 | | |
| WO | 2007121107 | 10/2007 | | |
| WO | 2008002625 | 1/2008 | | |
| WO | 2008028076 | 3/2008 | | |
| WO | 2008052151 | 5/2008 | | |
| WO | 2008107902 | 9/2008 | | |
| WO | 2009012172 | 1/2009 | | |
| WO | 2009087627 | 7/2009 | | |
| WO | 2010149168 | 12/2010 | | |
| WO | 2011146948 | 11/2011 | | |
| WO | 2012062256 | 5/2012 | | |
| WO | 2012152297 | 11/2012 | | |
| WO | 2013003954 | 1/2013 | | |
| WO | 2013067367 | 5/2013 | | |
| WO | 2013134388 | 9/2013 | | |
| WO | 2013138658 | 9/2013 | | |
| WO | 2013178223 | 12/2013 | | |
| WO | 2014008606 | 1/2014 | | |
| WO | 2014047718 | 4/2014 | | |
| WO | 2014048884 | 4/2014 | | |
| WO | 2014081600 | 5/2014 | | |
| WO | 2014085736 | 6/2014 | | |
| WO | 2014127531 | 8/2014 | | |
| WO | 2014131110 | 9/2014 | | |
| WO | WO2015039787 | 3/2015 | | |
| WO | 2015060717 | 4/2015 | | |
| WO | 2015070242 | 5/2015 | | |
| WO | 2015096179 | 7/2015 | | |
| WO | 2015101790 | 7/2015 | | |
| WO | 2016146206 | 9/2016 | | |
| WO | 2016162319 A1 | 10/2016 | | |
| WO | 2016172653 | 10/2016 | | |
| WO | 2017141037 | 8/2017 | | |
| WO | 2017158107 | 9/2017 | | |
| WO | 2018065540 | 4/2018 | | |
| WO | 2018154134 | 8/2018 | | |
| WO | WO-2018158250 A1 | * 9/2018 | ....... | A61F 13/00068 |
| WO | 2019158240 | 8/2019 | | |
| WO | 2019192660 | 10/2019 | | |
| WO | 2019192661 | 10/2019 | | |
| WO | 2020056208 | 3/2020 | | |
| WO | 2020056218 | 3/2020 | | |

OTHER PUBLICATIONS

*EIS, Inc. v. Wow Tech International GmbH, et al.*, "First Amended Complaint," filed with the United States District Court for the District of Delaware, case No. 1:19-cv-01227-LPS, Sep. 9, 2019, 40 pages.
*EIS, Inc. v. Wow Tech International GmbH, et al.*, "First Amended Complaint—Exhibits 1-31," filed with the United States District Court for the District of Delaware, case No. 1:19-cv-01227-LPS, Sep. 9, 2019, 527 pages.
"Petition for Inter Partes Review of U.S. Pat. No. 9,849,061," filed with the United States Patent and Trademark Office on Oct. 2, 2019, 97 pages.
"Petition for Inter Partes Review of U.S. Pat. No. 9,849,061," Exhibit 1001, filed with the United States Patent and Trademark Office on Oct. 2, 2019, 18 pages.
"Petition for Inter Partes Review of U.S. Pat. No. 9,849,061," Exhibit 1002, filed with the United States Patent and Trademark Office on Oct. 2, 2019, 137 pages. (Uploaded in 5 parts).
"Petition for Inter Partes Review of U.S. Pat. No. 9,849,061," Exhibit 1003, filed with the United States Patent and Trademark Office on Oct. 2, 2019, 1,367 pages. (Uploaded in 5 parts).
"Petition for Inter Partes Review of U.S. Pat. No. 9,849,061," Exhibit 1004, filed with the United States Patent and Trademark Office on Oct. 2, 2019, 9 pages.
"Petition for Inter Partes Review of U.S. Pat. No. 9,849,061," Exhibit 1006, filed with the United States Patent and Trademark Office on Oct. 2, 2019, 34 pages.
"Petition for Inter Partes Review of U.S. Pat. No. 9,849,061," Exhibit 1007, filed with the United States Patent and Trademark Office on Oct. 2, 2019, 22 pages.
"Petition for Inter Partes Review of U.S. Pat. No. 9,849,061," Exhibit 1008, filed with the United States Patent and Trademark Office on Oct. 2, 2019, 40 pages.
"Petition for Inter Partes Review of U.S. Pat. No. 9,849,061," Exhibit 1010, filed with the United States Patent and Trademark Office on Oct. 2, 2019, 5 pages.
"Petition for Inter Partes Review of U.S. Pat. No. 9,849,061," Exhibit 1011, filed with the United States Patent and Trademark Office on Oct. 2, 2019, 17 pages.
"Petition for Inter Partes Review of U.S. Pat. No. 9,849,061," Exhibit 1012, filed with the United States Patent and Trademark Office on Oct. 2, 2019, 61 pages.
"Petition for Inter Partes Review of U.S. Pat. No. 9,849,061," Exhibit 1013, filed with the United States Patent and Trademark Office on Oct. 2, 2019, 46 pages.
"Notification of an Opposition," issued by the European Patent Office in connection with European Patent No. EP2976057 on Sep. 12, 2019, opposition filed by EIS GmbH, 132 pages (includes English translation).
"Notification of an Opposition," issued by the European Patent Office in connection with European Patent No. EP2976057 on Sep. 10, 2019, opposition filed by Fun Factory Ltd., 117 pages (includes English translation).
"Notification of an Opposition," issued by the European Patent Office in connection with European Patent No. EP2976057 on Sep. 12, 2019, opposition filed by Hu Xiaorong, 35 pages (includes English translation).
"Opposition to a European Patent," filed with the European Patent Office by EIS GmbH in connection with European Patent No. EP3308762 on Sep. 11, 2019, 95 pages (includes English translation).
"Opposition to a European Patent," filed with the European Patent Office by Fun Factory Ltd. in connection with European Patent No. EP3308762 on Sep. 11, 2019, 124 pages (includes English translation).
IP Australia, "Examination Report," issued in connection with Australian Application No. 2018222907 on Sep. 3, 2019, 4 pages.
IP Australia, "Examination Report," issued in connection with Australian Application No. 2019201070 on Jul. 9, 2019, 4 pages.
Korean Patent Office, "Office Action," issued in connection with Korean Application No. 10-2017-0129112 on Aug. 29, 2019, 9 pages (includes English summary of Office action).
Korean Patent Office, "Office Action," issued in connection with Korean Application No. 10-2017-7028845 on Sep. 18, 2019, 7 pages (includes English summary of Office action).
European Patent Office, "Notice of Submission of Third Party Observation," issued in connection with European Application No. EP17202394.7 on Jul. 9, 2019, 5 pages (submission in English).
"Opposition Document," filed in connection with opposition of German Patent No. 102013110501.7 on Jan. 24, 2018, 69 pages (includes English translation).
*EIS, Inc. v. Wow Tech International GmbH, et al.*, "Defendants' Consolidated Motion to Dismiss EIS, Inc.'s Complaint Pursuant to

(56) References Cited

OTHER PUBLICATIONS

Federal Rules Of Civil Procedure 12(B)(2) and 12(b)(6)," filed with the United States District Court for the District of Delaware in connection with Case No. 1:19-cv-1277-LPS on Oct. 2, 2019, 3 pages.
United States Patent and Trademark Office, "Corrected Notice of Allowability," issued in connection with U.S. Appl. No. 15/354,599 on Nov. 12, 2019, 2 pages.
German Patent and Trademark Office, "English Translation of Invitation to Speak," issued in connection with opposition of German Patent No. 102013110501.7 on Nov. 17, 2016, 20 pages.
"English Translation of Patentee Submission," filed with the German Patent and Trademark Office in connection with opposition of German Patent No. 102013110501.7 on Sep. 18, 2017, 38 pages.
"English Translation of Submission of Opponent," filed with the German Patent and Trademark Office in connection with opposition of German Patent No. 102013110501.7 on Oct. 5, 2017, 6 pages.
"English Translation of Submission of Opponent," filed with the German Patent and Trademark Office in connection with opposition of German Patent No. 102013110501.7 on Nov. 13, 2017, 8 pages.
German Patent and Trademark Office, "English Translation of Summons to Attend Oral Proceedings," issued in connection with opposition of German Patent No. 102013110501.7 on Nov. 28, 2017, 3 pages.
"English Translation of Patentee Submission," filed with the German Patent and Trademark Office in connection with opposition of German Patent No. 102013110501.7 on Jan. 30, 2018, 5 pages.
German Patent and Trademark Office, "English Translation of Additions to Summons," issued in connection with opposition of German Patent No. 102013110501.7 on Nov. 24, 2017, 1 page.
German Patent and Trademark Office, "English Translation of Summons to Attend Oral Proceedings," issued in connection with opposition of German Patent No. 102013110501.7 on Feb. 2, 2018, 3 pages.
"English Translation of Opponent Submission," filed with the German Patent and Trademark Office in connection with opposition of German Patent No. 102013110501.7 on Mar. 14, 2018, 5 pages.
"English Translation of Patentee Submission," filed with the German Patent and Trademark Office in connection with opposition of German Patent No. 102013110501.7 on Apr. 3, 2018, 2 pages.
"English Translation of Patentee Submission," filed with the German Patent and Trademark Office, in connection with opposition of German Patent No. 102013110501.7 on Apr. 12, 2018, 45 pages.
"English Translation of Auxiliary Request 1," filed with the German Patent and Trademark Office in connection with opposition of German Patent No. 2013110501.7 on Apr. 16, 2018, 5 pages.
"English Translation of Auxiliary Request 2," filed with the German Patent and Trademark Office in connection with opposition of German Patent No. 2013110501.7 on Apr. 16, 2018, 6 pages.
"English Translation of Auxiliary Request 3," filed with the German Patent and Trademark Office in connection with opposition of German Patent No. 2013110501.7 on Apr. 16, 2018, 5 pages.
*Novoluto GmbH* v. *EIS GmbH*, "Judgment," issued by the German Court in connection with German litigation proceeding on Dec. 14, 2017, 71 pages (includes English translation).
*Novoluto GmbH* v. *EIS GmbH*, "Transcript," filed with the German Court in connection German litigation proceeding on Jul. 20, 2017, 44 pages (includes English translation).
*Novoluto GmbH* v. *EIS GmbH*, "Complaint," filed the German Court in connection German litigation proceeding on Aug. 5, 2016, 75 pages (includes English translation).
United States Patent and Trademark Office, "Notice of Filing Date Accorded to Petition and Time for Filing Patent Owner Preliminary Response," issued in connection with Case IPR2019-01302 on Jul. 18, 2019, 5 pages.
"Patent Owner's Amended Mandatory Notices Pursuant to 37 C.F.R. 42.8," filed with the United States Patent and Trademark Office in connection with Case IPR2019-01302 on Sep. 3, 2019, 6 pages.
"Patent Owner's Amended Mandatory Notices Pursuant to 37 C.F.R. 42.8," filed with the United States Patent and Trademark Office in connection with Case IPR2019-01302 on Sep. 30, 2019, 6 pages.
"Patent Owner's Amended Mandatory Notices Pursuant to 37 C.F.R. 42.8," filed with the United States Patent and Trademark Office in connection with Case IPR2019-01302 on Oct. 18, 2019, 6 pages.
"Patent Owner's Mandatory Notices," filed with the United States Patent and Trademark Office in connection with Case IPR2019-01302 on Jul. 24, 2019, 4 pages.
"Patent Owner's Updated Mandatory Notices," filed with the United States Patent and Trademark Office in connection with Case IPR2019-01302 on Aug. 21, 2019, 4 pages.
"Petitioner's Amended Mandatory Notices Pursuant To 37 C.F.R. 42.8," filed with the United States Patent and Trademark Office in connection with Case IPR2019-01302 on Oct. 8, 2019, 5 pages.
"Patent Owner's Preliminary Response Pursuant To 37 C.F.R. § 42.107," filed with the United States Patent and Trademark Office in connection with Case IPR2019-01302 on Oct. 18, 2019, 85 pages.
"Patent Owner's Preliminary Response Pursuant to 37 C.F.R. § 42.107," Exhibit 2001, filed with the United States Patent and Trademark Office in connection with Case IPR2019-01302 on Oct. 18, 2019, 80 pages.
"Patent Owner's Preliminary Response Pursuant to 37 C.F.R. § 42.107," Exhibit 2002, filed with the United States Patent and Trademark Office in connection with Case IPR2019-01302 on Oct. 18, 2019, 30 pages.
"Patent Owner's Preliminary Response Pursuant to 37 C.F.R. § 42.107," Exhibit 2003, filed with the United States Patent and Trademark Office in connection with Case IPR2019-01302 on Oct. 18, 2019, 18 pages.
"Patent Owner's Preliminary Response Pursuant to 37 C.F.R. § 42.107," Exhibit 2004, filed with the United States Patent and Trademark Office in connection with Case IPR2019-01302 on Oct. 18, 2019, 47 pages.
"Patent Owner's Preliminary Response Pursuant to 37 C.F.R. § 42.107," Exhibit 2005, filed with the United States Patent and Trademark Office in connection with Case IPR2019-01302 on Oct. 18, 2019, 60 pages.
"Patent Owner's Preliminary Response Pursuant to 37 C.F.R. § 42.107," Exhibit 2006, filed with the United States Patent and Trademark Office in connection with Case IPR2019-01302 on Oct. 18, 2019, 19 pages.
"Patent Owner's Preliminary Response Pursuant to 37 C.F.R. § 42.107," Exhibit 2007, filed with the United States Patent and Trademark Office in connection with Case IPR2019-01302 on Oct. 18, 2019, 16 pages.
"Patent Owner's Preliminary Response Pursuant to 37 C.F.R. § 42.107," Exhibit 2008, filed with the United States Patent and Trademark Office in connection with Case IPR2019-01302 on Oct. 18, 2019, 10 pages.
"Patent Owner's Preliminary Response Pursuant to 37 C.F.R. § 42.107," Exhibit 2009, filed with the United States Patent and Trademark Office in connection with Case IPR2019-01302 on Oct. 18, 2019, 12 pages.
"Patent Owner's Preliminary Response Pursuant to 37 C.F.R. § 42.107," Exhibit 2010, filed with the United States Patent and Trademark Office in connection with Case IPR2019-01302 on Oct. 18, 2019, 9 pages.
"Patent Owner's Preliminary Response Pursuant to 37 C.F.R. § 42.107," Exhibit 2011, filed with the United States Patent and Trademark Office in connection with Case IPR2019-01302 on Oct. 18, 2019, 2 pages.
"Patent Owner's Preliminary Response Pursuant to 37 C.F.R. § 42.107," Exhibit 2012, filed with the United States Patent and Trademark Office in connection with Case IPR2019-01302 on Oct. 18, 2019, 7 pages.
"Patent Owner's Preliminary Response Pursuant to 37 C.F.R. § 42.107," Exhibit 2013, filed with the United States Patent and Trademark Office in connection with Case IPR2019-01302 on Oct. 18, 2019, 4 pages.

(56) References Cited

OTHER PUBLICATIONS

"Patent Owner's Preliminary Response Pursuant to 37 C.F.R. § 42.107," Exhibit 2014, filed with the United States Patent and Trademark Office in connection with Case IPR2019-01302 on Oct. 18, 2019, 77 pages.
"Patent Owner's Preliminary Response Pursuant to 37 C.F.R. § 42.107," Exhibit 2015, filed with the United States Patent and Trademark Office in connection with Case IPR2019-01302 on Oct. 18, 2019, 76 pages.
"Patent Owner's Preliminary Response Pursuant to 37 C.F.R. § 42.107," Exhibit 2016, filed with the United States Patent and Trademark Office in connection with Case IPR2019-01302 on Oct. 18, 2019, 169 pages.
"Patent Owner's Preliminary Response Pursuant to 37 C.F.R. § 42.107," Exhibit 2017, filed with the United States Patent and Trademark Office in connection with Case IPR2019-01302 on Oct. 18, 2019, 40 pages.
"Patent Owner's Preliminary Response Pursuant to 37 C.F.R. § 42.107," Exhibit 2018, filed with the United States Patent and Trademark Office in connection with Case IPR2019-01302 on Oct. 18, 2019, 15 pages.
"Patent Owner's Preliminary Response Pursuant to 37 C.F.R. § 42.107," Exhibit 2019, filed with the United States Patent and Trademark Office in connection with Case IPR2019-01302 on Oct. 18, 2019, 8 pages.
"Patent Owner's Preliminary Response Pursuant to 37 C.F.R. § 42.107," Exhibit 2020, filed with the United States Patent and Trademark Office in connection with Case IPR2019-01302 on Oct. 18, 2019, 11 pages.
"Patent Owner's Preliminary Response Pursuant to 37 C.F.R. § 42.107," Exhibit 2021, filed with the United States Patent and Trademark Office in connection with Case IPR2019-01302 on Oct. 18, 2019, 25 pages.
"Patent Owner's Preliminary Response Pursuant to 37 C.F.R. § 42.107," Exhibit 2022, filed with the United States Patent and Trademark Office in connection with Case IPR2019-01302 on Oct. 18, 2019, 97 pages.
"Patent Owner's Preliminary Response Pursuant to 37 C.F.R. § 42.107," Exhibit 2023, filed with the United States Patent and Trademark Office in connection with Case IPR2019-01302 on Oct. 18, 2019, 4 pages.
"Patent Owner's Preliminary Response Pursuant to 37 C.F.R. § 42.107," Exhibit 2024, filed with the United States Patent and Trademark Office in connection with Case IPR2019-01302 on Oct. 18, 2019, 7 pages.
"Patent Owner's Preliminary Response Pursuant to 37 C.F.R. § 42.107," Exhibit 2025, filed with the United States Patent and Trademark Office in connection with Case IPR2019-01302 on Oct. 18, 2019, 1 page.
United States Patent and Trademark Office, "Notice of Filing Date Accorded to Petition and Time for Filing Patent Owner Preliminary Response," issued in connection with Case IPR2019-01444 on Aug. 14, 2019, 6 pages.
"Patent Owner's Amended Mandatory Notices Pursuant to 37 C.F.R. 42.8," filed with the United States Patent and Trademark Office in connection with case IPR2019-01444 on Aug. 26, 2019, 6 pages.
"Patent Owner's Amended Mandatory Notices Pursuant to 37 C.F.R. 42.8," filed with the United States Patent and Trademark Office in connection with case IPR2019-01444 on Sep. 30, 2019, 6 pages.
"Patent Owner's Amended Mandatory Notices Pursuant to 37 C.F.R. 42.8," filed with the United States Patent and Trademark Office in connection with case IPR2019-01444 on Oct. 23, 2019, 6 pages.
"Patent Owner's Mandatory Notices," filed with the United States Patent and Trademark Office in connection with case IPR2019-01444 on Aug. 21, 2019, 5 pages.
"Petitioner's Amended Mandatory Notices," filed with the United States Patent and Trademark Office in connection with case IPR2019-01444 on Oct. 8, 2019, 5 pages.
"Patent Owner's Preliminary Response Pursuant to 37 C.F.R. § 42.107," filed with the United States Patent and Trademark Office in connection with case IPR2019-01444 on Nov. 14, 2019, 88 pages.
"Patent Owner's Preliminary Response Pursuant to 37 C.F.R. § 42.107," Exhibit 2001, filed with the United States Patent and Trademark Office in connection with Case IPR2019-01444 on Nov. 14, 2019, 81 pages.
"Patent Owner's Preliminary Response Pursuant to 37 C.F.R. § 42.107," Exhibit 2002, filed with the United States Patent and Trademark Office in connection with Case IPR2019-01444 on Nov. 14, 2019, 36 pages.
"Patent Owner's Preliminary Response Pursuant to 37 C.F.R. § 42.107," Exhibit 2003, filed with the United States Patent and Trademark Office in connection with Case IPR2019-01444 on Nov. 14, 2019, 18 pages.
"Patent Owner's Preliminary Response Pursuant to 37 C.F.R. § 42.107," Exhibit 2004, filed with the United States Patent and Trademark Office in connection with Case IPR2019-01444 on Nov. 14, 2019, 97 pages.
"Patent Owner's Preliminary Response Pursuant to 37 C.F.R. § 42.107," Exhibit 2005, filed with the United States Patent and Trademark Office in connection with Case IPR2019-01444 on Nov. 14, 2019, 61 pages.
"Patent Owner's Preliminary Response Pursuant to 37 C.F.R. § 42.107," Exhibit 2006, filed with the United States Patent and Trademark Office in connection with Case IPR2019-01444 on Nov. 14, 2019, 60 pages.
"Patent Owner's Preliminary Response Pursuant to 37 C.F.R. § 42.107," Exhibit 2007, filed with the United States Patent and Trademark Office in connection with Case IPR2019-01444 on Nov. 14, 2019, 22 pages.
"Patent Owner's Preliminary Response Pursuant to 37 C.F.R. § 42.107," Exhibit 2008, filed with the United States Patent and Trademark Office in connection with Case IPR2019-01444 on Nov. 14, 2019, 12 pages.
"Patent Owner's Preliminary Response Pursuant to 37 C.F.R. § 42.107," Exhibit 2009, filed with the United States Patent and Trademark Office in connection with Case IPR2019-01444 on Nov. 14, 2019, 7 pages.
"Patent Owner's Preliminary Response Pursuant to 37 C.F.R. § 42.107," Exhibit 2010, filed with the United States Patent and Trademark Office in connection with Case IPR2019-01444 on Nov. 14, 2019, 16 pages.
"Patent Owner's Preliminary Response Pursuant to 37 C.F.R. § 42.107," Exhibit 2011, filed with the United States Patent and Trademark Office in connection with Case IPR2019-01444 on Nov. 14, 2019, 10 pages.
"Patent Owner's Preliminary Response Pursuant to 37 C.F.R. § 42.107," Exhibit 2012, filed with the United States Patent and Trademark Office in connection with Case IPR2019-01444 on Nov. 14, 2019, 12 pages.
"Patent Owner's Preliminary Response Pursuant to 37 C.F.R. § 42.107," Exhibit 2013, filed with the United States Patent and Trademark Office in connection with Case IPR2019-01444 on Nov. 14, 2019, 9 pages.
"Patent Owner's Preliminary Response Pursuant to 37 C.F.R. § 42.107," Exhibit 2014, filed with the United States Patent and Trademark Office in connection with Case IPR2019-01444 on Nov. 14, 2019, 2 pages.
"Patent Owner's Preliminary Response Pursuant to 37 C.F.R. § 42.107," Exhibit 2015, filed with the United States Patent and Trademark Office in connection with Case IPR2019-01444 on Nov. 14, 2019, 4 pages.
"Patent Owner's Preliminary Response Pursuant to 37 C.F.R. § 42.107," Exhibit 2016, filed with the United States Patent and Trademark Office in connection with Case IPR2019-01444 on Nov. 14, 2019, 172 pages.

(56) References Cited

OTHER PUBLICATIONS

"Patent Owner's Preliminary Response Pursuant to 37 C.F.R. § 42.107," Exhibit 2017, filed with the United States Patent and Trademark Office in connection with Case IPR2019-01444 on Nov. 14, 2019, 40 pages.
"Patent Owner's Preliminary Response Pursuant to 37 C.F.R. § 42.107," Exhibit 2018, filed with the United States Patent and Trademark Office in connection with Case IPR2019-01444 on Nov. 14, 2019, 153 pages.
"Patent Owner's Preliminary Response Pursuant to 37 C.F.R. § 42.107," Exhibit 2019, filed with the United States Patent and Trademark Office in connection with Case IPR2019-01444 on Nov. 14, 2019, 4 pages.
"Patent Owner's Preliminary Response Pursuant to 37 C.F.R. § 42.107," Exhibit 2020, filed with the United States Patent and Trademark Office in connection with Case IPR2019-01444 on Nov. 14, 2019, 3 pages.
"Patent Owner's Preliminary Response Pursuant to 37 C.F.R. § 42.107," Exhibit 2021, filed with the United States Patent and Trademark Office in connection with Case IPR2019-01444 on Nov. 14, 2019, 7 pages.
"Patent Owner's Preliminary Response Pursuant to 37 C.F.R. § 42.107," Exhibit 2022, filed with the United States Patent and Trademark Office in connection with Case IPR2019-01444 on Nov. 14, 2019, 11 pages.
"Patent Owner's Preliminary Response Pursuant to 37 C.F.R. § 42.107," Exhibit 2023, filed with the United States Patent and Trademark Office in connection with Case IPR2019-01444 on Nov. 14, 2019, 8 pages.
"Patent Owner's Preliminary Response Pursuant to 37 C.F.R. § 42.107," Exhibit 2024, filed with the United States Patent and Trademark Office in connection with Case IPR2019-01444 on Nov. 14, 2019, 20 pages.
"Patent Owner's Preliminary Response Pursuant to 37 C.F.R. § 42.107," Exhibit 2025, filed with the United States Patent and Trademark Office in connection with Case IPR2019-01444 on Nov. 14, 2019, 3 pages.
"Patent Owner's Preliminary Response Pursuant to 37 C.F.R. § 42.107," Exhibit 2026, filed with the United States Patent and Trademark Office in connection with Case IPR2019-01444 on Nov. 14, 2019, 9 pages.
"Patent Owner's Preliminary Response Pursuant to 37 C.F.R. § 42.107," Exhibit 2027, filed with the United States Patent and Trademark Office in connection with Case IPR2019-01444 on Nov. 14, 2019, 4 pages.
"Patent Owner's Preliminary Response Pursuant to 37 C.F.R. § 42.107," Exhibit 2028, filed with the United States Patent and Trademark Office in connection with Case IPR2019-01444 on Nov. 14, 2019, 7 pages.
"Patent Owner's Preliminary Response Pursuant to 37 C.F.R. § 42.107," Exhibit 2029, filed with the United States Patent and Trademark Office in connection with Case IPR2019-01444 on Nov. 14, 2019, 3 pages.
"Patent Owner's Preliminary Response Pursuant to 37 C.F.R. § 42.107," Exhibit 2030, filed with the United States Patent and Trademark Office in connection with Case IPR2019-01444 on Nov. 14, 2019, 4 pages.
"Patent Owner's Preliminary Response Pursuant to 37 C.F.R. § 42.107," Exhibit 2031, filed with the United States Patent and Trademark Office in connection with Case IPR2019-01444 on Nov. 14, 2019, 7 pages.
"Patent Owner's Preliminary Response Pursuant to 37 C.F.R. § 42.107," Exhibit 2032, filed with the United States Patent and Trademark Office in connection with Case IPR2019-01444 on Nov. 14, 2019, 4 pages.
"Patent Owner's Preliminary Response Pursuant to 37 C.F.R. § 42.107," Exhibit 2033, filed with the United States Patent and Trademark Office in connection with Case IPR2019-01444 on Nov. 14, 2019, 25 pages.
"Patent Owner's Preliminary Response Pursuant to 37 C.F.R. § 42.107," Exhibit 2034, filed with the United States Patent and Trademark Office in connection with Case IPR2019-01444 on Nov. 14, 2019, 3 pages.
United States Patent and Trademark Office, "Notice of Filing Date Accorded to Petition and Time for Filing Patent Owner Preliminary Response," issued in connection with Case IPR2020-00007 on Oct. 8, 2019, 5 pages.
"Patent Owner's Amended Mandatory Notices Pursuant to 37 C.F.R. 42.8," filed with the United States Patent and Trademark Office in connection with case IPR2020-00007 on Oct. 23, 2019, 6 pages.
*EIS, Inc.* v. *Wow Tech International GmbH*, "Declaration of Frank Ferrari in Support of Defendants, Wow Tech International GmbH, Wow Tech Canada Ltd., and Novoluto GmbH's Consolidated Motion to Dismiss," filed with the United States District Court for the District of Delaware in connection with Case No. 1:19-cv-1277-LPS on Oct. 2, 2019, 3 pages.
*EIS, Inc.* v. *Wow Tech International GmbH*, "Declaration of Florian Holst in Support of Defendants, Wow Tech International GmbH, Wow Tech Canada Ltd., and Novoluto GmbH's Consolidated Motion to Dismiss," filed with the United States District Court for the District of Delaware in connection with Case No. 1:19-cv-1277-LPS on Oct. 2, 2019, 3 pages.
*EIS, Inc.* v. *Wow Tech International GmbH*, "Declaration Of Johannes Plettenberg in Support of Defendants, Wow Tech International GmbH, Wow Tech Canada Ltd., and Novoluto GmbH's Consolidated Motion to Dismiss," filed with the United States District Court for the District of Delaware in connection with Case No. 1:19-cv-1277-LPS on Oct. 2, 2019, 3 pages.
*EIS, Inc.* v. *Wow Tech International GmbH*, "Defendants' Opening Brief in Support of their Consolidated Motion to Dismiss Pursuant to Federal Rules of Civil Procedure 12(B)(2) and 12(B)(6)," filed with the United States District Court for the District of Delaware in connection with Case No. 1:19-cv-1277-LPS on Oct. 2, 2019, 42 pages.
The International Bureau of WIPO, "English Translation of International Report on Patentability," issued in connection with application No. PCT/EP2017/075400, on Apr. 9, 2019, 12 pages.
Israel Patent Office, "Office Action," issued in connection with Israeli Patent Application No. 254607, on Dec. 1, 2019, 6 pages (includes English translation).
Canadian Patent Office, "Office Action," issued in connection with Canadian Patent Application No. 3,051,672, on Oct. 3, 2019, 7 pages.
United States Patent and Trademark Office, "Notice of Allowance," issued in connection with U.S. Appl. No. 15/354,599, on Dec. 16, 2019, 21 pages.
"Patent Owner's Preliminary Response Pursuant to 37 C.F.R. § 42.107," filed with the United States Patent and Trademark Office in connection with case IPR2020-00007 on Jan. 8, 2020, 87 pages.
"Patent Owner's Preliminary Response Pursuant to 37 C.F.R. § 42.107," Exhibit 2001, filed with the United States Patent and Trademark Office in connection with Case IPR2020-00007 on Jan. 8, 2020, 72 pages.
"Patent Owner's Preliminary Response Pursuant to 37 C.F.R. § 42.107," Exhibit 2002, filed with the United States Patent and Trademark Office in connection with Case IPR2020-00007 on Jan. 8, 2020, 36 pages.
"Patent Owner's Preliminary Response Pursuant to 37 C.F.R. § 42.107," Exhibit 2003, filed with the United States Patent and Trademark Office in connection with Case IPR2020-00007 on Jan. 8, 2020, 3 pages.
"Patent Owner's Preliminary Response Pursuant to 37 C.F.R. § 42.107," Exhibit 2004, filed with the United States Patent and Trademark Office in connection with Case IPR2020-00007 on Jan. 8, 2020, 62 pages.
"Patent Owner's Preliminary Response Pursuant to 37 C.F.R. § 42.107," Exhibit 2005, filed with the United States Patent and Trademark Office in connection with Case IPR2020-00007 on Jan. 8, 2020, 60 pages.

(56) References Cited

OTHER PUBLICATIONS

"Patent Owner's Preliminary Response Pursuant to 37 C.F.R. § 42.107," Exhibit 2006, filed with the United States Patent and Trademark Office in connection with Case IPR2020-00007 on Jan. 8, 2020, 4 pages.
"Patent Owner's Preliminary Response Pursuant to 37 C.F.R. § 42.107," Exhibit 2007, filed with the United States Patent and Trademark Office in connection with Case IPR2020-00007 on Jan. 8, 2020, 5 pages.
"Patent Owner's Preliminary Response Pursuant to 37 C.F.R. § 42.107," Exhibit 2008, filed with the United States Patent and Trademark Office in connection with Case IPR2020-00007 on Jan. 8, 2020, 10 pages.
"Patent Owner's Preliminary Response Pursuant to 37 C.F.R. § 42.107," Exhibit 2009, filed with the United States Patent and Trademark Office in connection with Case IPR2020-00007 on Jan. 8, 2020, 4 pages.
"Patent Owner's Preliminary Response Pursuant to 37 C.F.R. § 42.107," Exhibit 2010, filed with the United States Patent and Trademark Office in connection with Case IPR2020-00007 on Jan. 8, 2020, 14 pages.
"Patent Owner's Preliminary Response Pursuant to 37 C.F.R. § 42.107," Exhibit 2011, filed with the United States Patent and Trademark Office in connection with Case IPR2020-00007 on Jan. 8, 2020, 16 pages.
"Patent Owner's Preliminary Response Pursuant to 37 C.F.R. § 42.107," Exhibit 2012, filed with the United States Patent and Trademark Office in connection with Case IPR2020-00007 on Jan. 8, 2020, 12 pages.
"Patent Owner's Preliminary Response Pursuant to 37 C.F.R. § 42.107," Exhibit 2013, filed with the United States Patent and Trademark Office in connection with Case IPR2020-00007 on Jan. 8, 2020, 9 pages.
"Patent Owner's Preliminary Response Pursuant to 37 C.F.R. § 42.107," Exhibit 2014, filed with the United States Patent and Trademark Office in connection with Case IPR2020-00007 on Jan. 8, 2020, 2 pages.
"Patent Owner's Preliminary Response Pursuant to 37 C.F.R. § 42.107," Exhibit 2015, filed with the United States Patent and Trademark Office in connection with Case IPR2020-00007 on Jan. 8, 2020, 7 pages.
"Patent Owner's Preliminary Response Pursuant to 37 C.F.R. § 42.107," Exhibit 2016, filed with the United States Patent and Trademark Office in connection with Case IPR2020-00007 on Jan. 8, 2020, 4 pages.
"Patent Owner's Preliminary Response Pursuant to 37 C.F.R. § 42.107," Exhibit 2017, filed with the United States Patent and Trademark Office in connection with Case IPR2020-00007 on Jan. 8, 2020, 77 pages.
"Patent Owner's Preliminary Response Pursuant to 37 C.F.R. § 42.107," Exhibit 2018, filed with the United States Patent and Trademark Office in connection with Case IPR2020-00007 on Jan. 8, 2020, 76 pages.
"Patent Owner's Preliminary Response Pursuant to 37 C.F.R. § 42.107," Exhibit 2019, filed with the United States Patent and Trademark Office in connection with Case IPR2020-00007 on Jan. 8, 2020, 169 pages.
"Patent Owner's Preliminary Response Pursuant to 37 C.F.R. § 42.107," Exhibit 2020, filed with the United States Patent and Trademark Office in connection with Case IPR2020-00007 on Jan. 8, 2020, 40 pages.
"Patent Owner's Preliminary Response Pursuant to 37 C.F.R. § 42.107," Exhibit 2021, filed with the United States Patent and Trademark Office in connection with Case IPR2020-00007 on Jan. 8, 2020, 7 pages.
"Patent Owner's Preliminary Response Pursuant to 37 C.F.R. § 42.107," Exhibit 2022, filed with the United States Patent and Trademark Office in connection with Case IPR2020-00007 on Jan. 8, 2020, 6 pages.
"Patent Owner's Preliminary Response Pursuant to 37 C.F.R. § 42.107," Exhibit 2023, filed with the United States Patent and Trademark Office in connection with Case IPR2020-00007 on Jan. 8, 2020, 8 pages.
"Patent Owner's Preliminary Response Pursuant to 37 C.F.R. § 42.107," Exhibit 2024, filed with the United States Patent and Trademark Office in connection with Case IPR2020-00007 on Jan. 8, 2020, 3 pages.
"Patent Owner's Preliminary Response Pursuant to 37 C.F.R. § 42.107," Exhibit 2025, filed with the United States Patent and Trademark Office in connection with Case IPR2020-00007 on Jan. 8, 2020, 3 pages.
"Patent Owner's Preliminary Response Pursuant to 37 C.F.R. § 42.107," Exhibit 2026, filed with the United States Patent and Trademark Office in connection with Case IPR2020-00007 on Jan. 8, 2020, 13 pages.
"Patent Owner's Preliminary Response Pursuant to 37 C.F.R. § 42.107," Exhibit 2027, filed with the United States Patent and Trademark Office in connection with Case IPR2020-00007 on Jan. 8, 2020, 4 pages.
"Patent Owner's Preliminary Response Pursuant to 37 C.F.R. § 42.107," Exhibit 2028, filed with the United States Patent and Trademark Office in connection with Case IPR2020-00007 on Nov. 14, 2019, 7 pages.
"Patent Owner's Preliminary Response Pursuant to 37 C.F.R. § 42.107," Exhibit 2029, filed with the United States Patent and Trademark Office in connection with Case IPR2020-00007 on Jan. 8, 2020, 25 pages.
"Patent Owner's Preliminary Response Pursuant to 37 C.F.R. § 42.107," Exhibit 2030, filed with the United States Patent and Trademark Office in connection with Case IPR2020-00007 on Jan. 8, 2020, 3 pages.
"Patent Owner's Preliminary Response Pursuant to 37 C.F.R. § 42.107," Exhibit 2031, filed with the United States Patent and Trademark Office in connection with Case IPR2020-00007 on Jan. 8, 2020, 4 pages.
"Patent Owner's Preliminary Response Pursuant to 37 C.F.R. § 42.107," Exhibit 2032, filed with the United States Patent and Trademark Office in connection with Case IPR2020-00007 on Jan. 8, 2020, 4 pages.
European Patent Office, "Extended European Search Report," issued in connection with European Patent Application No. EP 19153494, on Sep. 17, 2019, 13 pages (includes English translation).
"Notification of an Opposition," issued by the European Patent Office in connection with European Patent No. EP3685809 on Mar. 4, 2022, opposition filed by EIS GmbH, 179 pages (includes English translation).
Sparks et al., "Use of Silicone Materials to Simulate Tissue Biomechanics as Related to Deep Tissue Injury," Advances in Skin & Wound Care; vol. 28 No. 2, Feb. 2015; pp. 59-68, 10 pages.
Wu et al., "Simultaneous determination of the nonlinear-elastic properties of skin and subcutaneous tissue in unconfined compression tests," Skin Research and Technology 2007; 13: pp. 34-42, 9 pages.
Zahouani et al., "Characterization of the mechanical properties of a dermal equivalent compared with human skin in vivo by indentation and static friction tests," Skin Research and Technology 2009; 15: pp. 68-76, 9 pages.
The International Bureau of WIPO, "International Search Report and Written Opinion," issued in connection with International Application No. PCT/EP2015/067017, on Jul. 22, 2016, 34 pages (English translation included).
Linder-Ganz et al., "Assessment of mechanical conditions in subdermal tissues during sitting: a combined experimental-MRI and finite element approach," Journal of Biomechanics 40 (2007) pp. 1443-1454, 12 pages.
"Valve," Merriam Webster.com, Merriam Webster, 2016, Dec. 26, 2016, 1 pg.
"Can," Thefreedictionary.com, The free dictionary by Farlex, 2016, Dec. 26, 2016, 1 pg.
"Pump," Merriam Webster.com, Merriam Webster, 2016, Dec. 26, 2016, 1 pg.

(56) References Cited

OTHER PUBLICATIONS

United States Patent and Trademark Office, "Notice of Allowance and Fee(s) Due," issued in connection with U.S. Appl. No. 15/023,471, on May 12, 2017, 10 pages.
United States Patent and Trademark Office, "Non-Final Office action," issued in connection with U.S. Appl. No. 15/302,981, on Jun. 2, 2017, 17 pages.
United States Patent and Trademark Office, "Non-Final Office action," issued in connection with U.S. Appl. No. 15/487,123, on Jun. 2, 2017, 16 pages.
United States Patent and Trademark Office, "Final Office action," issued in connection with U.S. Appl. No. 15/354,599, on Sep. 12, 2017, 47 pages.
United States Patent and Trademark Office, "Final Office action," issued in connection with U.S. Appl. No. 15/487,123, on Sep. 29, 2017, 7 pages.
United States Patent and Trademark Office, "Notice of Allowance and Fee(s) Due," issued in connection with U.S. Appl. No. 15/302,981, on Oct. 12, 2017, 5 pages.
United States Patent and Trademark Office, "Restriction Requirement," issued in connection with U.S. Appl. No. 15/719,085, on Nov. 8, 2017, 6 pages.
United States Patent and Trademark Office, "Supplemental Notice of Allowability," issued in connection with U.S. Appl. No. 15/302,981, on Nov. 17, 2017, 2 pages.
United States Patent and Trademark Office, "Notice of Allowance and Fee(s) Due," issued in connection with U.S. Appl. No. 15/487,123, on Dec. 11, 2017, 5 pages.
United States Patent and Trademark Office, "Non-Final Office action," issued in connection with U.S. Appl. No. 15/354,599, on Dec. 29, 2017, 46 pages.
United States Patent and Trademark Office, "Non-Final Office action," issued in connection with U.S. Appl. No. 15/719,085, on Jan. 25, 2018, 15 pages.
United States Patent and Trademark Office, "Corrected Notice of Allowability," issued in connection with U.S. Appl. No. 15/487,123, on Mar. 13, 2018, 2 pages.
United States Patent and Trademark Office, "Notice of Allowance and Fee(s) Due," issued in connection with U.S. Appl. No. 15/719,085, on Dec. 12, 2018, 11 pages.
United States Patent and Trademark Office, "Supplemental Notice of Allowability," issued in connection with U.S. Appl. No. 15/719,085, on Jan. 11, 2019, 9 pages.
IP Australia, "Examination Report No. 2 for Standard Patent Application," issued in connection with Australian Application No. 2018200852, on Dec. 19, 2018, 4 pages.
International Searching Authority, "International Search Report and Written Opinion," issued in connection with International Application No. PCT/EP2018/082681, on Jan. 30, 2019, 21 pages (includes English translation of pp. 13 to 17).
United States Patent and Trademark Office, "Notice of Allowance," issued in connection with U.S. Appl. No. 15/719,085, on Mar. 20, 2019, 12 pages.
China National Intellectual Property Administration, "First Office Action," issued in connection with Chinese Application No. 201710927530.4, on Mar. 25, 2019, 5 pages (English translation included).
German Patent and Trademark Office, "Examination Report," issued in connection with German Application No. 10 2016 118 911.1, on Nov. 4, 2016, 10 pages. (English translation included.).
Zimmerman et al., "The Gentle Touch Receptors of Mammalian Skin," Special Section: Skin, Science, Nov. 21, 2014, vol. 346, Issue 6212, 6 pages.
Verkauf et al., "Clitoral Size in Normal Women," Obstetrics & Gynecology, vol. 80, No. 1, Jul. 1992, 4 pages.
IP Australia, "Notice of Acceptance for Patent Application," issued in connection with Australian Application No. 2017228536, on Jun. 21, 2018, 3 pages.
International Searching Authority, "Written Opinion," issued in connection with International Application No. PCT/EP2017/075400, on May 18, 2018, 10 pages.
International Searching Authority, "International Search Report," issued in connection with International Application No. PCT/EP2017/075400, on May 18, 2018, 6 pages.
European Patent Office, "Search Report," issued in connection with European Application No. 19153494, on Sep. 11, 2019, 2 pages.
IP Australia, "Opposition—Decision Issued," issued in connection with Australian Patent Application No. 2018203659 on Jan. 5, 2021, 35 pages.
International Searching Authority, "International Search Report," issued in connection with International Application No. PCT/DE2019/100309, on Jul. 15, 2019, 7 pages (includes English translation).
International Searching Authority, "Written Opinion," issued in connection with International Application No. PCT/DE2019/100309, on Jul. 15, 2019, 13 pages (includes English translation).
International Searching Authority, "International Search Report," issued in connection with International Application No. PCT/DE2019/100308, on Oct. 10, 2019, 10 pages (includes English translation).
International Searching Authority, "Written Opinion," issued in connection with International Application No. PCT/DE2019/100308, on Oct. 10, 2019, 21 pages (includes English translation).
EIS, Inc. v. Wow Tech International GmbH, "Defendants' Response to Plaintiff's Second Notice of Supplemental Authority," filed with the United States District Court for the District of Delaware in connection with Case No. 1:19-cv-01227-LPS on Aug. 21, 2020, 191 pages.
European Patent Office, "Search Report," issued in connection with European Application No. 20174260, on Sep. 22, 2020, 18 pages (includes English translation).
International Searching Authority, "International Search Report," issued in connection with International Application No. PCT/DE2019/100860, on Dec. 18, 2019, 6 pages (includes English translation).
International Searching Authority, "Written Opinion," issued in connection with International Application No. PCT/DE2019/100860, on Dec. 18, 2019, 11 pages (includes English translation).
"Decision Granting Petitioner's Request on Rehearing of Decision Denying Institution, Granting Institution of Inter Partes Review," issued by the United States Patent and Trademark Office in connection with Case IPR2020-00007 on Sep. 25, 2020, 22 pages.
IP Australia, "Notice of Opposition," issued in connection with Australian Patent Application No. 2018222907 on Dec. 4, 2020, 110 pages.
Gillan et al., "Vaginal and Pelvic Floor Responses to Sexual Stimulation," Psychophysiology, vol. 16, No. 5 (Sep. 1979), pp. 471-481, 1 page (Abstract only provided).
"Petitioner's Reply to Patent Owner's Response," filed with the United States Patent and Trademark Office in connection with Case IPR2019-01302 on Dec. 4, 2020, 41 pages.
"Petitioner's Reply to Patent Owner's Response," Exhibit 1018, filed with the United States Patent and Trademark Office in connection with Case IPR2019-01302 on Dec. 4, 2020, 79 pages.
"Petitioner's Reply to Patent Owner's Response," Exhibit 1019, filed with the United States Patent and Trademark Office in connection with Case IPR2019-01302 on Dec. 4, 2020, 4 pages.
"Petitioner's Reply to Patent Owner's Response," Exhibit 1020, filed with the United States Patent and Trademark Office in connection with Case IPR2019-01302 on Dec. 4, 2020, 55 pages.
"Petitioner's Reply to Patent Owner's Response," Exhibit 1021, filed with the United States Patent and Trademark Office in connection with Case IPR2019-01302 on Dec. 4, 2020, 16 pages.
"Petitioner's Reply to Patent Owner's Response," Exhibit 1022, filed with the United States Patent and Trademark Office in connection with Case IPR2019-01302 on Dec. 4, 2020, 258 pages.
"Petitioner's Reply to Patent Owner's Response," Exhibit 1023, filed with the United States Patent and Trademark Office in connection with Case IPR2019-01302 on Dec. 4, 2020, 234 pages.
"Petitioner's Reply to Patent Owner's Response," Exhibit 1024, filed with the United States Patent and Trademark Office in connection with Case IPR2019-01302 on Dec. 4, 2020, 19 pages.

(56) References Cited

OTHER PUBLICATIONS

"Petitioner's Reply to Patent Owner's Response," Exhibit 1025, filed with the United States Patent and Trademark Office in connection with Case IPR2019-01302 on Dec. 4, 2020, 22 pages.
"Petitioner's Reply to Patent Owner's Response," Exhibit 1026, filed with the United States Patent and Trademark Office in connection with Case IPR2019-01302 on Dec. 4, 2020, 3 pages.
"Petitioner's Reply to Patent Owner's Response," Exhibit 1027, filed with the United States Patent and Trademark Office in connection with Case IPR2019-01302 on Dec. 4, 2020, 4 pages.
"Petitioner's Reply to Patent Owner's Response," Exhibit 1028, filed with the United States Patent and Trademark Office in connection with Case IPR2019-01302 on Dec. 4, 2020, 4 pages.
"Petitioner's Reply to Patent Owner's Response," Exhibit 1029, filed with the United States Patent and Trademark Office in connection with Case IPR2019-01302 on Dec. 4, 2020, 9 pages.
"Petitioner's Reply to Patent Owner's Response," Exhibit 1030, filed with the United States Patent and Trademark Office in connection with Case IPR2019-01302 on Dec. 4, 2020, 9 pages.
"Petitioner's Reply to Patent Owner's Response," Exhibit 1031, filed with the United States Patent and Trademark Office in connection with Case IPR2019-01302 on Dec. 4, 2020, 18 pages.
"Petitioner's Reply to Patent Owner's Response," Exhibit 1032, filed with the United States Patent and Trademark Office in connection with Case IPR2019-01302 on Dec. 4, 2020, 15 pages.
"Petitioner's Reply to Patent Owner's Response," Exhibit 1033, filed with the United States Patent and Trademark Office in connection with Case IPR2019-01302 on Dec. 4, 2020, 17 pages.
"Petitioner's Reply to Patent Owner's Response," Exhibit 1034, filed with the United States Patent and Trademark Office in connection with Case IPR2019-01302 on Dec. 4, 2020, 2 pages.
"Petitioner's Reply to Patent Owner's Response," Exhibit 1035, filed with the United States Patent and Trademark Office in connection with Case IPR2019-01302 on Dec. 4, 2020, 11 pages.
"Petitioner's Reply to Patent Owner's Response," Exhibit 1036, filed with the United States Patent and Trademark Office in connection with Case IPR2019-01302 on Dec. 4, 2020, 7 pages.
"Petitioner's Reply to Patent Owner's Response," Exhibit 1037, filed with the United States Patent and Trademark Office in connection with Case IPR2019-01302 on Dec. 4, 2020, 17 pages.
"Petitioner's Reply to Patent Owner's Response," Exhibit 1038, filed with the United States Patent and Trademark Office in connection with Case IPR2019-01302 on Dec. 4, 2020, 16 pages.
"Petitioner's Reply to Patent Owner's Response," Exhibit 1039, filed with the United States Patent and Trademark Office in connection with Case IPR2019-01302 on Dec. 4, 2020, 29 pages.
"Petitioner's Reply to Patent Owner's Response," Exhibit 1040, filed with the United States Patent and Trademark Office in connection with Case IPR2019-01302 on Dec. 4, 2020, 74 pages.
"Petitioner's Reply to Patent Owner's Response," Exhibit 1041, filed with the United States Patent and Trademark Office in connection with Case IPR2019-01302 on Dec. 4, 2020, 1 page.
"Petitioner's Reply to Patent Owner's Response," Exhibit 1042, filed with the United States Patent and Trademark Office in connection with Case IPR2019-01302 on Dec. 4, 2020, 1 page.
"Petitioner's Reply to Patent Owner's Response," Exhibit 1043, filed with the United States Patent and Trademark Office in connection with Case IPR2019-01302 on Dec. 4, 2020, 6 pages.
"Petitioner's Reply to Patent Owner's Response," Exhibit 1044, filed with the United States Patent and Trademark Office in connection with Case IPR2019-01302 on Dec. 4, 2020, 136 pages.
"Petitioner's Reply to Patent Owner's Response," Exhibit 1045, filed with the United States Patent and Trademark Office in connection with Case IPR2019-01302 on Dec. 4, 2020, 1 page.
"Petitioner's Reply to Patent Owner's Response," Exhibit 1046, filed with the United States Patent and Trademark Office in connection with Case IPR2019-01302 on Dec. 4, 2020, 1 page.
"Petitioner's Reply to Patent Owner's Response," Exhibit 1047, filed with the United States Patent and Trademark Office in connection with Case IPR2019-01302 on Dec. 4, 2020, 4 pages.
"Petitioner's Reply to Patent Owner's Response," Exhibit 1048, filed with the United States Patent and Trademark Office in connection with Case IPR2019-01302 on Dec. 4, 2020, 5 pages.
"Petitioner's Reply to Patent Owner's Response," Exhibit 1049, filed with the United States Patent and Trademark Office in connection with Case IPR2019-01302 on Dec. 4, 2020, 4 pages.
"Petitioner's Reply to Patent Owner's Response," Exhibit 1050, filed with the United States Patent and Trademark Office in connection with Case IPR2019-01302 on Dec. 4, 2020, 9 pages.
"Patent Owner's Amended Mandatory Notices Pursuant to 37 C.F.R. 42.8," filed with the United States Patent and Trademark Office in connection with Case IPR2019-01302 on Jan. 12, 2021, 9 pages.
"Patent Owner's Sur-Reply Pursuant to 37 C.F.R. 42.23," filed with the United States Patent and Trademark Office in connection with Case IPR2019-01302 on Jan. 15, 2021, 38 pages.
"Patent Owner's Sur-Reply Pursuant to 37 C.F.R. 42.23," Exhibit 2048, filed with the United States Patent and Trademark Office in connection with Case IPR2019-01302 on Jan. 15, 2021, 39 pages.
"Patent Owner's Sur-Reply Pursuant to 37 C.F.R. 42.23," Exhibit 2049, filed with the United States Patent and Trademark Office in connection with Case IPR2019-01302 on Jan. 15, 2021, 13 pages.
"Patent Owner's Sur-Reply Pursuant to 37 C.F.R. 42.23," Exhibit 2050, filed with the United States Patent and Trademark Office in connection with Case IPR2019-01302 on Jan. 15, 2021, 14 pages.
"Patent Owner's Sur-Reply Pursuant to 37 C.F.R. 42.23," Exhibit 2051, filed with the United States Patent and Trademark Office in connection with Case IPR2019-01302 on Jan. 15, 2021, 3 pages.
"Petitioner's Reply to Patent Owner's Response," filed with the United States Patent and Trademark Office in connection with Case IPR2019-01444 on Jan. 26, 2021, 41 pages.
"Petitioner's Reply to Patent Owner's Response," Exhibit 1013, filed with the United States Patent and Trademark Office in connection with Case IPR2019-01444 on Jan. 26, 2021, 32 pages.
"Petitioner's Reply to Patent Owner's Response," Exhibit 1014, filed with the United States Patent and Trademark Office in connection with Case IPR2019-01444 on Jan. 26, 2021, 29 pages.
"Petitioner's Reply to Patent Owner's Response," Exhibit 1015, filed with the United States Patent and Trademark Office in connection with Case IPR2019-01444 on Jan. 26, 2021, 196 pages.
"Petitioner's Reply to Patent Owner's Response," Exhibit 1016, filed with the United States Patent and Trademark Office in connection with Case IPR2019-01444 on Jan. 26, 2021, 253 pages.
"Petitioner's Reply to Patent Owner's Response," Exhibit 1017, filed with the United States Patent and Trademark Office in connection with Case IPR2019-01444 on Jan. 26, 2021, 88 pages.
"Petitioner's Reply to Patent Owner's Response," Exhibit 1018, filed with the United States Patent and Trademark Office in connection with Case IPR2019-01444 on Jan. 26, 2021, 93 pages.
"Petitioner's Reply to Patent Owner's Response," Exhibit 1019, filed with the United States Patent and Trademark Office in connection with Case IPR2019-01444 on Jan. 26, 2021, 4 pages.
"Petitioner's Reply to Patent Owner's Response," Exhibit 1020, filed with the United States Patent and Trademark Office in connection with Case IPR2019-01444 on Jan. 26, 2021, 41 pages.
"Petitioner's Reply to Patent Owner's Response," Exhibit 1021, filed with the United States Patent and Trademark Office in connection with Case IPR2019-01444 on Jan. 26, 2021, 16 pages.
"Petitioner's Reply to Patent Owner's Response," Exhibit 1022, filed with the United States Patent and Trademark Office in connection with Case IPR2019-01444 on Jan. 26, 2021, 258 pages.
"Petitioner's Reply to Patent Owner's Response," Exhibit 1023, filed with the United States Patent and Trademark Office in connection with Case IPR2019-01444 on Jan. 26, 2021, 234 pages.
"Petitioner's Reply to Patent Owner's Response," Exhibit 1024, filed with the United States Patent and Trademark Office in connection with Case IPR2019-01444 on Jan. 26, 2021, 11 pages.
"Petitioner's Reply to Patent Owner's Response," Exhibit 1025, filed with the United States Patent and Trademark Office in connection with Case IPR2019-01444 on Jan. 26, 2021, 6 pages.
"Petitioner's Reply to Patent Owner's Response," Exhibit 1026, filed with the United States Patent and Trademark Office in connection with Case IPR2019-01444 on Jan. 26, 2021, 3 pages.

(56) References Cited

OTHER PUBLICATIONS

"Petitioner's Reply to Patent Owner's Response," Exhibit 1027, filed with the United States Patent and Trademark Office in connection with Case IPR2019-01444 on Jan. 26, 2021, 4 pages.
"Petitioner's Reply to Patent Owner's Response," Exhibit 1028, filed with the United States Patent and Trademark Office in connection with Case IPR2019-01444 on Jan. 26, 2021, 4 pages.
"Petitioner's Reply to Patent Owner's Response," Exhibit 1029, filed with the United States Patent and Trademark Office in connection with Case IPR2019-01444 on Jan. 26, 2021, 9 pages.
"Petitioner's Reply to Patent Owner's Response," Exhibit 1030, filed with the United States Patent and Trademark Office in connection with Case IPR2019-01444 on Jan. 26, 2021, 9 pages.
"Petitioner's Reply to Patent Owner's Response," Exhibit 1031, filed with the United States Patent and Trademark Office in connection with Case IPR2019-01444 on Jan. 26, 2021, 18 pages.
"Petitioner's Reply to Patent Owner's Response," Exhibit 1032, filed with the United States Patent and Trademark Office in connection with Case IPR2019-01444 on Jan. 26, 2021, 15 pages.
"Petitioner's Reply to Patent Owner's Response," Exhibit 1033, filed with the United States Patent and Trademark Office in connection with Case IPR2019-01444 on Jan. 26, 2021, 17 pages.
"Petitioner's Reply to Patent Owner's Response," Exhibit 1034, filed with the United States Patent and Trademark Office in connection with Case IPR2019-01444 on Jan. 26, 2021, 2 pages.
"Petitioner's Reply to Patent Owner's Response," Exhibit 1035, filed with the United States Patent and Trademark Office in connection with Case IPR2019-01444 on Jan. 26, 2021, 11 pages.
"Petitioner's Reply to Patent Owner's Response," Exhibit 1036, filed with the United States Patent and Trademark Office in connection with Case IPR2019-01444 on Jan. 26, 2021, 18 pages.
"Petitioner's Reply to Patent Owner's Response," Exhibit 1037, filed with the United States Patent and Trademark Office in connection with Case IPR2019-01444 on Jan. 26, 2021, 17 pages.
"Petitioner's Reply to Patent Owner's Response," Exhibit 1038, filed with the United States Patent and Trademark Office in connection with Case IPR2019-01444 on Jan. 26, 2021, 16 pages.
"Petitioner's Reply to Patent Owner's Response," Exhibit 1039, filed with the United States Patent and Trademark Office in connection with Case IPR2019-01444 on Jan. 26, 2021, 5 pages.
"Petitioner's Reply to Patent Owner's Response," Exhibit 1040, filed with the United States Patent and Trademark Office in connection with Case IPR2019-01444 on Jan. 26, 2021, 74 pages.
"Petitioner's Reply to Patent Owner's Response," Exhibit 1041, filed with the United States Patent and Trademark Office in connection with Case IPR2019-01444 on Jan. 26, 2021, 5 pages.
"Petitioner's Reply to Patent Owner's Response," Exhibit 1043, filed with the United States Patent and Trademark Office in connection with Case IPR2019-01444 on Jan. 26, 2021, 6 pages.
"Petitioner's Reply to Patent Owner's Response," Exhibit 1044, filed with the United States Patent and Trademark Office in connection with Case IPR2019-01444 on Jan. 26, 2021, 136 pages.
"Petitioner's Reply to Patent Owner's Response," Exhibit 1045, filed with the United States Patent and Trademark Office in connection with Case IPR2019-01444 on Jan. 26, 2021, 1 page.
"Petitioner's Reply to Patent Owner's Response," Exhibit 1046, filed with the United States Patent and Trademark Office in connection with Case IPR2019-01444 on Jan. 26, 2021, 1 page.
"Petitioner's Reply to Patent Owner's Response," Exhibit 1047, filed with the United States Patent and Trademark Office in connection with Case IPR2019-01444 on Jan. 26, 2021, 4 pages.
"Petitioner's Reply to Patent Owner's Response," Exhibit 1048, filed with the United States Patent and Trademark Office in connection with Case IPR2019-01444 on Jan. 26, 2021, 5 pages.
"Petitioner's Reply to Patent Owner's Response," Exhibit 1049, filed with the United States Patent and Trademark Office in connection with Case IPR2019-01444 on Jan. 26, 2021, 4 pages.
"Petitioner's Reply to Patent Owner's Response," Exhibit 1050, filed with the United States Patent and Trademark Office in connection with Case IPR2019-01444 on Jan. 26, 2021, 12 pages.

*EIS, Inc.* v. *Wow Tech International GmbH*, "Memorandum Opinion," issued by the United States District Court for the District of Delaware in connection with Case No. 1:19-cv-01227-LPS on Nov. 30, 2020, 26 pages.
*EIS, Inc.* v. *Wow Tech International GmbH*, "Second Amended Complaint," filed with the United States District Court for the District of Delaware in connection with Case No. 1:19-cv-01227-LPS on Dec. 22, 2020, 748 pages. (Uploaded in two parts.).
European Patent Office, "Notification under Article 94 (3) EPC," issued in connection with European Application No. 18206800.7, on Nov. 12, 2020, 10 pages. (English translation included.).
"Notification of an Opposition," issued by the European Patent Office in connection with European Patent No. EP3405158 on Oct. 5, 2020, opposition filed by EIS GmbH, 88 pages (includes English translation).
Mexican Institute of IP, "First Office Action," issued in connection with Mexican Patent Application No. MX/a/2017/012780, dated Jan. 8, 2021, 5 pages (includes English translation).
"Patent Owner's Sur-Reply Pursuant to 37 C.F.R. 42.23," filed with the United States Patent and Trademark Office in connection with Case IPR2019-01444 on Mar. 9, 2021, 38 pages.
"Patent Owner's Sur-Reply Pursuant to 37 C.F.R. 42.23, Exhibit 2061," filed with the United States Patent and Trademark Office in connection with Case IPR2019-01444 on Mar. 9, 2021, 39 pages.
"Petitioner's Reply to Patent Owner's Response," filed with the United States Patent and Trademark Office in connection with Case IPR2020-00007 on Mar. 12, 2021, 39 pages.
"Petitioner's Reply to Patent Owner's Response, Exhibit 1014" filed with the United States Patent and Trademark Office in connection with Case IPR2020-00007 on Mar. 12, 2021, 177 pages.
"Petitioner's Reply to Patent Owner's Response, Exhibit 1017" filed with the United States Patent and Trademark Office in connection with Case IPR2020-00007 on Mar. 12, 2021, 192 pages.
"Petitioner's Reply to Patent Owner's Response, Exhibit 1018" filed with the United States Patent and Trademark Office in connection with Case IPR2020-00007 on Mar. 12, 2021, 74 pages.
"Petitioner's Reply to Patent Owner's Response, Exhibit 1020" filed with the United States Patent and Trademark Office in connection with Case IPR2020-00007 on Mar. 12, 2021, 42 pages.
"Petitioner's Reply to Patent Owner's Response, Exhibit 1036" filed with the United States Patent and Trademark Office in connection with Case IPR2020-00007 on Mar. 12, 2021, 7 pages.
"Petitioner's Reply to Patent Owner's Response, Exhibit 1037" filed with the United States Patent and Trademark Office in connection with Case IPR2020-00007 on Mar. 12, 2021, 3 pages.
"Petitioner's Reply to Patent Owner's Response, Exhibit 1043" filed with the United States Patent and Trademark Office in connection with Case IPR2020-00007 on Mar. 12, 2021, 8 pages.
IP Australia, "Opposition—Section 104 Amendments," issued in connection with Australian Patent Application No. 2018203659 on Mar. 23, 2021, 6 pages.
"Opponent's Reply," filed with the European Patent Office by Fun Factory GmbH in connection with European Patent No. EP2976057 on Apr. 9, 2021, 233 pages (includes English translation).
"Opponent's Reply, Exhibit A2," filed with the European Patent Office by Fun Factory GmbH in connection with European Patent No. EP2976057 on Apr. 9, 2021, 24 pages (includes English translation).
"Opponent's Reply, Exhibit D34," filed with the European Patent Office by Fun Factory GmbH in connection with European Patent No. EP2976057 on Apr. 9, 2021, 1 page.
"Opponent's Reply, Exhibit D35," filed with the European Patent Office by Fun Factory GmbH in connection with European Patent No. EP2976057 on Apr. 9, 2021, 10 pages (includes English translation).
"Opponent's Reply, Exhibit E4," filed with the European Patent Office by Fun Factory GmbH in connection with European Patent No. EP2976057 on Apr. 9, 2021, 7 pages (includes English translation).
"Opponent's Reply," filed with the European Patent Office by Fun Factory GmbH in connection with European Patent No. EP3308762 on Apr. 9, 2021, 119 pages (includes English translation).

(56) References Cited

OTHER PUBLICATIONS

"Opponent's Reply," filed with the European Patent Office by EIS GmbH in connection with European Patent No. EP3308762 on Apr. 9, 2021, 111 pages (includes English translation).
Patent Owner's Sur-Reply Pursuant to 37 C.F.R. 42.23, filed with the United States Patent and Trademark Office in connection with Case IPR2020-00007 on Apr. 23, 2021, 40 pages.
"Opposition to a European Patent," filed with the European Patent Office by Fun Factory GmbH in connection with European Patent No. EP3305266 on Feb. 11, 2021, 138 pages (includes English translation).
"Opposition to a European Patent, Exhibit D15" filed with the European Patent Office by Fun Factory GmbH in connection with European Patent No. EP3305266 on Feb. 11, 2021, 62 pages (includes English translation).
"Opposition to a European Patent," filed with the European Patent Office by EIS GmbH in connection with European Patent No. EP3305266 on Feb. 15, 2021, 199 pages (includes English translation).
"Opposition to a European Patent, Exhibit E36" filed with the European Patent Office by EIS GmbH in connection with European Patent No. EP3305266 on Feb. 15, 2021, 2 pages.
"Statement of Grounds and Particulars of Opposition," filed with IP Australia in connection with Australian Patent Application No. 2018222907 on Feb. 24, 2021, 15 pages.
"Evidence in Support," filed with IP Australia by EIS GmbH in connection with Australian Patent Application No. 2018222907 on May 18, 2021, 53 pages.
Canadian Patent Office, "Office Action," issued in connection with Canadian Application No. 2,978,739, on Jan. 25, 2018, 5 pages.
European Patent Office, "Message," issued in connection with opposition of European Patent No. EP3308762 on Jun. 4, 2021, 40 pages (includes English translation).
European Patent Office, "Message," issued in connection with opposition of European Patent No. EP2976057 on Jun. 1, 2021, 35 pages (includes English translation).
United States Patent and Trademark Office, "Judgment, Final Written Decision," issued in connection with Case IPR2019-01302 on Jun. 14, 2021, 75 pages.
German Patent and Trademark Office, "Examination Report," issued in connection with German Application No. 10 2015 017 096.1, on Aug. 13, 2021, 23 pages (includes English translation).
United States Patent and Trademark Office, "Judgment, Final Written Decision," issued in connection with Case IPR2020-00007 on Sep. 23, 2021, 78 pages.
"Petitioner's Notice of Appeal," filed with the United States Patent and Trademark Office in connection with Case IPR2019-01302 on Aug. 13, 2021, 80 pages.
"Opposition to a German Patent," filed with the German Patent and Trademark Office by Fun Factory GmbH in connection with German Patent No. 10 2013 022 393.8 on Sep. 9, 2021, 175 pages (includes English translation).
"Opposition to a German Patent, Exhibit 5A," filed with the German Patent and Trademark Office by Fun Factory GmbH in connection with German Patent No. 10 2013 022 393.8 on Sep. 9, 2021, 10 pages.
*EIS Inc.* v. *IntiHealth Ger GmbH et al.*, "Plaintiff EIS Inc"s Answer and Affirmative Defenses to Defendant Novoluto"s Counterclaims," filed with the United States District Court for the District of Delaware, case No. 1:19-cv-01227-LPS, Nov. 12, 2021, 53 pages.
*EIS Inc.* v. *IntiHealth Ger GmbH et al.*, "Plaintiff EIS Inc"s Answer and Affirmative Defenses to Defendant Novoluto"s Counterclaims, Exhibit A," filed with the United States District Court for the District of Delaware, case No. 1:19-cv-01227-LPS, Nov. 12, 2021, 95 pages.
*EIS Inc.* v. *IntiHealth Ger GmbH et al.*, "Plaintiff EIS Inc"s Answer and Affirmative Defenses to Defendant Novoluto"s Counterclaims, Exhibit B," filed with the United States District Court for the District of Delaware, case No. 1:19-cv-01227-LPS, Nov. 12, 2021, 91 pages.
*EIS Inc.* v. *IntiHealth Ger GmbH et al.*, "Plaintiff EIS Inc"s Answer and Affirmative Defenses to Defendant Novoluto"s Counterclaims, Exhibit C," filed with the United States District Court for the District of Delaware, case No. 1:19-cv-01227-LPS, Nov. 12, 2021, 88 pages.
*EIS Inc.* v. *IntiHealth Ger GmbH et al.*, "Plaintiff EIS Inc"s Answer and Affirmative Defenses to Defendant Novoluto"s Counterclaims, Exhibit D," filed with the United States District Court for the District of Delaware, case No. 1:19-cv-01227-LPS, Nov. 12, 2021, 5 pages.
*EIS Inc.* v. *IntiHealth Ger GmbH et al.*, "Plaintiff EIS Inc"s Answer and Affirmative Defenses to Defendant Novoluto"s Counterclaims, Exhibit E," filed with the United States District Court for the District of Delaware, case No. 1:19-cv-01227-LPS, Nov. 12, 2021, 7 pages.
*EIS Inc.* v. *IntiHealth Ger GmbH et al.*, "Plaintiff EIS Inc"s Answer and Affirmative Defenses to Defendant Novoluto"s Counterclaims, Exhibit F," filed with the United States District Court for the District of Delaware, case No. 1:19-cv-01227-LPS, Nov. 12, 2021, 6 pages.
*EIS Inc.* v. *IntiHealth Ger GmbH et al.*, "Plaintiff EIS Inc"s Answer and Affirmative Defenses to Defendant Novoluto"s Counterclaims, Exhibit G," filed with the United States District Court for the District of Delaware, case No. 1:19-cv-01227-LPS, Nov. 12, 2021, 9 pages.
*EIS Inc.* v. *IntiHealth Ger GmbH et al.*, "Plaintiff EIS Inc"s Answer and Affirmative Defenses to Defendant Novoluto"s Counterclaims, Exhibit H," filed with the United States District Court for the District of Delaware, case No. 1:19-cv-01227-LPS, Nov. 12, 2021, 54 pages.
*EIS Inc.* v. *IntiHealth Ger GmbH et al.*, "Plaintiff EIS Inc"s Answer and Affirmative Defenses to Defendant Novoluto"s Counterclaims, Exhibit I," filed with the United States District Court for the District of Delaware, case No. 1:19-cv-01227-LPS, Nov. 12, 2021, 17 pages.
*EIS Inc.* v. *IntiHealth Ger GmbH et al.*, "Plaintiff EIS Inc"s Answer and Affirmative Defenses to Defendant Novoluto"s Counterclaims, Exhibit J," filed with the United States District Court for the District of Delaware, case No. 1:19-cv-01227-LPS, Nov. 12, 2021, 30 pages.
*EIS Inc.* v. *IntiHealth Ger GmbH et al.*, "Letter to The Honorable Leonard P. Stark from Paul D. Brown regarding Motion to Strike Invalidity Contentions," filed with the United States District Court for the District of Delaware in connection with Case No. 1:19-cv-1227-LPS on Nov. 17, 2021, 3 pages.
*EIS Inc.* v. *IntiHealth Ger GmbH et al.*, "Letter to The Honorable Leonard P. Stark from Paul D. Brown regarding Motion to Strike Invalidity Contentions, Exhibit 1," filed with the United States District Court for the District of Delaware in connection with Case No. 1:19-cv-1227-LPS on Nov. 17, 2021, 382 pages.
Josefson, D., FDA Approves Device for Female Sexual Dysfunction, 320 BMJ 7247 at 1427 (2000).
*EIS Inc.* v. *IntiHealth Ger GmbH et al.*, "Letter to the Honorable Leonard P. Stark in Opposition to Defendants' Motion to Strike EIS's Initial Invalidity Contentions," filed with the United States District Court for the District of Delaware in connection with Case No. 1:19-cv-1227-LPS on Nov. 30, 2021, 7 pages.
*EIS Inc.* v. *IntiHealth Ger GmbH et al.*, "Letter to the Honorable Leonard P. Stark from Gregory E. Stuhlman, Esquire Regarding Motion to Strike Invalidity Contentions," filed with the United States District Court for the District of Delaware in connection with Case No. 1:19-cv-1227-LPS on Dec. 3, 2021, 2 pages.
*EIS Inc.* v. *IntiHealth Ger GmbH et al.*, "Counterclaim Defendants EIS GmbH, Triple A Import GmbH, and Triple A Marketing GmbH's Answer and Affirmative Defenses to Defendant Novoluto's Counterclaims," filed with the United States District Court for the District of Delaware in connection with Case No. 1:19-cv-1227-LPS on Dec. 13, 2021, 54 pages.
*EIS Inc.* v. *IntiHealth Ger GmbH et al.*, "Plaintiff EIS Inc.'s Opening Brief in Support of its Motion for Temporary Restraining Order and Preliminary Injunction (Public Version)," filed with the United States District Court for the District of Delaware in connection with Case No. 1:19-cv-1227-LPS on Dec. 15, 2021, 26 pages.

(56) References Cited

OTHER PUBLICATIONS

*EIS Inc.* v. *IntiHealth Ger GmbH et al.*, "Plaintiff EIS Inc.'s Opening Brief in Support of its Motion for Temporary Restraining Order and Preliminary Injunction (Public Version), Exhibit A-12" filed with the United States District Court for the District of Delaware in connection with Case No. 1:19-cv-1227-LPS on Dec. 15, 2021, 22 pages.
*EIS Inc.* v. *IntiHealth Ger GmbH et al.*, "Letter to the Honorable Leonard P. Stark Regarding Motion for Temporary Restraining Order (Public Version)," filed with the United States District Court for the District of Delaware in connection with Case No. 1:19-cv-1227-LPS on Dec. 15, 2021, 6 pages.
*EIS Inc.* v. *IntiHealth Ger GmbH et al.*, "Letter to the Honorable Leonard P. Stark Regarding Reply in Support of Plaintiff EIS's Inc.'s Motion for Temporary Restraining Order and Preliminary Injunction (Public Version)," filed with the United States District Court for the District of Delaware in connection with Case No. 1:19-cv-1227-LPS on Dec. 15, 2021, 4 pages.
United States Patent and Trademark Office, "Final Office Action," issued in connection with U.S. Appl. No. 15/965,117, on Dec. 6, 2018, 15 pages.
United States Patent and Trademark Office, "Final Office Action," issued in connection with U.S. Appl. No. 15/965,208, on Dec. 10, 2018, 19 pages.
United States Patent and Tradmark Office, "Non-Final Office action," issued in connection with U.S. Appl. No. 15/354,599, on Nov. 13, 2018, 34 pages.
New Zealand Intellectual Property Office, "Further Examination Report," issued in connection with NZ Application No. 735229, on Aug. 23, 2018, 4 pages.
Singapore Patent Office, "Written Opinion," issued in connection with Singapore Application No. 11201707395T, on Jul. 24, 2018, 8 pages.
"Statement of Grounds and Particulars of Opposition," filed with the Australian Patent Office in connection with Australian Patent Application No. 2015386680 on Sep. 21, 2018, 11 pages.
Taiwan Patent Office, "English Translation of Office Action," issued in connection with Taiwanese Application No. 106132654, on Aug. 9, 2018, 3 pages.
United States Patent and Trademark Office, "Non-Final Office action," issued in connection with U.S. Appl. No. 15/719,085 on Aug. 31, 2018, 17 pages.
European Patent Office, "Search Report," issued in connection with European Application No. 17190856, on Apr. 27, 2018, 9 pages (includes English translation).
Singapore Patent Office, "Search Report and Written Opinion," issued in connection with Singapore Application No. 10201707736X, on May 18, 2018, 9 pages.
United States Patent and Trademark Office, "Final Office action," issued in connection with U.S. Appl. No. 15/354,599, on Jun. 28, 2018, 39 pages.
United States Patent Trademark Office, "Non-Final Office action," issued in connection with U.S. Appl. No. 15/965,117, on Jun. 29, 2018, 32 pages.
United States Patent and Trademark Office, "Non-Final Office action," issued connection with U.S. Appl. No. 15/965,208, on Jun. 29, 2018, 31 pages.
United States Patent and Trademark Office, "Final Office action," issued in connection with U.S. Appl. No. 15/719,085, on May 7, 2018, 14 pages.
Canadian Patent Office, "Office Action," issued in connection with Canadian Application No. 2,978,739, on Jun. 12, 2018, 4 pages.
New Zealand Intellectual Property Office, "Office Action," issued in connection with NZ Application No. 735370, on Mar. 1, 2018, 5 pages.
European Patent Office, "Search Report," issued in connection with European Application No. 17202394.7, on Mar. 8, 2018, 4 pages.
European Patent Office, "Announcement According to Article 94 ( 3 ) EPU," issued in connection with European Application No. 14741640.8, on Mar. 8, 2018, 12 pages (includes English translation).
IP Australia, "Examination Report," issued in connection with Australian Application No. 2017228536, on Dec. 20, 2017, 5 pages.
United States Patent and Trademark Office, "Notice of Allowance," issued in connection with U.S. Appl. No. 15/888,568, dated May 11, 2022, 8 pages.
International Searching Authority, "Partial International Search Report," issued in connection with International Application No. PCT/EP2017/075400, on Mar. 6, 2018, 46 pages (includes English translation).
International Searching Authority, "Partial International Search Report," issued in connection with International Application No. PCT/EP2017/075399, on Mar. 1, 2018, 34 pages (includes English translation).
United States Patent and Trademark Office, "Non-Final Office action," issued in connection with U.S. Appl. No. 15/023,471, on Aug. 26, 2016, 26 pages.
United States Patent and Trademark Office, "Final Office action," issued in connection with U.S. Appl. No. 15/023,471, on Jan. 6, 2017, 28 pages.
United States Patent and Trademark Office, "Non-final Office action," issued in connection with U.S. Appl. No. 15/354,599, on Feb. 24, 2017, 38 pages.
Maria M. Kettenring, "Erotische Partnermassage", Grafe und User Publishers, 2004, 5 pages (includes English summary).
"Gesundheitsminister. Mehr Sex gegen Bluthochdruck," http://www.heilpraxisnet.delnaturheilpraxis/sex-gegen-bluthochdruck-665.php, Apr. 2010, 2 pages (English translation included).
Beate Lakotta, "Schmerz und Gluckseligkeit, Der Spiegel", pp. 136-138, Jun. 2006, 7 pages (English translation included).
"Sex hilflt gegen Erkaltung," Focus Online, Dec. 5, 2004; 2 pages (English translation included).
United States Patent and Trademark Office, "Non-Final Office action," issued in connection with U.S. Appl. No. 15/888,568, on Jan. 10, 2019, 15 pages.
United States Patent and Trademark Office, "Final Office Action," issued in connection with U.S. Appl. No. 15/888,568 on Oct. 29, 2019, 7 pages.
United States Patent and Trademark Office, "Final Office Action," issued in connection with U.S. Appl. No. 15/888,568, dated Apr. 16, 2020, 7 pages.
United States Patent and Trademark Office, "Final Office Action," issued in connection with U.S. Appl. No. 15/888,568, dated on Oct. 28, 2020, 7 pages.
United States Patent and Trademark Office, "Notice of Allowance," issued in connection with U.S. Appl. No. 15/888,568, dated Feb. 8, 2021, 8 pages.
United States Patent and Trademark Office, "Supplemental Notice of Allowability," issued in connection with U.S. Appl. No. 15/888,568, dated Apr. 5, 2021, 3 pages.
United States Patent and Trademark Office, "Supplemental Notice of Allowability, " issued in connection with U.S. Appl. No. 15/888,568, dated on Apr. 26, 2021, 3 pages.
United States Patent and Trademark Office, "Corrected Notice of Allowability," issued in connection with U.S. Appl. No. 15/888,568, dated May 26, 2021, 3 pages.
United States Patent and Trademark Office, "Corrected Notice of Allowability," issued in connection with U.S. Appl. No. 15/888,568, dated Jul. 2, 2021, 3 pages.
United States Patent and Trademark Office, "Notice of Allowance," issued in connection with U.S. Appl. No. 15/888,568, dated Aug. 10, 2021, 8 pages.
United States Patent and Trademark Office, "Corrected Notice of Allowability," issued in connection with U.S. Appl. No. 15/888,568, dated Oct. 12, 2021, 3 pages.
United States Patent and Trademark Office, "Notice of Allowance," issued in connection with U.S. Appl. No. 15/888,568, dated Dec. 1, 2021, 8 pages.

(56) References Cited

OTHER PUBLICATIONS

United States Patent and Trademark Office, "Corrected Notice of Allowability," issued in connection with U.S. Appl. No. 15/888,568, dated Dec. 30, 2021, 3 pages.
United States Patent and Trademark Office, "Corrected Notice of Allowability," issued in connection with U.S. Appl. No. 15/888,568, dated Mar. 24, 2022, 3 pages.
"Accompanying Letter for Later Submitted Documents" filed with the European Patent Office by Fun Factory GmbH in connection with European Patent No. EP2976057 on Mar. 2, 2022, 24 pages (includes English translation).
"Accompanying Letter for Later Submitted Documents, Exhibits 50 and 50a" filed with the European Patent Office by Fun Factory GmbH in connection with European Patent No. EP2976057 on Mar. 2, 2022, 48 pages.
"Accompanying Letter for Later Submitted Documents" filed with the European Patent Office by Fun Factory GmbH in connection with European Patent No. EP3308762 on Mar. 2, 2022, 24 pages (includes English Translation).
"Accompanying Letter for Later Submitted Documents, Exhibits 43 and 43a" filed with the European Patent Office by Fun Factory GmbH in connection with European Patent No. EP3308762 on Mar. 2, 2022, 48 pages.
*EIS Inc.* v. *IntiHealth Ger GmbH et al.*, "Joint Claim Construction Chart," filed with the United States District Court for the District of Delaware, case No. 1:19-cv-01227-VAC-MPT, Mar. 23, 2022, 13 pages.
*EIS Inc.* v. *IntiHealth Ger GmbH et al.*, "Appendix to Joint Claim Construction Chart," filed with the United States District Court for the District of Delaware, case No. 1:19-cv-01227-VAC-MPT, Mar. 23, 2022, 267 pages (uploaded in two parts).
"Grounds of Appeal," filed with the European Patent Office by Fun Factory GmbH in connection with European Patent No. EP2976057 on Jan. 3, 2022, 203 pages (includes English translation).
"Grounds of Appeal," filed with the European Patent Office by EIS GmBH in connection with European Patent No. EP2976057 on Jan. 3, 2022, 279 pages (includes English translation).
"Grounds of Appeal, Exhibit B1a" filed with the European Patent Office by EIS GmBH in connection with European Patent No. EP2976057 on Jan. 3, 2022, 2 pages (includes English translation).
"Grounds of Appeal, Exhibit D41" filed with the European Patent Office by EIS GmBH in connection with European Patent No. EP2976057 on Jan. 3, 2022, 2 pages (includes English translation).
"Grounds of Appeal, Exhibit D42" filed with the European Patent Office by EIS GmBH in connection with European Patent No. EP2976057 on Jan. 3, 2022, 18 pages (includes English translation).
"Grounds of Appeal, Exhibit D43" filed with the European Patent Office by EIS GmBH in connection with European Patent No. EP2976057 on Jan. 3, 2022, 12 pages (includes English translation).
"Grounds of Appeal, Exhibit D44" filed with the European Patent Office by EIS GmBH in connection with European Patent No. EP2976057 on Jan. 3, 2022, 11 pages (includes English translation).
"Grounds of Appeal, Exhibit D45" filed with the European Patent Office by EIS GmBH in connection with European Patent No. EP2976057 on Jan. 3, 2022, 4 pages (includes English translation).
"Grounds of Appeal, Exhibit D46" filed with the European Patent Office by EIS GmBH in connection with European Patent No. EP2976057 on Jan. 3, 2022, 13 pages.
"Grounds of Appeal, Exhibit D47" filed with the European Patent Office by EIS GmBH in connection with European Patent No. EP2976057 on Jan. 3, 2022, 3 pages.
"Grounds of Appeal, Exhibit D48" filed with the European Patent Office by EIS GmBH in connection with European Patent No. EP2976057 on Jan. 3, 2022, 4 pages (includes English translation).
"Grounds of Appeal, Exhibit D49" filed with the European Patent Office by EIS GmBH in connection with European Patent No. EP2976057 on Jan. 3, 2022, 4 pages (includes English translation).
"Grounds of Appeal," filed with the European Patent Office by Fun Factory GmbH in connection with European Patent No. EP3308762 on Jan. 3, 2022, 198 pages (includes English translation).
"Grounds of Appeal," filed with the European Patent Office by EIS GmBH in connection with European Patent No. EP3308762 on Jan. 3, 2022, 270 pages (includes English translation).
"Grounds of Appeal, Exhibit B1a" filed with the European Patent Office by EIS GmBH in connection with European Patent No. EP3308762 on Jan. 3, 2022, 2 pages (includes English translation).
"Grounds of Appeal, Exhibit D40" filed with the European Patent Office by EIS GmBH in connection with European Patent No. EP3308762 on Jan. 3, 2022, 4 pages (includes English translation).
"Grounds of Appeal, Exhibit D41" filed with the European Patent Office by EIS GmBH in connection with European Patent No. EP3308762 on Jan. 3, 2022, 4 pages (includes English translation).
"Grounds of Appeal, Exhibit D42" filed with the European Patent Office by EIS GmBH in connection with European Patent No. EP3308762 on Jan. 3, 2022, 4 pages (includes English translation).
"Follow-up to Statement of Complaint," filed with the European Patent Office by EIS GmBH in connection with European Patent No. EP2976057 on Apr. 26, 2022, 47 pages (includes English translation).
"Follow-up to Statement of Complaint, Exhibit D51," filed with the European Patent Office by EIS GmBH in connection with European Patent No. EP2976057 on Apr. 26, 2022, 17 pages (includes English translation).
"Follow-up to Statement of Complaint, Exhibit B4," filed with the European Patent Office by EIS GmBH in connection with European Patent No. EP2976057 on Apr. 26, 2022, 14 pages (includes English translation).
"Follow-up to Statement of Complaint," filed with the European Patent Office by EIS GmBH in connection with European Patent No. EP3308762 on Apr. 26, 2022, 46 pages (includes English translation).
"Follow-up to Statement of Complaint, Exhibit D44," filed with the European Patent Office by EIS GmBH in connection with European Patent No. EP3308762 on Apr. 26, 2022, 17 pages (includes English translation).
"Follow-up to Statement of Complaint, Exhibit B4," filed with the European Patent Office by EIS GmBH in connection with European Patent No. EP3308762 on Apr. 26, 2022, 18 pages (includes English translation).
"Decision Denying Institution of Inter Partes Review," issued by the United States Patent and Trademark Office in connection with Case IPR2019-01302 on Jan. 13, 2020, 21 pages.
*EIS, Inc.* v. *Wow Tech International GmbH*, "Letter to the Honorable Leonard P. Stark from Jack B. Blumenfeld regarding Discovery Dispute," filed with the United States District Court for the District of Delaware in connection with Case No. 1:19-cv-1277-LPS on Dec. 5, 2019, 176 pages.
*EIS, Inc.* v. *Wow Tech International GmbH*, "Letter to the Honorable Leonard P. Stark from Paul D. Brown regarding Discovery Dispute," filed with the United States District Court for the District of Delaware in connection with Case No. 1:19-cv-1277-LPS on Dec. 6, 2019, 4 pages.
United Stated Patent and Trademark Office, "Notice of Allowance," issued in connection with U.S. Appl. No. 15/719,085, on Oct. 15, 2019, 12 pages.
United States Patent and Trademark Office, "Non-Final Office Action," issued in connection with U.S. Appl. No. 15/965,117, filed Jun. 27, 2019, 15 pages.
"English Translation of Grounds of Appeal," filed in connection with opposition of German Patent No. 102013110501.7 on Dec. 21, 2018, 44 pages (includes English translation of Exhibit B1).
"English Translation of Exhibit B2 of Grounds of Appeal," filed with the German Patent and Trademark in connection with opposition of German Patent No. 102013110501.7 on Dec. 21, 2018, 11 pages.
"Evidence in Support," filed with IP Australia in connection with Australian Patent Application No. 2018203659 on Nov. 8, 2019, 245 pages.
IP Australia, "Opposition—Evidence," issued in connection with Australian Patent Application No. 2018203659 on Nov. 12, 2019, 1 page.

(56) References Cited

OTHER PUBLICATIONS

"Decision Denying Institution of Inter Partes Review," issued by the United States Patent and Trademark Office in connection with Case IPR2019-01444 on Feb. 10, 2020, 16 pages.
"Summary of Opponent's Submissions," filed with IP Australia in connection with Australian Patent Application No. 2015386680 on Feb. 5, 2020, 39 pages.
EIS, Inc. v. Wow Tech International GmbH, "Defendant's Revised Motion to Dismiss EIS, Inc.'s Complaint Pursuant to Federal Rule of Civil Procedure 12(b)(6)," filed with the United States District Court for the District of Delaware in connection with Case No. 1:19-cv-01227-LPS on Feb. 4, 2020, 3 pages.
EIS, Inc. v. Wow Tech International GmbH, "Defendant's Opening Brief in Support of the Revised Motion to Dismiss Pursuant to Rule 12(b)(6)," filed with the United States District Court for the District of Delaware in connection with Case No. 1:19-cv-01227-LPS on Feb. 4, 2020, 30 pages.
EIS, Inc. v. Wow Tech International GmbH, "Plaintiff EIS's Answering Brief in Opposition to Defendant's Revised Motion to Dismiss Pursuant to Rule 12(b)(6)," filed with the United States District Court for the District of Delaware in connection with Case No. 1:19-cv-01227-LPS on Feb. 4, 2020, 33 pages.
United Stated Patent and Trademark Office, "Notice of Allowance," issued in connection with U.S. Appl. No. 15/719,085, on Feb. 3, 2020, 12 pages.
European Patent Office, "Extended European Search Report," issued in connection with European Patent Application No. EP 19161328.0, on Jul. 18, 2019, 9 pages (includes English translation of written opinion).
"Petitioner's Request for Rehearing Under 37 C.F.R. 42.71," filed with the United States Patent and Trademark Office in connection with Case IPR2019-01302 on Feb. 7, 2020, 20 pages.
"Petitioner's Amended Mandatory Notices Pursuant to 37 C.F.R. 42.8," filed with the United States Patent and Trademark Office in connection with Case IPR2019-01302 on Feb. 25, 2020, 5 pages.
"Petitioner's Amended Mandatory Notices Pursuant to 37 C.F.R. 42.8," filed with the United States Patent and Trademark Office in connection with Case IPR2019-01444 on Feb. 25, 2020, 5 pages.
"Petitioner's Request for Rehearing Under 37 C.F.R. 42.71," filed with the United States Patent and Trademark Office in connection with Case IPR2019-01444 on Mar. 6, 2020, 19 pages.
United States Patent and Trademark Office, "Notice of Allowance," issued in connection with U.S. Appl. No. 15/719,085, dated Mar. 13, 2020, 12 pages.
EIS, Inc. v. Wow Tech International GmbH, "Defendant's Reply in Support of Their Revised Motion to Dismiss Pursuant to Rule 12(b)(6)," filed with the United States District Court for the District of Delaware in connection with Case No. 1:19-cv-01227-LPS on Mar. 10, 2020, 16 pages.
Canadian Patent Office, "Notice of Allowance," issued in connection with Canadian Patent Application No. 2978739, dated Jan. 30, 2020, 1 page.
United States Patent and Trademark Office, "Notice of Allowance," issued in connection with U.S. Appl. No. 15/965,117, dated Mar. 17, 2020, 9 pages.
Canadian Patent Office, "Office Action," issued in connection with Canadian Patent Application No. 3051672, dated Mar. 4, 2020, 4 pages.
United States Patent and Trademark Office, "Notice of Allowance," issued in connection with U.S. Appl. No. 15/354,599, dated Mar. 25, 2020, 21 pages.
Korean Patent Office, "Notice of Allowance," issued in connection with Korean Patent Application No. 10-2017-7028845, dated Mar. 30, 2020, 6 pages (includes English translation).
"Order," issued by the United States Patent and Trademark Office in connection with Case IPR2019-01302 on Apr. 6, 2020, 2 pages.
"Order," issued by the United States Patent and Trademark Office in connection with Case IPR2019-01444 on Apr. 6, 2020, 2 pages.
"Decision Denying Institution of Inter Partes Review," filed with the United States Patent and Trademark Office in connection with Case IPR2020-00007 on Apr. 6, 2020, 31 pages.
United States Patent and Trademark Office, "Supplemental Notice of Allowability," issued in connection with U.S. Appl. No. 15/719,085, dated Apr. 3, 2020, 7 pages.
United States Patent and Trademark Office, "Notice of Allowance," issued in connection with U.S. Appl. No. 15/965,208, dated Apr. 8, 2020, 9 pages.
"Petition for Inter Partes Review of U.S. Pat. No. 9,937,097," filed with the United States Patent and Trademark Office on Jul. 3, 2019, 95 pages.
"Petition for Inter Partes Review of U.S. Pat. No. 9,937,097," Exhibit 1001, filed with the United States Patent and Trademark Office on Jul. 3, 2019, 18 pages.
"Petition for Inter Partes Review of U.S. Pat. No. 9,937,097," Exhibit 1002, filed with the United States Patent and Trademark Office on Jul. 3, 2019, 215 pages.
"Petition for Inter Partes Review of U.S. Pat. No. 9,937,097," Exhibit 1003, filed with the United States Patent and Trademark Office on Jul. 3, 2019, 360 pages.
"Petition for Inter Partes Review of U.S. Pat. No. 9,937,097," Exhibit 1004, filed with the United States Patent and Trademark Office on Jul. 3, 2019, 9 pages.
"Petition for Inter Partes Review of U.S. Pat. No. 9,937,097," Exhibit 1005, filed with the United States Patent and Trademark Office on Jul. 3, 2019, 34 pages.
"Petition for Inter Partes Review of U.S. Pat. No. 9,937,097," Exhibit 1006, filed with the United States Patent and Trademark Office on Jul. 3, 2019, 13 pages.
"Petition for Inter Partes Review of U.S. Pat. No. 9,937,097," Exhibit 1007, filed with the United States Patent and Trademark Office on Jul. 3, 2019, 11 pages.
"Petition for Inter Partes Review of U.S. Pat. No. 9,937,097," Exhibit 1008, filed with the United States Patent and Trademark Office on Jul. 3, 2019, 46 pages.
"Petition for Inter Partes Review of U.S. Pat. No. 9,937,097," Exhibit 1009, filed with the United States Patent and Trademark Office on Jul. 3, 2019, 1837 pages. (Uploaded in 4 parts.).
"Petition for Inter Partes Review of U.S. Pat. No. 9,937,097," Exhibit 1010, filed with the United States Patent and Trademark Office on Jul. 3, 2019, 17 pages.
"Petition for Inter Partes Review of U.S. Pat. No. 9,937,097," Exhibit 1011, filed with the United States Patent and Trademark Office on Jul. 3, 2019, 6 pages.
"Petition for Inter Partes Review of U.S. Pat. No. 9,937,097," Exhibit 1012, filed with the United States Patent and Trademark Office on Jul. 3, 2019, 47 pages.
"Petition for Inter Partes Review of U.S. Pat. No. 9,937,097," Exhibit 1013, filed with the United States Patent and Trademark Office on Jul. 3, 2019, 61 pages.
"Petition for Inter Partes Review of U.S. Pat. No. 9,937,097," Exhibit 1014, filed with the United States Patent and Trademark Office on Jul. 3, 2019, 5 pages.
"Petition for Inter Partes Review of U.S. Pat. No. 9,937,097," Exhibit 1015, filed with the United States Patent and Trademark Office on Jul. 3, 2019, 1049 pages.
United States Patent and Trademark Office, "Notice of Allowance," issued in connection with U.S. Appl. No. 15/719,085, dated on Apr. 21, 2020, 12 pages.
"Petitioner's Amended Mandatory Notices Pursuant to 37 C.F.R. 42.8," filed with the United States Patent and Trademark Office in connection with Case IPR2020-00007 on Feb. 25, 2020, 5 pages.
China National Intellectual Property Administration, "Second Office Action," issued in connection with Chinese Patent Application No. 201710927530.4, dated Apr. 16, 2020, 6 pages (English Translation Included).
United States Patent and Trademark Office, "Notice of Allowance," issued in connection with U.S. Appl. No. 15/719,085, dated May 6, 2020, 12 pages.
United States Patent and Trademark Office, "Notice of Allowance," issued in connection with U.S. Appl. No. 15/354,599, dated on May 6, 2020, 21 pages.

(56) References Cited

OTHER PUBLICATIONS

"Petitioner's Request for Rehearing Under 37 C.F.R. 42.71," filed with the United States Patent and Trademark Office in connection with Case IPR2020-00007 on May 6, 2020, 20 pages.
"Petitioner's Amended Mandatory Notices Pursuant to 37 C.F.R. 42.8," filed with the United States Patent and Trademark Office in connection with Case IPR2019-01302 on Apr. 17, 2020, 5 pages.
"Petitioner's Amended Mandatory Notices Pursuant to 37 C.F.R. 42.8," filed with the United States Patent and Trademark Office in connection with Case IPR2019-01444 on Apr. 17, 2020, 5 pages.
United States Patent and Trademark Office, "Notice of Allowance," issued in connection with U.S. Appl. No. 15/965,117, dated May 14, 2020, 9 pages.
United States Patent and Trademark Office, "Notice of Allowance," issued in connection with U.S. Appl. No. 15/965,208, dated May 15, 2020, 9 pages.
United States Patent and Trademark Office, "Supplemental Notice of Allowability," issued in connection with U.S. Appl. No. 15/719,085, dated May 12, 2020, 6 pages.
United States Patent and Trademark Office, "Supplemental Notice of Allowability," issued in connection with U.S. Appl. No. 15/719,085, dated May 27, 2020, 6 pages.
United States Patent and Trademark Office, "Corrected Notice of Allowability," issued in connection with U.S. Appl. No. 15/354,599, dated May 27, 2020, 19 pages.
United States Patent and Trademark Office, "Corrected Notice of Allowability," issued in connection with U.S. Appl. No. 15/965,117, dated Jun. 15, 2020, 3 pages.
United States Patent and Trademark Office, "Corrected Notice of Allowability," issued in connection with U.S. Appl. No. 15/965,208, mailed on Jun. 12, 2020, 11 pages.
"Decision Granting Petitioner's Request on Rehearing of Decision Denying Institution, Granting Institution of Inter Partes Review," issued by the United States Patent and Trademark Office in connection with Case IPR2019-01302 on Jun. 17, 2020, 9 pages.
*EIS, Inc.* v. *Wow Tech International GmbH*, "Notice of Supplemental Authority in Support of Plaintiff EIS Inc.'s Opposition to Defendants' Motion to Dismiss," filed with the United States District Court for the District of Delaware in connection with Case No. 1:19-cv-01227-LPS on Jun. 19, 2020, 13 pages.
*EIS, Inc.* v. *Wow Tech International GmbH*, "Defendant's Response to Plaintiff Notice of Supplemental Authority," filed with the United States District Court for the District of Delaware in connection with Case No. 1:19-cv-01227-LPS on Jun. 23, 2020, 8 pages.
*EIS GmbH* v. *USPTO*, "Complaint," filed with the United States District Court for the Eastern District of Virginia in connection with Case No. 1:20-cv-00430-LMB-TCB on Apr. 17, 2020, 636 pages.
*EIS GmbH* v. *USPTO*, "Amended Complaint," filed with the United States District Court for the Eastern District of Virginia in connection with Case No. 1:20-cv-00430-LMB-TCB on Jun. 25, 2020, 577 pages.
United States Patent and Trademark Office, "Corrected Notice of Allowability," issued in connection with U.S. Appl. No. 15/354,599, dated Jul. 13, 2020, 2 pages.
United States Patent and Trademark Office, "Corrected Notice of Allowability," issued in connection with U.S. Appl. No. 15/354,599, dated Aug. 3, 2020, 2 pages.
United States and Trademark Office, "Corrected Notice of Allowability," issued in connection with U.S. Appl. No. 15/965,117, dated Jul. 22, 2020, 3 pages.
United States Patent and Trademark Office, "Supplemental Notice of Allowability," issued in connection with U.S. Appl. No. 15/719,085, dated Jul. 27, 2020, 2 pages.
United States Patent and Trademark Office, "Corrected Notice of Allowability," issued in connection with U.S. Appl. No. 15/965,208, dated Jul. 22, 2020, 3 pages.
"Decision Granting Petitioner's Request on Rehearing of Decision Denying Institution, Granting Institution of Inter Partes Review," issued by the United States Patent and Trademark Office in connection with Case IPR2019-01444 on Aug. 11, 2020, 13 pages.

*EIS, Inc.* v. *Wow Tech International GmbH*, "Notice of Supplemental Authority in Support of Plaintiff EIS Inc.'s Opposition to Defendants' Motion to Dismiss," filed with the United States District Court for the District of Delaware in connection with Case No. 1:19-cv-01227-LPS on Aug. 14, 2020, 17 pages.
Canadian Patent Office, "Office Action," issued in connection with Canadian Patent Application No. 2978495, dated Apr. 14, 2020, 4 pages.
United States Patent and Trademark Office, "Non-Final Office Action," issued in connection with U.S. Appl. No. 16/811,907, dated Jul. 22, 2022, 30 pages.
*EIS, Inc.* v. *Wow Tech International GmbH*, "Third Amended Complaint," filed with the United States District Court for the District of Delaware in connection with Case No. 1:19-cv-01227-LPS on Sep. 16, 2021, 753 pages. (uploaded in 5 parts).
"Opposition to a European Patent, Exhibit D11" filed with the European Patent Office by Fun Factory GmbH in connection with European Patent No. EP3305266 on Feb. 11, 2021, 7 pages.
"Opposition to a European Patent, Exhibit D11a" filed with the European Patent Office by Fun Factory GmbH in connection with European Patent No. EP3305266 on Feb. 11, 2021, 18 pages (includes English translation).
"Opposition to a European Patent, Exhibit D12" filed with the European Patent Office by Fun Factory GmbH in connection with European Patent No. EP3305266 on Feb. 11, 2021, 176 pages.
"Opposition to a European Patent, Exhibit D12a" filed with the European Patent Office by Fun Factory GmbH in connection with European Patent No. EP3305266 on Feb. 11, 2021, 2 pages.
"Opposition to a European Patent, Exhibit D13" filed with the European Patent Office by Fun Factory GmbH in connection with European Patent No. EP3305266 on Feb. 11, 2021, 5 pages.
"Opposition to a European Patent, Exhibit D1a" filed with the European Patent Office by EIS GmbH in connection with European Patent No. EP3305266 on Feb. 15, 2021, 2 pages (includes English translation).
"Opposition to a European Patent, Exhibit E1" filed with the European Patent Office by EIS GmbH in connection with European Patent No. EP3305266 on Feb. 15, 2021, 3 pages (includes English translation).
"Opposition to a European Patent, Exhibit E3" filed with the European Patent Office by EIS GmbH in connection with European Patent No. EP3305266 on Feb. 15, 2021, 176 pages.
"Opposition to a European Patent, Exhibit E5" filed with the European Patent Office by EIS GmbH in connection with European Patent No. EP3305266 on Feb. 15, 2021, 152 pages.
"Opposition to a European Patent, Exhibit E6" filed with the European Patent Office by EIS GmbH in connection with European Patent No. EP3305266 on Feb. 15, 2021, 102 pages.
"Opposition to a European Patent, Exhibit E7" filed with the European Patent Office by EIS GmbH in connection with European Patent No. EP3305266 on Feb. 15, 2021, 3 pages.
"Opposition to a European Patent, Exhibit E8" filed with the European Patent Office by EIS GmbH in connection with European Patent No. EP3305266 on Feb. 15, 2021, 206 pages.
"Opposition to a European Patent, Exhibit E8a" filed with the European Patent Office by EIS GmbH in connection with European Patent No. EP3305266 on Feb. 15, 2021, 2 pages.
"Opposition to a European Patent, Exhibit E9a" filed with the European Patent Office by EIS GmbH in connection with European Patent No. EP3305266 on Feb. 15, 2021, 5 pages (includes English translation).
"Opposition to a European Patent, Exhibit E10" filed with the European Patent Office by EIS GmbH in connection with European Patent No. EP3305266 on Feb. 15, 2021, 1 page.
"Opposition to a European Patent, Exhibit E10a" filed with the European Patent Office by EIS GmbH in connection with European Patent No. EP3305266 on Feb. 15, 2021, 2 pages.
"Opposition to a European Patent, Exhibit E11" filed with the European Patent Office by EIS GmbH in connection with European Patent No. e EP3305266 on Feb. 15, 2021, 278 pages (includes English translation). (uploaded in 7 parts, each part with a corresponding translation).

(56) References Cited

OTHER PUBLICATIONS

"Opposition to a European Patent, Exhibit E11a" filed with the European Patent Office by EIS GmbH in connection with European Patent No. EP3305266 on Feb. 15, 2021, 2 pages.
"Opposition to a European Patent, Exhibit E12" filed with the European Patent Office by EIS GmbH in connection with European Patent No. EP3305266 on Feb. 15, 2021, 2 pages (includes English translation).
"Opposition to a European Patent, Exhibit E13" filed with the European Patent Office by EIS GmbH in connection with European Patent No. EP3305266 on Feb. 15, 2021, 2 pages (includes English translation).
"Opposition to a European Patent, Exhibit E14" filed with the European Patent Office by EIS GmbH in connection with European Patent No. EP3305266 on Feb. 15, 2021, 24 pages.
"Opposition to a European Patent, Exhibit E15" filed with the European Patent Office by EIS GmbH in connection with European Patent No. EP3305266 on Feb. 15, 2021, 4 pages (includes English translation).
"Opposition to a European Patent, Exhibit E16" filed with the European Patent Office by EIS GmbH in connection with European Patent No. EP3305266 on Feb. 15, 2021, 1 page.
"Opposition to a European Patent, Exhibit E17" filed with the European Patent Office by EIS GmbH in connection with European Patent No. EP3305266 on Feb. 15, 2021, 2 pages (includes English translation).
"Opposition to a European Patent, Exhibit E18" filed with the European Patent Office by EIS GmbH in connection with European Patent No. EP3305266 on Feb. 15, 2021, 1 page.
"Opposition to a European Patent, Exhibit E19" filed with the European Patent Office by EIS GmbH in connection with European Patent No. EP3305266 on Feb. 15, 2021, 3 pages.
"Opposition to a European Patent, Exhibit E20" filed with the European Patent Office by EIS GmbH in connection with European Patent No. EP3305266 on Feb. 15, 2021, 1 page.
"Opposition to a European Patent, Exhibit E21" filed with the European Patent Office by EIS GmbH in connection with European Patent No. EP3305266 on Feb. 15, 2021, 1 page.
"Opposition to a European Patent, Exhibit E21a" filed with the European Patent Office by EIS GmbH in connection with European Patent No. EP3305266 on Feb. 15, 2021, 2 pages (includes English translation).
"Opposition to a European Patent, Exhibit E22" filed with the European Patent Office by EIS GmbH in connection with European Patent No. EP3305266 on Feb. 15, 2021, 1 page.
"Opposition to a European Patent, Exhibit E22a" filed with the European Patent Office by EIS GmbH in connection with European Patent No. EP3305266 on Feb. 15, 2021, 2 pages (includes English translation).
"Opposition to a European Patent, Exhibit E23" filed with the European Patent Office by EIS GmbH in connection with European Patent No. EP3305266 on Feb. 15, 2021, 2 pages.
"Opposition to a European Patent, Exhibit E24a" filed with the European Patent Office by EIS GmbH in connection with European Patent No. EP3305266 on Feb. 15, 2021, 1 page.
"Opposition to a European Patent, Exhibit E24b" filed with the European Patent Office by EIS GmbH in connection with European Patent No. EP3305266 on Feb. 15, 2021, 1 page.
"Opposition to a European Patent, Exhibit E25" filed with the European Patent Office by EIS GmbH in connection with European Patent No. EP3305266 on Feb. 15, 2021, 3 pages (includes English translation).
"Opposition to a European Patent, Exhibit E26" filed with the European Patent Office by EIS GmbH in connection with European Patent No. EP3305266 on Feb. 15, 2021, 3 pages (includes English translation).
"Opposition to a European Patent, Exhibit E27" filed with the European Patent Office by EIS GmbH in connection with European Patent No. EP3305266 on Feb. 15, 2021, 3 pages (includes English translation).
"Opposition to a European Patent, Exhibit E28" filed with the European Patent Office by EIS GmbH in connection with European Patent No. EP3305266 on Feb. 15, 2021, 1 page.
"Opposition to a European Patent, Exhibit E29" filed with the European Patent Office by EIS GmbH in connection with European Patent No. EP3305266 on Feb. 15, 2021, 1 page.
"Opposition to a European Patent, Exhibit E30" filed with the European Patent Office by EIS GmbH in connection with European Patent No. EP3305266 on Feb. 15, 2021, 2 pages (includes English translation).
"Opposition to a European Patent, Exhibit E31a" filed with the European Patent Office by EIS GmbH in connection with European Patent No. EP3305266 on Feb. 15, 2021, 4 pages.
"Opposition to a European Patent, Exhibit E32" filed with the European Patent Office by EIS GmbH in connection with European Patent No. EP3305266 on Feb. 15, 2021, 10 pages (includes English translation).
"Opposition to a European Patent, Exhibit E33" filed with the European Patent Office by EIS GmbH in connection with European Patent No. EP3305266 on Feb. 15, 2021, 11 pages (includes English translation).
"Opposition to a European Patent, Exhibit E34" filed with the European Patent Office by EIS GmbH in connection with European Patent No. EP3305266 on Feb. 15, 2021, 6 pages (includes English translation).
"Opposition to a European Patent, Exhibit E35" filed with the European Patent Office by EIS GmbH in connection with European Patent No. EP3305266 on Feb. 15, 2021, 2 pages (includes English translation).
United States Patent and Trademark Office, "Office Action," issued in connection with U.S. Appl. No. 16/339,969, dated Dec. 21, 2021, 7 pages.
United States Patent and Trademark Office, "Notice of Allowance," issued in connection with U.S. Appl. No. 16/339,969, dated Apr. 4, 2022, 7 pages.
European Patent Office, "Extended European Search Report," issued in connection with European Application No. 17190856.9, on May 14, 2018, 30 pages. (English translation included.).
European Patent Office, "European Search Report," issued in connection with European Application No. 17190856.9, on Feb. 2, 2018, 34 pages. (English translation included.).
The International Bureau of WIPO, "International Report on Patentability," issued in connection with International Application No. PCT/EP2017/075399, on Apr. 9, 2019, 15 pages.
International Searching Authority, "Written Opinion," issued in connection with International Application No. PCT/EP2017/075399, on Apr. 25, 2018, 14 pages.
International Searching Authority, "International Search Report," issued in connection with International Application No. PCT/EP2017/075399, on Apr. 25, 2018, 9 pages. (English Translation Included.).
IP Australia, "Examination Report No. 1 for Standard Patent Application," issued in connection with Australian Application No. 2015386680, on Nov. 15, 2017, 3 pages.
IP Australia, "Examination Report No. 1 for Standard Patent Application," issued in connection with Australian Application No. 2018203659, on Dec. 14, 2018, 2 pages.
Canadian Patent Office, "Office Action," issued in connection with Canadian Application No. 2,978,495, on Nov. 20, 2017, 4 pages.
Canadian Patent Office, "Office Action," issued in connection with Canadian Application No. 2,978,495, on Apr. 11, 2018, 4 pages.
China National Intellectual Property Administration, "First Office Action," issued in connection with Chinese Application No. 201580077725.3, on Feb. 3, 2019, 5 pages (English translation included).
German Patent and Trademark Office, "Examination Report," issued in connection with German Application No. 10 2015 103 694.0, on Mar. 24, 2015, 8 pages. (English translation included.).
German Patent and Trademark Office, "Examination Report," issued in connection with German Application No. 10 2015 103 694.0, on Dec. 7, 2016, 12 pages. (English translation included.).
European Patent Office, "Extended European Search Report," issued in connection with European Patent Application No. 18175171.0, on Sep. 14, 2018, 28 pages. (English translation included.).

(56) References Cited

OTHER PUBLICATIONS

European Patent Office, "Communication Pursuant to Article 94 (3) EPC," issued in connection with European Application No. 18175171.0, on Jun. 14, 2019, 8 pages. (English translation included.).
New Zealand Intellectual Property Office, "First Examination Report," issued in connection with NZ Application No. 735229, on May 2, 2018, 4 pages.
New Zealand Intellectual Property Office, "Further Examination Report," issued in connection with NZ Application No. 735229, on Dec. 17, 2018, 3 pages.
The International Bureau of WIPO, "International Preliminary Report on Patentability," issued in connection with International Application No. PCT/EP2015/067017, on Sep. 19, 2017, 13 pages. (corresponds to English translation of Written Opinion for International Application No. PCT/EP2015/067017 dated Jul. 22, 2016, cited as NPL 6 in IDS filed on Nov. 1, 2022).
IP Australia, "Examination Report No. 1 for Standard Patent Application," issued in connection with Australian Patent Application No. 2014323661, on Mar. 2, 2017, 4 pages.
IP Australia, "Examination Report No. 1 for Standard Patent Application," issued in connection with Australian Application No. 2018200852, on Feb. 15, 2018, 5 pages.
Canadian Patent Office, "Office Action," issued in connection with Canadian Patent Application No. 2,923,526, on May 24, 2018, 5 pages.
Canadian Patent Office, "Office Action," issued in connection with Canadian Patent Application No. 2,923,526, on Oct. 16, 2018, 3 pages.
China National Intellectual Property Administration, "First Office Action," issued in connection with Chinese Patent Application No. 201480052194.8, on Sep. 28, 2016, 7 pages. (English Translation Included.).
China National Intellectual Property Administration, "Second Office Action," issued in connection with Chinese Patent Application No. 201480052194.8, on Jan. 3, 2017, 10 pages. (English Translation Included.).
China National Intellectual Property Administration, "Third Office Action," issued in connection with Chinese Patent Application No. 201480052194.8, on Jul. 4, 2017, 11 pages. (English Translation Included.).
China National Intellectual Property Administration, "First Office Action," issued in connection with Chinese Patent Application No. 201710709587.7, on Feb. 28, 2019, 5 pages. (English Translation Included.).
German Patent and Trademark Office, "Office Action," issued in connection with German Patent Application No. 10 2013 110 501.7, on Oct. 1, 2013, 8 pages. (English translation included.).
German Patent and Trademark Office, "Office Action," issued in connection with German Patent Application No. 10 2013 110 501.7, on Apr. 15, 2014, 8 pages. (English translation included.).
German Patent and Trademark Office, "Office Action," issued in connection with German Patent Application No. 10 2013 110 501.7, on Feb. 6, 2015, 10 pages. (English translation included.).
German Patent and Trademark Office, "Office Action," issued in connection with German Patent Application No. 10 2013 110 501.7, on Nov. 18, 2015, 8 pages. (English translation included.).
German Patent and Trademark Office, "Office Action," issued in connection with German Patent Application No. 10 2013 022 511.6, on May 9, 2019, 16 pages. (English translation included.).
German Patent and Trademark Office, "Office Action," issued in connection with German Patent Application No. 10 2013 022 512.4, on May 3, 2019, 14 pages. (English translation included.).
German Patent and Trademark Office, "Office Action," issued in connection with German Patent Application No. 10 2013 022 520.5, on May 9, 2019, 14 pages. (English translation included.).
European Patent Office, "Communication Pursuant to Article 94 (3) EPC," issued in connection with European Application No. 14741640.8, on Aug. 23, 2016, 8 pages. (English translation included.).
European Patent Office, "Communication Pursuant to Article 94 (3) EPC," issued in connection with European Application No. 14741640.8, on Mar. 8, 2018, 12 pages. (English translation included.).
European Patent Office, "Communication Pursuant to Article 94 (3) EPC," issued in connection with European Application No. 17202385.5, on May 18, 2018, 12 pages. (English translation included.).
European Patent Office, "Result of the Consultation" issued in connection with European Application No. 17202385.5, on Jul. 18, 2018, 6 pages. (English translation included.).
European Patent Office, "Search Report," issued in connection with European Application No. 17202385.5, on Mar. 8, 2018, 6 pages. (English translation included.).
European Patent Office, "Communication Pursuant to Article 94 (3) EPC," issued in connection with European Application No. 17202394.7, on May 18, 2018, 12 pages. (English translation included.).
European Patent Office, "Result of the Consultation" issued in connection with European Application No. 17202394.7, on Jul. 18, 2018, 6 pages. (English translation included.).
European Patent Office, "Search Report," issued in connection with European Application No. 17202394.7, on Mar. 8, 2018, 8 pages. (English translation included.).
European Patent Office, "Communication Pursuant to Article 94 (3) EPC," issued in connection with European Application No. 18206800.7, on Apr. 8, 2019, 10 pages. (English translation included.).
European Patent Office, "Search Report," issued in connection with European Application No. 18206800.7, on Feb. 27, 2019, 8 pages. (English translation included.).
International Searching Authority, "Written Opinion of the International Searching Authority," issued in connection with International Application No. PCT/EP2014/065734, on Sep. 25, 2014, 19 pages. (English Translation Included.).
The International Bureau of WIPO, "International Preliminary Report on Patentability," issued in connection with International Application No. PCT/EP2014/065734, on Mar. 29, 2016, 7 pages. (corresponds to English translation of Written Opinion for International Application No. PCT/EP2014/065734 dated Sep. 25, 2014, cited herein as NPL43).
United States Patent and Trademark Office, "Notice of Allowance and Fee(s) Due," issued in connection with Design U.S. Appl. No. 29/590,450, on May 8, 2018, 7 pages.
United States Patent and Trademark Office, "Notice of Allowance and Fee(s) Due," issued in connection with Design U.S. Appl. No. 35/502,986, on May 1, 2018, 9 pages.
United Stated Patent and Trademark Office, "Notice of Allowance and Fee(s) Due," issued in connection with U.S. Appl. No. 15/719,085, on Jul. 3, 2019, 12 pages.
European Patent Office, "Examination Report," issued in connection with application No. 15748202.7 on Jun. 24, 2019, 8 pages (English translation included).
"Petition for Inter Partes Review of U.S. Pat. No. 9,763,851," filed with the United States Patent and Trademark Office on Jul. 31, 2019, 87 pages.
"Petition for Inter Partes Review of U.S. Pat. No. 9,763,851," Exhibit 1001, filed with the United States Patent and Trademark Office on Jul. 31, 2019, 17 pages.
"Petition for Inter Partes Review of U.S. Pat. No. 9,763,851," Exhibit 1002, filed with the United States Patent and Trademark Office on Jul. 31, 2019, 109 pages.
"Petition for Inter Partes Review of U.S. Pat. No. 9,763,851," Exhibit 1003 Part 1, filed with the United States Patent and Trademark Office on Jul. 31, 2019, 649 pages.
"Petition for Inter Partes Review of U.S. Pat. No. 9,763,851," Exhibit 1003 Part 2, filed with the United States Patent and Trademark Office on Jul. 31, 2019, 663 pages.
"Petition for Inter Partes Review of U.S. Pat. No. 9,763,851," Exhibit 1004, filed with the United States Patent and Trademark Office on Jul. 31, 2019, 11 pages.
"Petition for Inter Partes Review of U.S. Pat. No. 9,763,851," Exhibit 1005, filed with the United States Patent and Trademark Office on Jul. 31, 2019, 34 pages.
"Petition for Inter Partes Review of U.S. Pat. No. 9,763,851," Exhibit 1006, filed with the United States Patent and Trademark Office on Jul. 31, 2019, 46 pages.

(56) References Cited

OTHER PUBLICATIONS

"Petition for Inter Partes Review of U.S. Pat. No. 9,763,851," Exhibit 1007, filed with the United States Patent and Trademark Office on Jul. 31, 2019, 36 pages.
"Petition for Inter Partes Review of U.S. Pat. No. 9,763,851," Exhibit 1008, filed with the United States Patent and Trademark Office on Jul. 31, 2019, 46 pages.
"Petition for Inter Partes Review of U.S. Pat. No. 9,763,851," Exhibit 1009, filed with the United States Patent and Trademark Office on Jul. 31, 2019, 5 pages.
"Petition for Inter Partes Review of U.S. Pat. No. 9,763,851," Exhibit 1010, filed with the United States Patent and Trademark Office on Jul. 31, 2019, 61 pages.
"Petition for Inter Partes Review of U.S. Pat. No. 9,763,851," Exhibit 1011, filed with the United States Patent and Trademark Office on Jul. 31, 2019, 6 pages.
"Petition for Inter Partes Review of U.S. Pat. No. 9,763,851," Exhibit 1012, filed with the United States Patent and Trademark Office on Jul. 31, 2019, 1049 pages. (Uploaded in 3 parts.).
United States Patent and Trademark Office, "Non-Final Office Action," issued in connection with U.S. Appl. No. 15/965,208, on Aug. 22, 2019, 17 pages.
United States Patent and Trademark Office, "Notice of Allowance and Fee(s) Due," issued in connection with U.S. Appl. No. 15/354,599, on Aug. 29, 2019, 19 pages.
IP Australia, "Notice of Opposition," issued in connection with Australian Patent Application No. 2015386680 on Jun. 21, 2018, 4 pages.
"Opponent's Letter," filed with IP Australia in connection with Australian Patent Application No. 2015386680 on Jun. 28, 2019, 10 pages.
IP Australia, "General Correspondence," issued in connection with Australian Patent Application No. 2015386680 on Jul. 24, 2019, 2 pages.
"Opponent's Letter," filed with IP Australia in connection with Australian Patent Application No. 2015386680 on Aug. 7, 2019, 2 pages.
IP Australia, "Reg. 5.23," issued in connection with Australian Patent Application No. 2015386680 on Aug. 16, 2019, 4 pages.
"Statement of Grounds and Particulars of Opposition," filed with IP Australia in connection with Australian Patent Application No. 201803659 on Aug. 14, 2019, 15 pages.
"Exhibit D1," filed with IP Australia in connection with Australian Patent Application No. 2018203659 on Aug. 14, 2019, 9 pages.
"Exhibit D2," filed with IP Australia in connection with Australian Patent Application No. 2018203659 on Aug. 14, 2019, 9 pages.
"Exhibit D3," filed with IP Australia in connection with Australian Patent Application No. 2018203659 on Aug. 14, 2019, 51 pages.
"Exhibit D4," filed with IP Australia in connection with Australian Patent Application No. 2018203659 on Aug. 14, 2019, 6 pages.
"Exhibit D5," filed with IP Australia in connection with Australian Patent Application No. 2018203659 on Aug. 14, 2019, 5 pages.
"Exhibit D6," filed with IP Australia in connection with Australian Patent Application No. 2018203659 on Aug. 14, 2019, 3 pages.
"Exhibit D7," filed with IP Australia in connection with Australian Patent Application No. 2018203659 on Aug. 14, 2019, 28 pages.
"Exhibit D8," filed with IP Australia in connection with Australian Patent Application No. 2018203659 on Aug. 14, 2019, 8 pages.
"Exhibit D9," filed with IP Australia in connection with Australian Patent Application No. 2018203659 on Aug. 14, 2019, 11 pages.
"Exhibit D10," filed with IP Australia in connection with Australian Patent Application No. 2018203659 on Aug. 14, 2019, 33 pages.
"Exhibit D11," filed with IP Australia in connection with Australian Patent Application No. 2018203659 on Aug. 14, 2019, 2 pages.
"Exhibit D12," filed with IP Australia in connection with Australian Patent Application No. 2018203659 on Aug. 14, 2019, 9 pages.
IP Australia, "Opposition—Statement or Grounds and Particulars," issued in connection with Australian Patent Application No. 2018203659 on Aug. 15, 2019, 1 page.

"Preliminary Court Opinion," issued by the German Federal Patent Court in connection with appeal regarding German Patent No. 102013110501.7 on Dec. 14, 2022, 46 pages (includes English translation).
"Minutes of Oral Proceeding," issued by the German Federal Patent Court in connection with appeal regarding German Patent No. 102013110501.7 on Jan. 31, 2023, 9 pages (includes English translation).
European Patent Office, Board of Appeals, "Oral Proceedings: Minutes," issued in connection with opposition of European Patent No. EP2976057 on May 24, 2023, 14 pages (includes English translation).
European Patent Office, Board of Appeals, "Oral Proceedings: Minutes," issued in connection with opposition of European Patent No. EP3308762 on May 24, 2023, 16 pages (includes English translation).
*EIS Inc.* v. *IntiHealth Ger GmbH et al.*, "Official Transcript of Markman Hearing Held on Nov. 21, 2022," issued on Nov. 29, 2022, in connection with Case No. 1:19-cv-1227-GBW before the United States District Court for the District of Delaware, 208 pages.
*EIS Inc.* v. *IntiHealth Ger GmbH et al.*, "Memorandum Opinion," issued by the United States District Court for the District of Delaware in connection with Case No. 1:19-cv-1227-GBW on Jan. 9, 2023, 47 pages.
*EIS Inc.* v. *IntiHealth Ger GmbH et al.*, "Defendants' Reply In Support Of Its Motion For Leave To File Early Motion For Partial Summary Judgment," filed with the United States District Court for the District of Delaware in connection with Case No. 1:19-cv-1227-GBW on Jan. 17, 2023, 6 pages.
*EIS Inc.* v. *IntiHealth Ger GmbH et al.*, "Plaintiff And Counterclaim-Defendants' Motion To Strike Untimely Doctrine Of Equivalents Allegations," filed with the United States District Court for the District of Delaware in connection with Case No. 1:19-cv-1227-GBW on Mar. 6, 2023, 3 pages.
*EIS Inc.* v. *IntiHealth Ger GmbH et al.*, "Letter To The Honorable Gregory B. Williams Regarding Counterclaim-Defendants' Motion To Strike Untimely Doctrine Of Equivalents Allegations," filed with the United States District Court for the District of Delaware in connection with Case No. 1:19-cv-1227-GBW on Mar. 6, 2023, 25 pages.
*EIS Inc.* v. *IntiHealth Ger GmbH et al.*, "Defendant/Counterclaimant Novoluto Gmbh's Motion To Strike Plaintiff And Counterclaim-Defendants' Election Of Prior-Art-Based Invalidity Arguments Pursuant To IPR Estoppel, 35 U.S.C. § 315(E)(2)," filed with the United States District Court for the District of Delaware in connection with Case No. 1:19-cv-1227-GBW on Mar. 9, 2023, 3 pages.
*EIS Inc.* v. *IntiHealth Ger GmbH et al.*, "Letter to The Honorable Gregory B. Williams from Paul D. Brown Regarding Defendant and Counterclaimant Novoluto GmbH's Motion to Strike Plaintiff's and Counterclaim—Defendants' Election of Prior-Art-Based Invalidity Arguments Pursuant To IPR Estoppel, 35 U.S.C. § 315(E)(2)," filed with the United States District Court for the District of Delaware in connection with Case No. 1:19-cv-1227-GBW on Mar. 9, 2023, 640 pages.
*EIS Inc.* v. *IntiHealth Ger GmbH et al.*, "Letter to The Honorable Gregory B. Williams from Paul D. Brown Regarding Response to Counterclaim Defendants' Motion to Strike Doctrine of Equivalents Allegations," filed with the United States District Court for the District of Delaware in connection with Case No. 1:19-cv-1227-GBW on Mar. 13, 2023, 2 pages.
*EIS Inc.* v. *IntiHealth Ger GmbH et al.*, "Letter to The Honorable Gregory B. Williams from Jack B. Blumenfeld Regarding Opposition to Defendants' Motion to Strike EIS's Election of Prior-Art-Based Invalidity Arguments," filed with the United States District Court for the District of Delaware in connection with Case No. 1:19-cv-1227-GBW on Mar. 20, 2023, 16 pages.
*EIS Inc.* v. *IntiHealth Ger GmbH et al.*, "Letter to The Honorable Gregory B. Williams from Gregory E. Stuhlman, Esquire Regarding Reply Letter Regarding Defendant-Counterclaimant Novoluto GmbH's Motion to Strike Plaintiff's and Counterclaim-Defendants' Election of Prior-Art-Based Invalidity Arguments Pursuant to IPR Estoppel,"

(56) References Cited

OTHER PUBLICATIONS filed with the United States District Court for the District of Delaware in connection with Case No. 1:19-cv-1227-GBW on Mar. 21, 2023, 9 pages.

*EIS Inc.* v. *IntiHealth Ger GmbH et al.*, "Letter to The Honorable Gregory B. Williams from Jack B. Blumenfeld Regarding Response to the Court's Oral Order," filed with the United States District Court for the District of Delaware in connection with Case No. 1:19-cv-1227-GBW on Mar. 30, 2023, 1 page.

*EIS Inc.* v. *IntiHealth Ger GmbH et al.*, "Letter to The Honorable Gregory B. Williams from Jack B. Blumenfeld Regarding Discovery Dispute (Redacted Public Version)," filed with the United States District Court for the District of Delaware in connection with Case No. 1:19-cv-1227-GBW on Apr. 6, 2023 (redacted version filed Apr. 13, 2023), 433 pages (uploaded in 4 parts).

*EIS Inc.* v. *IntiHealth Ger GmbH et al.*, "Defendant-Counterclaimant Novoluto's Reply Letter to The Honorable Gregory B. Williams Regarding Alleged Privilege Waiver by Defendants," filed with the United States District Court for the District of Delaware in connection with Case No. 1:19-cv-1227-GBW on Apr. 12, 2023, 4 pages.

*Novoluto GmbH* v. *Uccellini LLC*, "Motion for Entry of Default and for Leave to Move for Default Judgment Pursuant to Fed. R. Civ. P. 55(b)(2)," filed with the United States District Court for the District of Oregon in connection with Case No. 6:20-cv-02284-MK on Mar. 15, 2023, 5 pages.

*Novoluto GmbH* v. *Uccellini LLC*, "Declaration of Tammy J. Terry in Support of Motion for Entry of Default and for Leave to Move for Default Judgment," filed with the United States District Court for the District of Oregon in connection with Case No. 6:20-cv-02284-MK on Mar. 15, 2023, 3 pages.

"Judgment," issued by the United States Court of Appeals for the Federal Circuit in connection with cases 2021-2215, 2022-1020, and 2022-1191 (Consolidated Appeal from the United States Patent and Trademark Office, Patent Trial and Appeal Board of Inter Partes Review Nos. IPR2019-01302, IPR2019-01444, and IPR2020-00007) on Mar. 13, 2023, 2 pages.

United States Patent and Trademark Office, "Notice of Allowance," issued in connection with U.S. Appl. No. 16/339,969, dated Dec. 8, 2022, 7 pages.

United States Patent and Trademark Office, "Notice of Allowance," issued in connection with U.S. Appl. No. 15/888,568, dated Jan. 18, 2023, 8 pages.

United States Patent and Trademark Office, "Non-Final Office Action," issued in connection with U.S. Appl. No. 17/029,974, dated Feb. 28, 2023, 100 pages.

United States Patent and Trademark Office, "Non-Final Office Action," issued in connection with U.S. Appl. No. 17/403,609, dated Mar. 16, 2023, 6 pages.

United States Patent and Trademark Office, "Non-Final Office Action," issued in connection with U.S. Appl. No. 17/461,470, dated Mar. 16, 2023, 6 pages.

United States Patent and Trademark Office, "Final Office Action," issued in connection with U.S. Appl. No. 16/811,907, dated Apr. 7, 2023, 32 pages.

United States Patent and Trademark Office, "Non-Final Office Action," issued in connection with U.S. Appl. No. 16/339,969, dated Apr. 12, 2023, 12 pages.

"Grounds on Appeal," issued by the German Federal Patent Court in connection with appeal regarding German Patent No. 102013110501.7 on May 22, 2023, 67 pages (includes English translation).

European Patent Office, Board of Appeals, "Decision of May 16, 2023," issued in connection with opposition of European Patent No. EP2976057 on Jun. 21, 2023, 46 pages (includes English translation).

European Patent Office, Board of Appeals, "Decision of May 16, 2023," issued in connection with opposition of European Patent No. EP3308762 on Jun. 21, 2023, 48 pages (includes English translation).

*EIS Inc.* v. *IntiHealth Ger GmbH et al.*, "Plaintiff EIS, Inc.'s Notice Of Subsequent Authority In Support Of Its Opposition To Defendants' Motion To Strike EIS's Election Of Prior-Art Based Invalidity Arguments (Redacted Public Version)," filed with the United States District Court for the District of Delaware in connection with Case No. 1:19-cv-1227-GBW on May 11, 2023, 1,179 pages (uploaded in 6 parts).

*EIS Inc.* v. *IntiHealth Ger GmbH et al.*, "Letter To The Honorable Gregory B. Williams Regarding Counterclaim-Defendants' Motion To Strike Untimely Discovery And Expert Disclosures (Redacted Public Version)," filed with the United States District Court for the District of Delaware in connection with Case No. 1:19-cv-1227-GBW on May 16, 2023, 173 pages.

*EIS Inc.* v. *IntiHealth Ger GmbH et al.*, "Plaintiff's And Counterclaim Defendants' Opening Brief In Support Of Their Daubert Motion To Exclude Opinions Of Robert L. Stoll (Redacted Public Version)," filed with the United States District Court for the District of Delaware in connection with Case No. 1:19-cv-1227-GBW on May 17, 2023, 16 pages.

*EIS Inc.* v. *IntiHealth Ger GmbH et al.*, "Declaration Of Allan M. Soobert In Support Of Plaintiff's And Counterclaim Defendants' Daubert Motion To Exclude Opinions Of Robert L. Stoll (Redacted Public Version)," filed with the United States District Court for the District of Delaware in connection with Case No. 1:19-cv-1227-GBW on May 17, 2023, 111 pages.

*EIS Inc.* v. *IntiHealth Ger GmbH et al.*, "Plaintiff's And Counterclaim Defendants' Opening Brief In Support Of Their Daubert Motion To Exclude Certain "Stimulation Device" Opinions (Public Version)," filed with the United States District Court for the District of Delaware in connection with Case No. 1:19-cv-1227-GBW on May 19, 2023, 9 pages.

*EIS Inc.* v. *IntiHealth Ger GmbH et al.*, "Declaration Of Allan M. Soobert In Support Of Plaintiff's And Counterclaim Defendants' Opening Brief In Support Of Their Daubert Motion To Exclude Certain "Stimulation Device" Opinions (Public Version)," filed with the United States District Court for the District of Delaware in connection with Case No. 1:19-cv-1227-GBW on May 19, 2023, 498 pages (uploaded in 2 parts).

*EIS Inc.* v. *IntiHealth Ger GmbH et al.*, "Plaintiff's And Counterclaim Defendants' Opening Brief In Support Of Their Daubert Motion To Exclude Certain Opinions Of Drs. Cameron And Herbenick (Public Version)," filed with the United States District Court for the District of Delaware in connection with Case No. 1:19-cv-1227-GBW on May 19, 2023, 9 pages.

*EIS Inc.* v. *IntiHealth Ger GmbH et al.*, "Declaration Of Allan M. Soobert In Support Of Plaintiff's And Counterclaim Defendants' Daubert Motion To Exclude Certain Opinions Of Drs. Cameron And Herbenick (Public Version)," filed with the United States District Court for the District of Delaware in connection with Case No. 1:19-cv-1227-GBW on May 19, 2023, 125 pages (uploaded in 2 parts).

*EIS Inc.* v. *IntiHealth Ger GmbH et al.*, "Plaintiff's And Counterclaim Defendants' Opening Brief In Support Of Their Daubert Motion To Exclude The Opinions Of Dr. Debra Herbenick (Public Version)," filed with the United States District Court for the District of Delaware in connection with Case No. 1:19-cv-1227-GBW on May 19, 2023, 8 pages.

*EIS Inc.* v. *IntiHealth Ger GmbH et al.*, "Declaration Of Allan M. Soobert In Support Of Plaintiff's And Counterclaim Defendants' Daubert Motion To Exclude The Opinions Of Dr. Debra Herbenick (Public Version)," filed with the United States District Court for the District of Delaware in connection with Case No. 1:19-cv-1227-GBW on May 19, 2023, 697 pages (uploaded in 3 parts).

*EIS Inc.* v. *IntiHealth Ger GmbH et al.*, "Plaintiff's And Counterclaim Defendants' Brief In Support Of Motion No. 2 For Partial Summary Judgment That The Asserted Claims Of U.S. Pat. Nos. 11,090,220, 11,103,418, 9,937,097 Are Not Entitled To An Effective Filing Date Of Their Respective Earliest U.S. Parent Patents (Public Version)," filed with the United States District Court for the District of Delaware in connection with Case No. 1:19-cv-1227-GBW on May 19, 2023, 10 pages.

*EIS Inc.* v. *IntiHealth Ger GmbH et al.*, "Declaration Of Allan M. Soobert In Support Of Plaintiff's And Counterclaim Defendants'

(56) References Cited

OTHER PUBLICATIONS

Motion No. 2 For Partial Summary Judgment That The Asserted Claims Of U.S. Pat. Nos. 11,090,220, 11,103,418, 9,937,097 Are Not Entitled To An Effective Filing Date Of Their Respective Earliest U.S. Parent Patents (Public Version)," filed with the United States District Court for the District of Delaware in connection with Case No. 1:19-cv-1227-GBW on May 19, 2023, 274 pages (uploaded in 2 parts).
EIS Inc. v. IntiHealth Ger GmbH et al., "Plaintiff's And Counterclaim Defendants' Concise Statement Of Facts In Support Of Motion No. 2 For Partial Summary Judgment That The Asserted Claims Of U.S. Pat. Nos. 11,090,220, 11,103,418, 9,937,097 Are Not Entitled To An Effective Filing Date Of Their Respective Earliest U.S. Parent Patents (Public Version)," filed with the United States District Court for the District of Delaware in connection with Case No. 1:19-cv-1227-GBW on May 19, 2023, 8 pages.
EIS Inc. v. IntiHealth Ger GmbH et al., "Plaintiff's And Counterclaim Defendants' Brief In Support Of Motion No. 4 For Partial Summary Judgment Of Noninfringement Of All Asserted Claims Of U.S. Pat. No. 9,763,851 (Public Version)," filed with the United States District Court for the District of Delaware in connection with Case No. 1:19-cv-1227-GBW on May 19, 2023, 10 pages.
EIS Inc. v. IntiHealth Ger GmbH et al., "Declaration Of Allan M. Soobert In Support Of Plaintiff's And Counterclaim Defendants' Motion No. 4 For Partial Summary Judgment Of Noninfringement Of All Asserted Claims Of U.S. Pat. No. 9,763,851 (Public Version)," filed with the United States District Court for the District of Delaware in connection with Case No. 1:19-cv-1227-GBW on May 19, 2023, 182 pages (uploaded in 3 parts).
EIS Inc. v. IntiHealth Ger GmbH et al., "Plaintiff's Concise Statement Of Facts In Support Of Motion No. 4 For Partial Summary Judgment Of Noninfringement Of All Asserted Claims Of U.S. Pat. No. 9,763,851 (Public Version)," filed with the United States District Court for the District of Delaware in connection with Case No. 1:19-cv-1227-GBW on May 19, 2023, 8 pages.
EIS Inc. v. IntiHealth Ger GmbH et al., "Plaintiff's And Counterclaim Defendants' Brief In Support Of Their Motion No. 5 For Partial Summary Judgment Of Invalidity Of The Asserted Claims Of U.S. Pat. Nos. 11,090,220 And 11,103,418 (Public Version)," filed with the United States District Court for the District of Delaware in connection with Case No. 1:19-cv-1227-GBW on May 19, 2023, 6 pages.
EIS Inc. v. IntiHealth Ger GmbH et al., "Declaration Of Allan M. Soobert In Support Of Plaintiff's And Counterclaim Defendants' Motion No. 5 For Partial Summary Of Invalidity Of The Asserted Claims Of U.S. Pat. Nos. 11,090,220 And 11,103,418 (Public Version)," filed with the United States District Court for the District of Delaware in connection with Case No. 1:19-cv-1227-GBW on May 19, 2023, 168 pages (uploaded in 2 parts).
EIS Inc. v. IntiHealth Ger GmbH et al., "Plaintiff's And Counterclaim Defendants' Concise Statement Of Facts In Support Of Their Motion No. 5 For Partial Summary Judgment Of Invalidity Of The Asserted Claims Of U.S. Pat. Nos. 11,090,220 And 11,103,418 (Public Version)," filed with the United States District Court for the District of Delaware in connection with Case No. 1:19-cv-1227-GBW on May 19, 2023, 4 pages.
EIS Inc. v. IntiHealth Ger GmbH et al., "Reply Letter To The Honorable Gregory B. Williams In Support Of Counterclaim-Defendants' Motion To Strike Untimely Discovery And Expert Disclosures," filed with the United States District Court for the District of Delaware in connection with Case No. 1:19-cv-1227-GBW on May 19, 2023, 28 pages.
United States Patent and Trademark Office, "Notice of Allowance," issued in connection with U.S. Appl. No. 15/888,568, dated Aug. 26, 2022, 8 pages.
"Brief for Appellant EIS GmbH" filed with the United States Court of Appeals for the Federal Circuit in connection with cases 2021-2215, 2022-1020, and 2022-1191 (Consolidated Appeal from the United States Patent and Trademark Office, Patent Trial and Appeal Board in Nos. IPR2019-01302, IPR2019-01444, and IPR2020-00007), filed Apr. 25, 2022, 321 pages (uploaded in 3 parts).
"Brief of Appellee Novoluto GmbH," filed with the United States Court of Appeals for the Federal Circuit in connection with cases 2021-2215, 2022-1020, and 2022-1191 (Consolidated Appeal from the United States Patent and Trademark Office, Patent Trial and Appeal Board of Inter Partes Review Nos. IPR2019-01302, IPR2019-01444, and IPR2020-00007), filed Jun. 21, 2022, 52 pages.
"Appellant's Reply Brief," filed with the United States Court of Appeals for the Federal Circuit in connection with cases 2021-2215, 2022-1020, and 2022-1191 (Consolidated Appeal from the United States Patent and Trademark Office, Patent Trial and Appeal Board of Inter Partes Review Nos. IPR2019-01302, IPR2019-01444, and IPR2020-00007), filed Aug. 2, 2022, 26 pages.
"Joint Appendix, vol. I of II," filed with the United States Court of Appeals for the Federal Circuit in connection with cases 2021-2215, 2022-1020, and 2022-1191 (Consolidated Appeal from the United States Patent and Trademark Office, Patent Trial and Appeal Board of Inter Partes Review Nos. IPR2019-01302, IPR2019-01444, and IPR2020-00007), filed Aug. 9, 2022, 674 pages (uploaded in 9 parts).
"Joint Appendix, vol. II of II," filed with the United States Court of Appeals for the Federal Circuit in connection with cases 2021-2215, 2022-1020, and 2022-1191 (Consolidated Appeal from the United States Patent and Trademark Office, Patent Trial and Appeal Board of Inter Partes Review Nos. IPR2019-01302, IPR2019-01444, and IPR2020-00007), filed Aug. 9, 2022, 682 pages (uploaded in 9 parts).
United States Patent and Trademark Office, "Office Communication Concerning Third Party Submission Under 37 C.F.R. § 1.290," issued in connection with U.S. Appl. No. 17/029,974, dated May 23, 2022, 19 pages.
EIS Inc. v. IntiHealth Ger GmbH et al., "Joint Claim Construction Brief (Redacted—Public Version)," filed with the United States District Court for the District of Delaware in connection with Case No. 1:19-cv-1227-VAC-MPT on Jul. 7, 2022, 101 pages.
EIS Inc. v. IntiHealth Ger GmbH et al., "Appendix to Joint Claim Construction Brief, vol. 1 of 2, Exhibits 12, 13, 15-20, and 22-50," filed with the United States District Court for the District of Delaware in connection with Case No. 1:19-cv-1227-VAC-MPT on Jun. 30, 2022, 869 pages (uploaded in 3 parts).
EIS Inc. v. IntiHealth Ger GmbH et al., "Appendix to Joint Claim Construction Brief, vol. 2 of 2, Exhibits 51-41," filed with the United States District Court for the District of Delaware in connection with Case No. 1:19-cv-1227-VAC-MPT on Jun. 30, 2022, 261 pages.
EIS Inc. v. IntiHealth Ger GmbH et al., "Exhibits 14 and 21 to Appendix Joint Claim Construction Brief (Redacted—Public Version)," filed with the United States District Court for the District of Delaware in connection with Case No. 1:19-cv-1227-VAC-MPT on Jul. 7, 2022, 25 pages.
EIS Inc. v. IntiHealth Ger GmbH et al., "Plaintiff and Counterclaim-Defendants' Comments and Objections on Novoluto's Technology Tutorial," filed with the United States District Court for the District of Delaware in connection with Case No. 1:19-cv-1227-VAC-MPT on Jun. 30, 2022, 8 pages.
"Complaint Response," filed with the German Patent and Trademark in connection with opposition of German Patent No. 102013110501.7 on Apr. 14, 2022, 71 pages (includes English translation).
"Complaint Response, Exhibit ES2," filed with the German Patent and Trademark in connection with opposition of German Patent No. 102013110501.7 on Apr. 14, 2022, 82 pages.
"Accession of the Alleged Patent Infringer According to Art. 105 EPC," filed with the European Patent Office by Triple A Sales GmBH in connection with European Patent No. EP2976057 on May 3, 2022, 86 pages (includes English translation).
"Accession of the Alleged Patent Infringer According to Art. 105 EPC, Exhibit B1," filed with the European Patent Office by Triple A Sales GmBH in connection with European Patent No. EP2976057 on May 3, 2022, 16 pages (includes English translation).
"Accession of the Alleged Patent Infringer According to Art. 105 EPC, Exhibit B2," filed with the European Patent Office by Triple

(56) References Cited

OTHER PUBLICATIONS

A Sales GmBH in connection with European Patent No. EP2976057 on May 3, 2022, 4 pages (includes English translation).
"Accession of the Alleged Patent Infringer According to Art. 105 EPC, Exhibit B3," filed with the European Patent Office by Triple A Sales GmBH in connection with European Patent No. EP2976057 on May 3, 2022, 12 pages (includes English translation).
"Accession of the Alleged Patent Infringer According to Art. 105 EPC, Exhibit B4," filed with the European Patent Office by Triple A Sales GmBH in connection with European Patent No. EP2976057 on May 3, 2022, 1 page.
"Accession of the Alleged Patent Infringer According to Art. 105 EPC, Exhibit B5," filed with the European Patent Office by Triple A Sales GmBH in connection with European Patent No. EP2976057 on May 3, 2022, 2 pages (includes English translation).
"Accession of the Alleged Patent Infringer According to Art. 105 EPC, Exhibit 50," filed with the European Patent Office by Triple A Sales GmBH in connection with European Patent No. EP2976057 on May 3, 2022, 24 pages.
"Accession of the Alleged Patent Infringer According to Art. 105 EPC, Exhibit 50A," filed with the European Patent Office by Triple A Sales GmBH in connection with European Patent No. EP2976057 on May 3, 2022, 24 pages.
"Accession of the Alleged Patent Infringer According to Art. 105 EPC, Exhibit 51," filed with the European Patent Office by Triple A Sales GmBH in connection with European Patent No. EP2976057 on May 3, 2022, 18 pages (includes English translation).
"Accession of the Alleged Patent Infringer According to Art. 105 EPC," filed with the European Patent Office by Triple A Sales GmBH in connection with European Patent No. 3308762 on May 3, 2022, 82 pages (includes English translation).
"Accession of the Alleged Patent Infringer According to Art. 105 EPC, Exhibit B1," filed with the European Patent Office by Triple A Sales GmBH in connection with European Patent No. EP3308762 on May 3, 2022, 16 pages (includes English translation).
"Accession of the Alleged Patent Infringer According to Art. 105 EPC, Exhibit B2," filed with the European Patent Office by Triple A Sales GmBH in connection with European Patent No. EP3308762 on May 3, 2022, 4 pages (includes English translation).
"Accession of the Alleged Patent Infringer According to Art. 105 EPC, Exhibit B3," filed with the European Patent Office by Triple A Sales GmBH in connection with European Patent No. EP3308762 on May 3, 2022, 12 pages (includes English translation).
"Accession of the Alleged Patent Infringer According to Art. 105 EPC, Exhibit B4," filed with the European Patent Office by Triple A Sales GmBH in connection with European Patent No. EP3308762 on May 3, 2022, 1 page.
"Accession of the Alleged Patent Infringer According to Art. 105 EPC, Exhibit B5," filed with the European Patent Office by Triple A Sales GmBH in connection with European Patent No. EP3308762 on May 3, 2022, 2 pages (includes English translation).
"Accession of the Alleged Patent Infringer According to Art. 105 EPC, Exhibit 43," filed with the European Patent Office by Triple A Sales GmBH in connection with European Patent No. EP3308762 on May 3, 2022, 24 pages.
"Accession of the Alleged Patent Infringer According to Art. 105 EPC, Exhibit 43A," filed with the European Patent Office by Triple A Sales GmBH in connection with European Patent No. EP3308762 on May 3, 2022, 24 pages.
"Accession of the Alleged Patent Infringer According to Art. 105 EPC, Exhibit 44," filed with the European Patent Office by Triple A Sales GmBH in connection with European Patent No. EP3308762 on May 3, 2022, 12 pages.
"Appeal Letter," filed with the European Patent Office by Novoluto GmBH in connection with European Patent No. EP2976057 on Jul. 20, 2022, 148 pages (includes English translation).
"Appeal Letter," filed with the European Patent Office by Novoluto GmBH in connection with European Patent No. EP3308762 on Jul. 20, 2022, 148 pages (includes English translation).

Chinese National Intellectual Property Adminstration, "Fourth Office Action," issued in connection with Chinese Patent Application No. 201480052194.8, dated Oct. 10, 2022, 17 pages (includes English translation).
United States Patent and Trademark Office, "Notice of Allowance," issued in connection with U.S. Appl. No. 16/339,969, dated Aug. 10, 2022, 7 pages.
*Novoluto GmbH* v. *Uccellini LLC*, "First Amended Complaint," filed with the United States District Court for the District of Oregon in connection with Case No. 6:20-cv-02284-MK on Feb. 4, 2022, 368 pages (uploaded in 3 parts).
*Novoluto GmbH* v. *Uccellini LLC*, "Answer and Affirmative Defenses to First Amended Complaint," filed with the United States District Court for the District of Oregon in connection with Case No. 6:20-cv-02284-MK on Feb. 17, 2022, 18 pages.
"Notification of an Opposition," issued by the European Patent Office in connection with European Patent No. EP375106 on Oct. 11, 2022, opposition filed by EIS GmbH, 128 pages (includes English translation).
"Opposition to a European Patent, Exhibit D6" filed with the European Patent Office by EIS GmbH in connection with European Patent No. EP375106 on Oct. 5, 2022, 18 pages (includes English translation).
"Opposition to a European Patent, Exhibit D7" filed with the European Patent Office by EIS GmbH in connection with European Patent No. EP375106 on Oct. 5, 2022, 18 pages (includes English translation).
"Opposition to a European Patent, Exhibit D8" filed with the European Patent Office by EIS GmbH in connection with European Patent No. EP375106 on Oct. 5, 2022, 18 pages (includes English translation).
Smith, J., "Fetish Fantasy Series Clit Pump: PD323100," May 21, 2013, https://www.youtube.com/watch?v=zJbKY1SQDas, 1 page.
FunkyCondom, "Jesse's Vibro Pussy Sucker," Feb. 5, 2011, https://www.youtube.com/watch?v=-YpufGFnKHQ, 1 page.
SexToyCanada, "Dr. Laura Berman Selene Vibrating Clitoral Pump Product Demo," Jun. 20, 2013, https://www.youtube.com/watch?v=4ZMybp0yWxU, 1 page.
Novelties for Lovers, "Dr. Laura Berman—Intimate Basics—Selene—Vibrating Clit Pump," Feb. 16, 2014, https://www.youtube.com/watch?v=-t85zgK2wHg, 1 page.
SexToyCanada, "Dr Laura Berman Intimate Basics Collection Thea Waterproof Silicone Clitoral PumpProduct D," Nov. 4, 2014, https://www.youtube.com/watch?v=K5jfBESc8p0.
SexToySuperMall, "Advanced Clitoral Pump," Sep. 1, 2009, https://www.youtube.com/watch?v=r1EaFHeiDCI, 1 page.
DiscreetFantasy, "Advanced Clitoral Pumps: SE062350," May 14, 2013, https://www.youtube.com/watch?v=E8a8J6TjENE, 1 page.
Pipedream, "Fetish Fantasy Series: Vibrating Stimulators," 2012, http://web.archive.org/web/20121105173055/http://www.pipedreamproducts.com/showsection-20b.php?Section=04&Sub1=Vibrating%20Stimulators, 3 pages.
Extreme Restraints, "The Clit Intensifier Pump," 2022, https://www.extremerestraints.com/the-clit-intensifier-pump.html, 6 pages.
Extreme Restraints, "Unique Vibrators," 2012, http://web.archive.org/web/20120104164504/http:/www.extremerestraints.com/unique-vibrators_85/, 2 pages.
Katherine McAlpine, "Balls, Cups and Discs: A History of Vibrators and Massage Machines, 1900-1940, Dissertation 2012," available at https://www.academia.edu/28556168/Balls_Cups_and_Discs_A_history_of_vibrators_and_massage_machines_1900_1940_Dissertation_2012, 41 pages.
CalExotics, Intimate Pump Vibro Pussy Sucker, 2022, https://calexotics.com/intimate-pump-vibro-pussy-sucker/, 5 pages.
MySexToySpot.com, "Clit Suckers & Pussy Pumps," 2013, available at https://web.archive.org/web/20131214165302/http://mysextoyspot.com/Extras/Pussy-Pumps-Pelvic-Exercisers/Clit-Suckers-Pussy-Pumps, 2 pages.
California Exotic Novelties, "Couture Collection," 2009, available at https://web.archive.org/web/20100628224310/calexotics.com/index.php, 3 pages.

(56) References Cited

OTHER PUBLICATIONS

Schroder, M. et al., "Clitoral Therapy Device for Treatment of Sexual Dysfunction In Irradiated Cervical Cancer Patients," 2005, International Journal of Radiation Oncology Biology Physics, 61(4), pp. 1078-1086, 9 pages.
Cellulite, "A Little Cellulite: Primer for the Beauty Vital 1000/1002/3000 and the TheraVac," Oct. 31, 2013, available at https://www.yumpu.com/de/document/read/21185793/c-e-l-l-u-l-i-t-e-mag-frenkel-midovital, 10 pages (English translation provided upon request).
EIS Inc. v. IntiHealth Ger GmbH et al., "Letter to The Honorable Gregory B. Williams from Gregory E. Stuhlman, Esquire Regarding Notifying the Court that Wow Tech Will Present Live Expert Witnesses at the Upcoming Claim Construction Hearing," filed with the United States District Court for the District of Delaware in connection with Case No. 1:19-cv-1227-GBW on Nov. 11, 2022, 2 pages.
EIS Inc. v. IntiHealth Ger GmbH et al., "Letter to The Honorable Gregory B. Williams from Brian P. Egan Regarding Claim Construction Disputes," filed with the United States District Court for the District of Delaware in connection with Case No. 1:19-cv-1227-GBW on Nov. 16, 2022, 6 pages.
EIS Inc. v. IntiHealth Ger GmbH et al., "Defendants' Motion and Memorandum in Support of Its Motion for Leave to File Early Motion for Partial Summary Judgment," filed with the United States District Court for the District of Delaware in connection with Case No. 1:19-cv-1227-GBW on Dec. 20, 2022, 21 pages.
EIS Inc. v. IntiHealth Ger GmbH et al., "Order," issued by the United States District Court for the District of Delaware in connection with Case No. 1:19-cv-1227-GBW on Jan. 9, 2023, 2 pages.
EIS Inc. v. IntiHealth Ger GmbH et al., "Plaintiff's Answering Brief in Opposition to Defendants' Motion for Leave to File Early Motion for Partial Summary Judgment," filed with the United States District Court for the District of Delaware in connection with Case No. 1:19-cv-1227-GBW on Jan. 10, 2023, 24 pages.
Novoluto GmbH v. Uccellini LLC, "Novoluto GmbH's Notice that Claim Construction Briefing and Hearing Are Unnecessary," filed with the United States District Court for the District of Oregon in connection with Case No. 6:20-cv-02284-MK on Dec. 22, 2022, 29 pages.
"Opposition to a European Patent, Exhibit E2" filed with the European Patent Office by EIS GmbH in connection with European Patent No. EP3305266 on Feb. 15, 2021, 218 pages (includes English translation). (uploaded in 4 parts, each part with a corresponding translation).
"Opposition to a European Patent, Exhibit E4" filed with the European Patent Office by EIS GmbH in connection with European Patent No. EP3305266 on Feb. 15, 2021, 157 pages (includes English translation).(uploaded in 3 parts, each part with a corresponding translation).
"Opposition to a European Patent, Exhibit E9" filed with the European Patent Office by EIS GmbH in connection with European Patent No. EP3305266 on Feb. 15, 2021, 161 pages (includes English translation). (uploaded in 3 parts, each part with a corresponding translation).
"Opposition to a European Patent, Exhibit E11" filed with the European Patent Office by EIS GmbH in connection with European Patent No. EP3305266 on Feb. 15, 2021, 278 pages (includes English translation). (uploaded in 7 parts, each part with a corresponding translation).
"Statement of Grounds and Particulars of Opposition Exhibit E8" filed with IP Australia in connection with Australian Patent Application No. 2018222907 on Feb. 24, 2021, 206 pages.
EIS Inc. v. IntiHealth Ger GmbH et al., "Plaintiff's Letter Brief In Opposition To Defendants' Motion To Strike Portions Of Dr. Abraham's Reports On Invalidity," filed with the United States District Court for the District of Delaware in connection with Case No. 1:19-cv-1227-GBW on Jul. 6, 2023, 8 pages.
EIS Inc. v. IntiHealth Ger GmbH et al., "Defendant Novoluto's Concise Statement Of Material Facts In Support Of Its Motion For Summary Judgment Of IPR Estoppel (Redacted Public Version)," filed with the United States District Court for the District of Delaware in connection with Case No. 1:19-cv-1227-GBW on Aug. 4, 2023, 8 pages.
EIS Inc. v. IntiHealth Ger GmbH et al., "Defendants' And Counterclaim Defendants' Answering Brief In Opposition To Defendants' Motion For Summary Judgment Of IPR Estoppel (Redacted Public Version)," filed with the United States District Court for the District of Delaware in connection with Case No. 1:19-cv-1227-GBW on Aug. 14, 2023, 16 pages.
EIS Inc. v. IntiHealth Ger GmbH et al., "Declaration Of Allan M. Soobert In Support Of Plaintiff And Counterclaim Defendants' Opposition To Defendants' Motion For Summary Judgment Of IPR Estoppel vol. 1 of 2 (Redacted Public Version) and Exhibit A (attachments 1-9)," filed with the United States District Court for the District of Delaware in connection with Case No. 1:19-cv-1227-GBW on Aug. 14, 2023, 239 pages.
EIS Inc. v. IntiHealth Ger GmbH et al., "Exhibit A (attachments 10-18) filed with Declaration Of Allan M. Soobert In Support Of Plaintiff And Counterclaim Defendants' Opposition To Defendants' Motion For Summary Judgment Of IPR Estoppel vol. 1 of 2 (Redacted Public Version)," filed with the United States District Court for the District of Delaware in connection with Case No. 1:19-cv-1227-GBW on Aug. 14, 2023, 236 pages.
EIS Inc. v. IntiHealth Ger GmbH et al., "Exhibit A (attachments 19-23) filed with Declaration Of Allan M. Soobert In Support Of Plaintiff And Counterclaim Defendants' Opposition To Defendants' Motion For Summary Judgment Of IPR Estoppel vol. 1 of 2 (Redacted Public Version)," filed with the United States District Court for the District of Delaware in connection with Case No. 1:19-cv-1227-GBW on Aug. 14, 2023, 239 pages.
EIS Inc. v. IntiHealth Ger GmbH et al., "Declaration Of Allan M. Soobert In Support Of Plaintiff And Counterclaim Defendants' Opposition To Defendants' Motion For Summary Judgment Of IPR Estoppel vol. 2 of 2 (Redacted Public Version) and Exhibit A (attachments 23-29)," filed with the United States District Court for the District of Delaware in connection with Case No. 1:19-cv-1227-GBW on Aug. 14, 2023, 266 pages.
EIS Inc. v. IntiHealth Ger GmbH et al., "Exhibits B-D filed with Declaration Of Allan M. Soobert In Support Of Plaintiff And Counterclaim Defendants' Opposition To Defendants' Motion For Summary Judgment Of IPR Estoppel vol. 2 of 2 (Redacted Public Version)," filed with the United States District Court for the District of Delaware in connection with Case No. 1:19-cv-1227-GBW on Aug. 14, 2023, 204 pages.
EIS Inc. v. IntiHealth Ger GmbH et al., "Plaintiff's And Counterclaim Defendants' Statement Of Material Facts And Responsive Statement Of Material Facts (Redacted Public Version)," filed with the United States District Court for the District of Delaware in connection with Case No. 1:19-cv-1227-GBW on Aug. 14, 2023, 9 pages.
EIS Inc. v. IntiHealth Ger GmbH et al., "Defendants' Statement Of Undisputed Material Facts In Support Of Its Opposition To Plaintiff's And Counterclaimdefendants' Motion For Partial Summary Judgment (No. 4)," filed with the United States District Court for the District of Delaware in connection with Case No. 1:19-cv-1227-GBW on Jun. 2, 2023, 5 pages.
EIS Inc. v. IntiHealth Ger GmbH et al., "Defendants' Statement Of Undisputed Material Facts In Support Of Its Opposition To Plaintiff And Counterclaimdefendants' Motion For Partial Summary Judgment (No. 5)," filed with the United States District Court for the District of Delaware in connection with Case No. 1:19-cv-1227-GBW on Jun. 2, 2023, 4 pages.
EIS Inc. v. IntiHealth Ger GmbH et al., "Plaintiff's And Counterclaim Defendants' Reply In Support Of Its Daubert Motion To Exclude Opinions Of Robert L. Stoll," filed with the United States District Court for the District of Delaware in connection with Case No. 1:19-cv-1227-GBW on Jun. 9, 2023, 9 pages.
EIS Inc. v. IntiHealth Ger GmbH et al., "Plaintiff's And Counterclaim Defendants' Reply In Support Of Their Daubert Motion To Exclude Certain "Stimulation Device" Opinions," filed with the United States District Court for the District of Delaware in connection with Case No. 1:19-cv-1227-GBW on Jun. 9, 2023, 5 pages.

(56) References Cited

OTHER PUBLICATIONS

*EIS Inc.* v. *IntiHealth Ger GmbH et al.*, "Plaintiff's And Counterclaim Defendants' Reply In Support Of Their Daubert Motion To Exclude Certain Opinions Of Drs. Cameron And Herbenick," filed with the United States District Court for the District of Delaware in connection with Case No. 1:19-cv-1227-GBW on Jun. 9, 2023, 7 pages.

*EIS Inc.* v. *IntiHealth Ger GmbH et al.* "Declaration Of Allan M. Soobert In Support Of Plaintiff And Counterclaim Defendants' Reply In Support Of Their Daubert Motion To Exclude Certain Opinions Of Drs. Cameron And Herbenick," filed with the United States District Court for the District of Delaware in connection with Case No. 1:19-cv-1227-GBW on Jun. 9, 2023, 92 pages.

*EIS Inc.* v. *IntiHealth Ger GmbH et al.* "Plaintiff's And Counterclaim Defendants' Reply In Support Of Its Daubert Motion To Exclude Opinions Of Dr. Debra Herbenick," filed with the United States District Court for the District of Delaware in connection with Case No. 1:19-cv-1227-GBW on Jun. 9, 2023, 5 pages.

*EIS Inc.* v. *IntiHealth Ger GmbH et al.*, "Plaintiff's And Counterclaim Defendants' Reply In Support Of Their Motion For Partial Summary Judgment As To Effective Filing Date Of The Asserted Claims Of U.S. Pat. Nos. 11,090,220, 11,103,418, 9,937,097 (No. 2)," filed with the United States District Court for the District of Delaware in connection with Case No. 1:19-cv-1227-GBW on Jun. 9, 2023, 16 pages (includes publicly available version of Exhibit N retrieved from PACER).

*EIS Inc.* v. *IntiHealth Ger GmbH et al.*, "Plaintiff's And Counterclaim Defendants' Response To Defendants' Statement Of Material Facts Regarding Motion No. 2 For Partial Summary Judgment That The Asserted Claims Of U.S. Pat. Nos. 11,090,220, 11,103,418, 9,937,097 Are Not Entitled To An Effective Filing Date Of Their Respective Earliest U.S. Parent Patents," filed with the United States District Court for the District of Delaware in connection with Case No. 1:19-cv-1227-GBW on Jun. 9, 2023, 7 pages.

*EIS Inc.* v. *IntiHealth Ger GmbH et al.*, "Plaintiff's And Counterclaim Defendants' Reply In Support Of Their Motion For Partial Summary Judgment Of Noninfringement Of All Asserted Claims Of U.S. Pat. No. 9,763,851 (No. 4)," filed with the United States District Court for the District of Delaware in connection with Case No. 1:19-cv-1227-GBW on Jun. 9, 2023, 7 pages.

*EIS Inc.* v. *IntiHealth Ger GmbH et al.*, "Plaintiff's And Counterclaim Defendants' Response To Defendant's Statement Of Undisputed Material Facts In Support Of Its Opposition To Plaintiff And Counterclaim- Defendants' Motion For Partial Summary Judgment (No. 4)," filed with the United States District Court for the District of Delaware in connection with Case No. 1:19-cv-1227-GBW on Jun. 9, 2023, 5 pages.

*EIS Inc.* v. *IntiHealth Ger GmbH et al.*, "Plaintiff's And Counterclaim Defendants' Reply In Support Of Their Motion No. 5 For Partial Summary Judgment Of Invalidity Of The Asserted Claims Of U.S. Pat. Nos. 11,090,220 And 11,103,418," filed with the United States District Court for the District of Delaware in connection with Case No. 1:19-cv-1227-GBW on Jun. 9, 2023, 5 pages.

*EIS Inc.* v. *IntiHealth Ger GmbH et al.*, "Plaintiff's And Counterclaim Defendants' Response To Defendant's Statement Of Undisputed Material Facts In Support Of Its Opposition To Plaintiff And Counterclaim- Defendants' Motion For Partial Summary Judgment (No. 5)," filed with the United States District Court for the District of Delaware in connection with Case No. 1:19-cv-1227-GBW on Jun. 9, 2023, 6 pages.

*EIS Inc.* v. *IntiHealth Ger GmbH et al.*, "Memorandum Order," issued by the United States District Court for the District of Delaware in connection with Case No. 1:19-cv-1227-GBW on Jun. 13, 2023, 3 pages.

Eros by NuGyn, Inc., May 31, 2011, available at https://www.youtube.com/watch?v=N9c3fv6vfeg, 1 page.

*EIS Inc.* v. *IntiHealth Ger GmbH et al.*, "Plaintiff's And Counterclaim Defendants' Answering Brief In Opposition To Defendants' Summary Judgment And Daubert Motions (Redacted Public Version)," filed with the United States District Court for the District of Delaware in connection with Case No. 1:19-cv-1227-GBW on Jun. 16, 2023, 61 pages.

*EIS Inc.* v. *IntiHealth Ger GmbH et al.*, "Plaintiff And Counterclaim Defendants' Statement Of Material Facts And Responsive Statement Of Material Facts (Redacted Public Version)," filed with the United States District Court for the District of Delaware in connection with Case No. 1:19-cv-1227-GBW on Jun. 16, 2023, 28 pages.

*EIS Inc.* v. *IntiHealth Ger GmbH et al.*, "Declaration Of Allan M. Soobert In Support Of Plaintiff And Counterclaim Defendants' Opposition To Defendants' Motions For Partial Summary Judgment And Daubert Motions and Exhibits A-C," filed with the United States District Court for the District of Delaware in connection with Case No. 1:19-cv-1227-GBW on Jun. 16, 2023, 62 pages.

*EIS Inc.* v. *IntiHealth Ger GmbH et al.*, "Exhibit D filed with Declaration Of Allan M. Soobert In Support Of Plaintiff And Counterclaim Defendants' Opposition To Defendants' Motions For Partial Summary Judgment And Daubert Motions," filed with the United States District Court for the District of Delaware in connection with Case No. 1:19-cv-1227-GBW on Jun. 16, 2023, 124 pages (uploaded in 4 parts).

*EIS Inc.* v. *IntiHealth Ger GmbH et al.*, "Exhibits E filed with Declaration Of Allan M. Soobert In Support Of Plaintiff And Counterclaim Defendants' Opposition To Defendants' Motions For Partial Summary Judgment And Daubert Motions," filed with the United States District Court for the District of Delaware in connection with Case No. 1:19-cv-1227-GBW on Jun. 16, 2023, 91 pages.

*EIS Inc.* v. *IntiHealth Ger GmbH et al.*, "Exhibit F filed with Declaration Of Allan M. Soobert In Support Of Plaintiff And Counterclaim Defendants' Opposition To Defendants' Motions For Partial Summary Judgment And Daubert Motions," filed with the United States District Court for the District of Delaware in connection with Case No. 1:19-cv-1227-GBW on Jun. 16, 2023, 40 pages.

*EIS Inc.* v. *IntiHealth Ger GmbH et al.*, "Exhibit G filed with Declaration Of Allan M. Soobert In Support Of Plaintiff And Counterclaim Defendants' Opposition To Defendants' Motions For Partial Summary Judgment And Daubert Motions," filed with the United States District Court for the District of Delaware in connection with Case No. 1:19-cv-1227-GBW on Jun. 16, 2023, 110 pages.

*EIS Inc.* v. *IntiHealth Ger GmbH et al.*, "Exhibit H filed with Declaration Of Allan M. Soobert In Support Of Plaintiff And Counterclaim Defendants' Opposition To Defendants' Motions For Partial Summary Judgment And Daubert Motions," filed with the United States District Court for the District of Delaware in connection with Case No. 1:19-cv-1227-GBW on Jun. 16, 2023, 116 pages.

*EIS Inc.* v. *IntiHealth Ger GmbH et al.*, "Exhibit I-N filed with Declaration Of Allan M. Soobert In Support Of Plaintiff And Counterclaim Defendants' Opposition To Defendants' Motions For Partial Summary Judgment And Daubert Motions," filed with the United States District Court for the District of Delaware in connection with Case No. 1:19-cv-1227-GBW on Jun. 16, 2023, 101 pages.

*EIS Inc.* v. *IntiHealth Ger GmbH et al.*, "Exhibits O-S filed with Declaration Of Allan M. Soobert In Support Of Plaintiff And Counterclaim Defendants' Opposition To Defendants' Motions For Partial Summary Judgment And Daubert Motions," filed with the United States District Court for the District of Delaware in connection with Case No. 1:19-cv-1227-GBW on Jun. 16, 2023, 119 pages.

*EIS Inc.* v. *IntiHealth Ger GmbH et al.*, "Exhibit T filed with Declaration Of Allan M. Soobert In Support Of Plaintiff And Counterclaim Defendants' Opposition To Defendants' Motions For Partial Summary Judgment And Daubert Motions," filed with the United States District Court for the District of Delaware in connection with Case No. 1:19-cv-1227-GBW on Jun. 16, 2023, 325 pages.

*EIS Inc.* v. *IntiHealth Ger GmbH et al.*, "Exhibit U filed with Declaration Of Allan M. Soobert In Support Of Plaintiff And

(56) References Cited

OTHER PUBLICATIONS

Counterclaim Defendants' Opposition To Defendants' Motions For Partial Summary Judgment And Daubert Motions," filed with the United States District Court for the District of Delaware in connection with Case No. 1:19-cv-1227-GBW on Jun. 16, 2023, 275 pages.

EIS Inc. v. IntiHealth Ger GmbH et al., "Exhibits V-AP filed with Declaration Of Allan M. Soobert In Support Of Plaintiff And Counterclaim Defendants' Opposition To Defendants' Motions For Partial Summary Judgment And Daubert Motions," filed with the United States District Court for the District of Delaware in connection with Case No. 1:19-cv-1227-GBW on Jun. 16, 2023, 140 pages.

EIS Inc. v. IntiHealth Ger GmbH et al., "Exhibits AQ-BX filed with Declaration Of Allan M. Soobert In Support Of Plaintiff And Counterclaim Defendants' Opposition To Defendants' Motions For Partial Summary Judgment And Daubert Motions," filed with the United States District Court for the District of Delaware in connection with Case No. 1:19-cv-1227-GBW on Jun. 16, 2023, 230 pages.

European Patent Office, "Notification under Article 94 (3) EPC," issued in connection with European Application No. 19153494.0 on Jun. 4, 2020, 8 pages (includes English translation).

European Patent Office, "Extended European Search Report," issued in connection with European Patent Application No. 21175706.7 on Sep. 20, 2021, 12 pages (includes English translation).

European Patent Office, "Transmittal of Decision/Summons," issued in connection with opposition of European Patent No. 3685809 on Oct. 25, 2022, 35 pages (includes English translation).

"Written Submission in Preparation to/during Oral Proceedings," filed with the European Patent Office by EIS GmBH in connection with opposition of European Patent No. 3685809 on Mar. 24, 2023, 44 pages (includes English translation).

European Patent Office, "Transmittal of Decision / Summons," issued in connection with opposition of European Patent No. 3685809 on Jun. 6, 2023, 283 pages (includes English translation).

"Statement of Grounds of Appeal," filed with the European Patent Office by EIS GmbH in connection with opposition of European Patent No. 3685809 on Nov. 1, 2023, 188 pages (includes English translation).

European Patent Office, "Notification under Article 94 (3) EPC," issued in connection with European Application No. 19161328.0 on Nov. 2, 2020, 8 pages (includes English translation).

European Patent Office, "Extended European Search Report," issued in connection with European Patent Application No. 21216838.9 on Apr. 5, 2022, 15 pages (includes English translation).

European Patent Office, "Transmittal of Decision / Summons," issued in connection with opposition of European Patent No. 3705106 on Jun. 13, 2023, 37 pages (includes English translation).

"Written Submission in Preparation to/during Oral Proceedings," filed with the European Patent Office by EIS GmBH in connection with European Patent No. 3705106 on Dec. 8, 2023, 56 pages (includes English translation).

European Patent Office, "Transmittal of Decision / Summons," issued in connection with opposition of European Patent No. 3405158 on Jun. 14, 2021, 27 pages (includes English translation).

"Written Submission in Preparation to/during Oral Proceedings," filed with the European Patent Office by EIS GmBH in connection with opposition of European Patent No. 3405158 on Dec. 7, 2021, 82 pages (includes English translation).

European Patent Office, "Transmittal of Decision / Summons," issued in connection with opposition of European Patent No. 3405158 on May 18, 2022, 67 pages (includes English translation).

IP Australia, "Examination Report," issued in connection with Australian Application No. 2017341098 on Jan. 27, 2022, 5 pages.

IP Australia, "Examination Report," issued in connection with Australian Application No. 2017341098 on May 10, 2022, 6 pages.

IP Australia, "Examination Report," issued in connection with Australian Application No. 2017341098 on Sep. 20, 2022, 5 pages.

IP Australia, "Examination Report," issued in connection with Australian Application No. 2019250096 on Jul. 1, 2022, 4 pages.

IP Australia, "Examination Report," issued in connection with Australian Application No. 2019250096 on Oct. 25, 2022, 5 pages.

Canadian Patent Office, "Office Action," issued in connection with Canadian Patent Application No. 3098337 on Mar. 18, 2022, 5 pages.

Canadian Patent Office, "Office Action," issued in connection with Canadian Patent Application No. 3098337 on Jan. 19, 2023, 4 pages.

German Patent and Trademark Office, "Examination Report," issued in connection with German Application No. 102018107939 on Mar. 29, 2019, 12 pages (includes English translation).

IP Australia, "Examination Report," issued in connection with Australian Application No. 2019247064 on Feb. 25, 2022, 4 pages.

IP Australia, "Examination Report," issued in connection with Australian Application No. 2019247064 on Jul. 15, 2022, 4 pages.

Canadian Patent Office, "Office Action," issued in connection with Canadian Patent Application No. 3095965 on Feb. 8, 2022, 5 pages.

Canadian Patent Office, "Office Action," issued in connection with Canadian Patent Application No. 3095965 on Jan. 23, 2023, 5 pages.

European Patent Office, "Notification under Article 94 (3) EPC," issued in connection with European Application No. 19787154.4 on Apr. 19, 2023, 10 pages (includes English translation).

German Patent and Trademark Office, "Examination Report," issued in connection with German Application No. 10 2018 107 961.3 on May 23, 2019, 22 pages (includes English translation).

EIS Inc. v. IntiHealth Ger GmbH et al., "Memorandum Opinion," issued by the United States District Court for the District of Delaware in connection with Case No. 1:19-cv-1227-GBW on Aug. 23, 2023, unsealed on Sep. 5, 2023, 22 pages.

EIS Inc. v. IntiHealth Ger GmbH et al., "Letter to The Honorable Gregory B. Williams from Brian P. Eagan Regarding Case Narrowing," filed with the United States District Court for the District of Delaware in connection with Case No. 1:19-cv-1227-GBW on Sep. 7, 2023, 3 pages.

EIS Inc. v. IntiHealth Ger GmbH et al., "Letter to The Honorable Gregory B. Williams Regarding IPR," filed with the United States District Court for the District of Delaware in connection with Case No. 1:19-cv-1227-GBW on Sep. 12, 2023, 3 pages.

EIS Inc. v. IntiHealth Ger GmbH et al., "Redacted Public Version of Jury Verdict," posted by the United States District Court for the District of Delaware in connection with Case No. 1:19-cv-1227-GBW on Sep. 15, 2023, 17 pages.

EIS Inc. v. IntiHealth Ger GmbH et al., "Letter to the Honorable Gregory B. Williams Regarding IPR (Redacted Public Version)," filed with the United States District Court for the District of Delaware in connection with Case No. 1:19-cv-1227-GBW on Sep. 26, 2023, 20 pages.

EIS Inc. v. IntiHealth Ger GmbH et al., "Joint Motion to Seal and Redact Memorandum Order (Redacted Public Version)," filed with the United States District Court for the District of Delaware in connection with Case No. 1:19-cv-1227-GBW on Sep. 26, 2023, 68 pages.

EIS Inc. v. IntiHealth Ger GmbH et al., "Post-Trial Status Report," filed with the United States District Court for the District of Delaware in connection with Case No. 1:19-cv-1227-GBW on Sep. 26, 2023, 19 pages.

EIS Inc. v. IntiHealth Ger GmbH et al., "Memorandum Opinion," issued by the United States District Court for the District of Delaware in connection with Case No. 1:19-cv-1227-GBW on Aug. 30, 2023, unsealed on Sep. 28, 2023, 14 pages.

EIS Inc. v. IntiHealth Ger GmbH et al., "Plaintiff's And Counterclaim Defendants' Brief In Support Of Their Inequitable Conduct And Unclean Hands Defenses (Redacted Public Version)," filed with the United States District Court for the District of Delaware in connection with Case No. 1:19-cv-1227-GBW on Nov. 17, 2023, 33 pages.

EIS Inc. v. IntiHealth Ger GmbH et al., "Plaintiff's And Counterclaim Defendants' Proposed Findings Of Fact And Conclusions Of Law Regarding Defendants' Inequitable Conduct And Unclean Hands Defenses (Redacted Public Version)," filed with the United

(56) References Cited

OTHER PUBLICATIONS

States District Court for the District of Delaware in connection with Case No. 1:19-cv-1227-GBW on Nov. 17, 2023, 29 pages.
EIS Inc. v. IntiHealth Ger GmbH et al., "Declaration Of Allan M. Soobert In Support Of Plaintiff's And Counterclaim Defendants' Brief In Support Of Their Inequitable Conduct And Unclean Hands Defenses (Redacted Public Version)," filed with the United States District Court for the District of Delaware in connection with Case No. 1:19-cv-1227-GBW on Nov. 17, 2023, 50 pages.
EIS Inc. v. IntiHealth Ger GmbH et al., "Defendants' And Counterclaimant's Response To Plaintiff's Opening Brief On Its Unenforceability Defenses (Redacted Public Version)," filed with the United States District Court for the District of Delaware in connection with Case No. 1:19-cv-1227-GBW on Dec. 15, 2023, 37 pages.
EIS Inc. v. IntiHealth Ger GmbH et al., "Declaration Of Califf T. Cooper In Support Of Defendants' And Counterclaimants' Opening Brief On Plaintiff's Unenforceability Defenses (Redacted Public Version)," filed with the United States District Court for the District of Delaware in connection with Case No. 1:19-cv-1227-GBW on Dec. 15, 2023, 37 pages.
EIS Inc. v. IntiHealth Ger GmbH et al., "Defendants' Proposed Findings Of Fact And Conclusions Of Law In Support Of Its Response To Plaintiff's Opening Brief On Its Unenforceability Defenses (Redacted Public Version)," filed with the United States District Court for the District of Delaware in connection with Case No. 1:19-cv-1227-GBW on Dec. 15, 2023, 22 pages.
EIS Inc. v. IntiHealth Ger GmbH et al., "Plaintiff's And Counterclaim Defendants' Reply Brief In Support Of Their Inequitable Conduct And Unclean Hands Defenses," filed with the United States District Court for the District of Delaware in connection with Case No. 1:19-cv-1227-GBW on Dec. 22, 2023, 17 pages.
EIS Inc. v. IntiHealth Ger GmbH et al., "Declaration Of Allan M. Soobert In Support Of Plaintiff's And Counterclaim Defendants' Reply Brief In Support Of Their Inequitable Conduct And Unclean Hands Defenses," filed with the United States District Court for the District of Delaware in connection with Case No. 1:19-cv-1227-GBW on Dec. 22, 2023, 56 pages.
United States Patent and Trademark Office, "Notice of Allowance," issued in connection with U.S. Appl. No. 15/888,568, dated Oct. 19, 2023, 9 pages.
United States Patent and Trademark Office, "Notice of Allowance," issued in connection with U.S. Appl. No. 16/811,907 dated Oct. 30, 2023, 15 pages.
United States Patent and Trademark Office, "Final Office Action," issued in connection with U.S. Appl. No. 17/029,974, dated Nov. 24, 2023, 98 pages.
United States Patent and Trademark Office, "Final Office Action," issued in connection with U.S. Appl. No. 17/461,470, dated Dec. 20, 2023, 37 pages.
United States Patent and Trademark Office, "Final Office Action," issued in connection with U.S. Appl. No. 17/403,609, dated Dec. 21, 2023, 22 pages.
United States Patent and Trademark Office, "Non-Final Office Action," issued in connection with U.S. Appl. No. 17/044,501, dated Dec. 21, 2023, 16 pages.
United States Patent and Trademark Office, "Non-Final Office Action," issued in connection with U.S. Appl. No. 17/044,503, dated Dec. 21, 2023, 11 pages.
United States Patent and Trademark Office, "Final Office Action," issued in connection with U.S. Appl. No. 16/339,969, dated Jan. 24, 2024, 9 pages.
"Written Request for Invalidation and Exhibits," filed with the Chinese National Intellectual Property Administration by third party in connection with Chinese Patent Application No. 201480052194.8 on Oct. 18, 2023, 79 pages (includes English translation of written request for invalidation).
Chinese National Intellectual Property Administration, "Reexamination Decision," issued in connection with Chinese Patent Application No. 201580077725.3, dated Dec. 21, 2023, 19 pages (includes English translation).
European Patent Office, "Information About the Result of Oral Proceedings," issued in connection with opposition of European Patent No. 3705106 on Feb. 8, 2024, 34 pages (includes English translation).
IP Australia, "Examination Report," issued in connection with Australian Application No. 2020201615 on Feb. 9, 2024, 8 pages.
United States Patent and Trademark Office, "Notice of Allowance," issued in connection with U.S. Appl. No. 16/811,907, dated Feb. 16, 2024, 16 pages.
Canadian Patent Office, "Office Action," issued in connection with Canadian Patent Application No. 3,095,965 on Apr. 10, 2024, 5 pages.
European Patent Office, "Notification under Article 94 (3) EPC," issued in connection with European Application No. 21175706.7 on May 28, 2024, 8 pages (includes English translation).
European Patent Office, "Decision Revoking the European Patent," issued in connection with opposition of European Patent No. 3705106 on Mar. 19, 2024, 192 pages (includes English translation).
European Patent Office, "Decision Revoking the European Patent," issued in connection with opposition of European Patent No. 3305266 on Mar. 28, 2024, 303 pages (includes English translation).
"Opposition to a European Patent," filed with the European Patent Office by EIS GmbH in connection with European Patent No. 3267960 on Mar. 7, 2024, 236 pages (includes English translation).
"Opposition to a European Patent, Exhibit D3" filed with the European Patent Office by EIS GmbH in connection with European Patent No. 3267960 on Mar. 7, 2024, 6 pages (includes English translation).
"Opposition to a European Patent, Exhibit D4" filed with the European Patent Office by EIS GmbH in connection with European Patent No. 3267960 on Mar. 7, 2024, 4 pages (includes English translation).
"Opposition to a European Patent, Exhibit D5" filed with the European Patent Office by EIS GmbH in connection with European Patent No. 3267960 on Mar. 7, 2024, 46 pages (includes English translation).
"Opposition to a European Patent, Exhibit D6" filed with the European Patent Office by EIS GmbH in connection with European Patent No. 3267960 on Mar. 7, 2024, 25 pages (includes English translation).
"Opposition to a European Patent, Exhibit D7" filed with the European Patent Office by EIS GmbH in connection with European Patent No. 3267960 on Mar. 7, 2024, 43 pages (includes English translation).
"Opposition to a European Patent, Exhibit D9" filed with the European Patent Office by EIS GmbH in connection with European Patent No. 3267960 on Mar. 7, 2024, 4 pages (includes English translation).
"Opposition to a European Patent, Exhibit D13" filed with the European Patent Office by EIS GmbH in connection with European Patent No. 3267960 on Mar. 7, 2024, 4 pages (includes English translation).
European Patent Office, "Brief Communication—Opposition Proceedings," issued in connection with opposition of European Patent No. 3267960 on Mar. 22, 2024, 6 pages (includes English translation).
"Opposition to a European Patent," filed with the European Patent Office by EIS GmbH in connection with European Patent No. 3400926 on Mar. 7, 2024, 236 pages (includes English translation).
"Opposition to a European Patent, Exhibit D18" filed with the European Patent Office by EIS GmbH in connection with European Patent No. 3400926 on Mar. 7, 2024, 2 pages (includes English translation).
"Opposition to a European Patent, Exhibit D19" filed with the European Patent Office by EIS GmbH in connection with European Patent No. 3400926 on Mar. 7, 2024, 18 pages (includes English translation).

(56) References Cited

OTHER PUBLICATIONS

"Opposition to a European Patent, Exhibit D20" filed with the European Patent Office by EIS GmbH in connection with European Patent No. 3400926 on Mar. 7, 2024, 12 pages (includes English translation).

"Opposition to a European Patent, Exhibit D21" filed with the European Patent Office by EIS GmbH in connection with European Patent No. 3400926 on Mar. 7, 2024, 10 pages (includes English translation).

"Opposition to a European Patent, Exhibit D22" filed with the European Patent Office by EIS GmbH in connection with European Patent No. 3400926 on Mar. 7, 2024, 44 pages (includes English translation).

European Patent Office, "Brief Communication—Opposition Proceedings," issued in connection with opposition of European Patent No. 3400926 on Mar. 22, 2024, 6 pages (includes English translation).

European Patent Office, "Notification under Article 94 (3) EPC," issued in connection with European Patent Application No. 18206800.7 on May 10, 2022, 8 pages (includes English translation).

European Patent Office, "Notice of Submission of Third Party Observation," issued in connection with European Patent Application No. 18206800.7 on Feb. 7, 2024, 6 pages (includes English translation).

European Patent Office, "Notification under Article 94 (3) EPC," issued in connection with European Patent Application No. 18206800.7 on Feb. 27, 2024, 10 pages (includes English translation).

"Written Request for Invalidation and Exhibits," filed by third party with the Chinese National Intellectual Property Administration in connection with Chinese Patent Application No. 201480052194.8 on Aug. 16, 2023, 74 pages (includes English translation of written request for invalidation).

"Supplemental Opinion," filed by third party with the Chinese National Intellectual Property Administration in connection with Chinese Patent Application No. 201480052194.8 on Sep. 11, 2023, 64 pages (includes English translation).

"Written Request for Invalidation and Exhibits," filed by third party with the Chinese National Intellectual Property Administration in connection with Chinese Patent Application No. 201480052194.8 on Sep. 25, 2023, 85 pages (includes English translation of written request for invalidation).

China National Intellectual Property Administration, "Fourth Office Action," issued in connection with Chinese Application No. CN201710709587.7, on Feb. 28, 2024, 10 pages (includes English translation).

IP Australia, "Opposition—Decision Issued," issued in connection with Australian Patent Application No. 2015386680 on Oct. 2, 2020, 53 pages.

IP Australia, "Opposition—Section 104 Amendments," issued in connection with Australian Patent Application No. 2018203659 on Jun. 30, 2021, 14 pages.

"Opponent Comments Regarding Final Determination," filed with the Australian in connection with opposition of Australian Patent Application No. 2018203659 on Feb. 18, 2022, 11 pages.

IP Australia, "Opposition—Decision Issued," issued in connection with Australian Patent Application No. 2018203659 on Apr. 28, 2022, 7 pages.

IP Australia, "Examination Report No. 1 for Standard Patent Application," issued in connection with Australian Application No. 2022203319, on Aug. 1, 2023, 6 pages.

United States Patent and Trademark Office, "Office Action," issued in connection with U.S. Appl. No. 17/044,503, dated Jul. 5, 2024, 8 pages.

United States Patent and Trademark Office, "Office Action," issued in connection with U.S. Appl. No. 17/044,501, dated Jul. 5, 2024, 15 pages.

United States Patent and Trademark Office, "Office Action," issued in connection with U.S. Appl. No. 17/461,470, dated Jul. 9, 2024, 44 pages.

United States Patent and Trademark Office, "Office Action," issued in connection with U.S. Appl. No. 17/403,609, dated Aug. 6, 2024, 45 pages.

IP Australia, "Examination Report No. 1 for Standard Patent Application," issued in connection with Australian Application No. 2020200457, on Aug. 29, 2024, 4 pages.

IP Australia, "Examination Report No. 2 for Standard Patent Application," issued in connection with Australian Application No. 2020200457, on Oct. 22, 2024, 5 pages.

\* cited by examiner

STIMULATION DEVICE FOR A MALE PENIS

RELATED APPLICATION

This patent arises from a U.S. patent application that claims the benefit of, and priority to, European Patent Application No. EP 19 153 494.0, filed Jan. 24, 2019. European Patent Application No. EP 19 153 494.0 is hereby incorporated herein in its entirety.

FIELD OF THE DISCLOSURE

The invention concerns a stimulation device for a male penis, and in particular an applicator for such a stimulation device. The stimulation device has a pressure field generation device for generating a pneumatic alternating pressure field, which can be applied to a region of a penis to be stimulated by means of the applicator.

BACKGROUND

There are various stimulation devices for the male penis of known art, which can lead to a sexual arousal, or can potentially increase a sexual arousal to a climax. Such stimulation devices usually have an accommodation chamber, which is essentially closed, and has an opening into which the (erect) penis can be introduced. The front end of the accommodation chamber is often closed, such that, in particular, the glans of the penis is enclosed. The inner face of the accommodation chamber lies against the penis, and can have structures, such as nubs, to enhance stimulation. In addition to manual devices, in which a user has to perform desired movements for stimulation by friction, automatic devices are also of known art.

Such automatic devices can either imitate a manual movement, or can perform other stimulating movements. For example, the shape or volume of all or part of the accommodation chamber can be modified by mechanical or pneumatic devices acting on the accommodation chamber so as to generate a stimulation. For this purpose, the accommodation chamber can be configured as a flexible sleeve made of a soft material, and can be located in a solid housing which, in addition to the accommodation chamber, can house appropriate drives, pumps, stimulation heads, batteries, and similar. Stimulation devices are also of known art in which the accommodation chamber is sealed on the shaft of the penis, such that a stimulation effect can be achieved by means of a varying under-pressure.

Since the devices of known art often implement only one stimulation function, the stimulation effect is often perceived as unsatisfactory. Moreover, in the case of stimulation devices of known art, the entire penis is usually introduced into the accommodation chamber, such that these devices are also relatively unwieldy by virtue of the large housing. Such devices are also usually only available in one standard size, and are often not sufficiently adaptable for different penis sizes. Due to the closed shape of the accommodation chamber, cleaning can also be difficult, also because lubricant, or similar is often necessary to avoid skin irritation as a result of friction.

SUMMARY

The object of the present invention is therefore to create a stimulation device for a male penis that is improved in terms of stimulation of the penis and application.

The object is achieved by means of an applicator for a stimulation device for a male penis and a stimulation device with such an applicator with the features of the independent claims. An article with such a stimulation device and at least one additional applicator is also provided.

In accordance with a first aspect, an applicator for a stimulation device for a male penis is provided. The applicator comprises an applicator body with a contact region, which is configured to come at least partially into contact with a penis, when the applicator body is placed on the latter. Furthermore, the applicator comprises a pressure chamber, which is formed on the applicator body and is configured to receive a pneumatic alternating pressure field from a pressure field generation device. The pressure chamber has an opening in the contact region, such that the alternating pressure field can be applied via the opening to a region of the penis that is to be stimulated. A sealing device is formed on the applicator body, and is configured to seal the pressure chamber from the environment when the applicator body is placed on the penis.

In accordance with another aspect, a stimulation device for a male penis is provided, which comprises at least one such applicator and a pressure field generation device for the generation of a pneumatic alternating pressure field. The pressure field generation device has a pneumatic output port, via which a generated pneumatic alternating pressure field can be outputted, wherein the pneumatic output port can be connected, or is connected, to the applicator, such that the pneumatic alternating pressure field can be transmitted to the pressure chamber of the applicator.

In accordance with yet another aspect, an article is provided with such a stimulation device for a male penis, and at least one other such applicator, wherein the applicators included in the article are preferably different. The article can also be designated as a set, and allows a modular design of the stimulation device.

In accordance with a preferred embodiment, the applicator is detachably connected to the pressure field generation device, either directly, or by means of a connector as described in more detail below, such that it can be disconnected from the pressure field generation device, and reconnected to it for cleaning or replacement. Alternatively, however, the applicator can be permanently connected to the pressure field generation device or formed integrally with the latter.

Applicators of an article, or a set, can differ in particular with regard to shape, size, geometry, and the like. The applicators can also differ in other functional parts, described above and in what follows, such as the sealing device, or the configuration of the contact region. Provision can be made for the applicators to differ in terms of the geometry and/or size of their pressure chamber, as a result of which stimulation of varying intensity can result while the pressure field generation device remains in constant operation. Alternatively, however, provision can be made for the applicators to be the same, such that an applicator can be replaced in the event of loss, damage, wear, or the like. Particularly advantageous, the applicators are detachably connected to the pressure field generation device, for example via a connector, as described in more detail below, which can also be regarded as a part of the article. In one variant the article can comprise more than one connector, wherein the connectors can be identical or different.

By means of the applicator, an alternating pressure field generated by the pressure field generation device can be applied to a portion of the penis that is to be stimulated. For this purpose, the applicator with the contact region is placed on a portion of the penis to be stimulated, for example the glans, the coronal sulcus and/or the frenulum (frenulum of prepuce of penis), as described in more detail below. The opening of the pressure chamber is arranged in the contact region and points towards the penis during use, such that there is no contact between the penis and the applicator in the region of the opening of the pressure chamber, and the pressure chamber directly abuts against the skin of the penis. The pressure change field is thus applied directly onto the penis.

In contrast to stimulation devices of known art, the stimulating excitation is thus carried out by a contactless transmission of a stimulation force by means of the alternating pressure field. In particular, parts of the pressure field generation device, for example a flexible wall or membrane of the pressure field generation device, which is deflected accordingly to generate the alternating pressure fields, do not come into contact with the penis, in particular not during any phase of the operation. In other words, the flexible wall or flexible membrane is spaced at a distance from the opening of the pressure chamber, and thus also at a distance from the sealing device, and in particular is different from the latter. This is particularly advantageous for the stimulation of the sensitive frenulum, as will be described in more detail below. Thus, a particular stimulation effect can be created that differs from the effect of conventional tactile stimulation devices. The applicator is compact and can easily be placed on the penis, making it easy to use and also easy to clean.

The sealing device is configured in such a way that when the applicator is placed on the penis, the pressure chamber is sealed from the environment. In this manner, an alternating pressure field can build up and the portion of the penis to be stimulated, that is to say, in particular the portion of the penis that is located in the region of the opening of the pressure chamber immediately adjacent to the pressure chamber, can be stimulated by means of the alternating pressure field.

Here an alternating pressure field is to be understood to be a type of varying pressure field that has both under- and over-pressures with respect to the ambient pressure, for example alternating under- and over-pressure phases, or another prescribed pattern of possibly identical or different under- and over-pressures. This alternating pressure field prevails in the pressure chamber of the applicator, in particular in the region of the opening of the pressure chamber, that is to say, parameters such as frequency and amplitude of the alternating pressure field are to be measured at the opening. The pressure can alternate with a frequency of between 5 Hz and 250 Hz, preferably of between 10 Hz and 200 Hz, further preferably of between 20 Hz and 100 Hz, for example 60 Hz. The pressure difference can be between 20 mbar and 800 mbar, preferably between 50 mbar and 750 mbar, further preferably between 100 mbar and 700 mbar, for example 200 mbar, wherein the pressure difference is that between the highest over-pressure and the lowest under-pressure, and is preferably arranged symmetrically about an ambient pressure. At a normal ambient pressure of about 1 bar, for example, the alternating pressure field can lead to a pressure of between 0.7 bar and 1.3 bar in the pressure chamber, which corresponds to a pressure difference of 0.6 bar (600 mbar). The alternating pressure field is in particular a pneumatic alternating pressure field, that is to say, air in particular is used as the pressure medium. However, it is conceivable for the alternating pressure field to be transmitted via another medium, for example via a fluid such as water, a gel, or similar, which is introduced into the pressure chamber.

The sealing device is thus in particular configured to seal the pressure chamber from the environment with regard to both under- and over-pressures relative to an ambient pressure of the environment. In other words, the sealing device is configured to prevent, or at least almost prevent, flows, in particular air flows, in both directions, that is to say, from the pressure chamber into the environment, and from the environment into the pressure chamber. The environment includes in particular regions outside the pressure chamber, or outside the applicator.

The sealing device can be formed and configured, in particular in the contact region, to come into contact with the penis at least in some sections when the applicator body is applied, so as to seal the pressure chamber from the environment. In particular, the sealing device can be formed around the opening of the pressure chamber, for example in the form of a circle, an oval, or similar. The sealing device can also be configured in such a way that it comprises a plurality of sections, which deform elastically when a contact pressure is applied so as to form a peripheral or circumferential seal for sealing the pressure chamber from the environment.

It will be appreciated that the sealing device can also have other shapes that are suitable for providing a sealing contact with the penis. In particular, however, it is preferable if the sealing device does not surround the penis peripherally, but lies at the side of the penis, for example in the region of the frenulum. The sealing device can alternatively or additionally be formed at least in sections in an outer edge region of the applicator body, in particular in the contact region.

The sealing device can be designed as a raised structure in the contact region and can, for example, have a sealing lip, a sealing membrane, a bead, a projection, or similar. It is advantageous for the sealing device to be made of a soft material, such that it adapts to the anatomical conditions of the penis when it is placed on the penis, and fits tightly against the skin of the penis. For example, the sealing device can have a round, for example a semi-circular cross-sectional profile. A contact pressure can be applied to the sealing device so as to improve the sealing. This can be done manually, or by a retaining device, as described in more detail below.

The sealing device can in particular be designed so as to seal the pressure chamber when the applicator lies stationary on the penis, that is to say, is not moved. However, the sealing device can be of a nature and designed as a sliding seal such that at least a partial sealing of the pressure chamber, or even an approximate seal as in the unmoved state, is achieved even when the applicator is moved along the penis. The sealing device is advantageously designed in such a way that, despite effective sealing in the unmoved state, it permits, or at least does not hinder, a movement of the applicator along the penis. For example, the sealing device can, for this purpose, be designed to be particularly soft and rounded. If necessary, additional stimulation of the penis can be achieved when the applicator is moved by the sealing device, if the sealing device is designed as a raised structure in the contact region.

In the contact region of the applicator body at least one anatomically shaped projection can be arranged, which preferably follows the profile of a coronal sulcus of the penis at least in sections. The anatomically shaped projection can be connected to or disconnected from the sealing device. It can support the sealing effect and also serve to facilitate a correct positioning of the applicator on the penis. The anatomically shaped projection can be adapted to the desired anatomy in terms of its position, course, and/or cross-sectional profile. For example, the projection can follow at least part of the coronal sulcus, for example in the region of the frenulum. In this case, the anatomically shaped projection can be formed by two sections that enclose an angle. Like the sealing device, the projection can be designed, for example, as a bead or a lip.

The pressure chamber, which can also be called the application chamber, is preferably configured to accommodate, at least partially, a frenulum of the penis when the applicator body is placed on the penis. In particular, the opening of the pressure chamber in the contact region of the applicator body is dimensioned and shaped such that it at least partially or completely surrounds the frenulum. For example, the diameter of the opening for the accommodation of all or part of the frenulum can be less than 40 mm, preferably less than 30 mm, more preferably less than 20 mm.

Since the pressure chamber is open towards the penis, the alternating pressure field can in this manner act directly on the frenulum, for example by gently drawing the frenulum into the pressure chamber during the under-pressure phases. The type of stimulation by means of a pneumatic alternating pressure field is particularly effective because the erogenous zone is sensitised in the under-pressure phase by increased blood circulation and stimulated in the over-pressure phase. This region of the penis is one of the strongest erogenous zones of the male body, so an appropriate stimulation can lead to sexual arousal, or can increase sexual arousal. In particular, stimulation by means of an alternating pressure field, that is to say, the contactless application of a stimulation force, is particularly suitable for the sensitive frenulum.

The applicator can have a connector arranged on the applicator body and configured to be connected to a pressure field generation device, and to receive a pneumatic alternating pressure field from the latter, wherein the pressure chamber is fluidically connected to the connector. It is particularly advantageous to provide a port if the applicator can be detachably connected to a pressure field generation device. In particular, the pressure field generation device can be located on one side of the port and the pressure chamber on another, in particular opposing, side of the port. For example, a flexible membrane configured to generate an alternating pressure field thus does not form a limitation of the pressure chamber, but is arranged outside the pressure chamber, preferably at a distance from the pressure chamber.

A fluid channel can be formed in the applicator body, via which the port and the pressure chamber are fluidically connected with one another. In particular, the fluid channel can have a smaller cross-section than the pressure chamber, that is to say, the pressure chamber can have a larger cross-section than the fluid channel. In this manner, the alternating pressure field can be effectively transmitted from the port to the pressure chamber.

For example, the opening of the pressure chamber can have the same cross-section as the pressure chamber, such that the alternating pressure field can be applied over the largest possible region to the portion of the penis to be stimulated. At the same time the port to the pressure generation device can be kept small in cross-section.

In order to further increase the surface on which the alternating pressure field acts on the penis, in particular the surface of the opening of the pressure chamber in the contact region, the pressure chamber can expand towards the opening. Alternatively, the pressure chamber can have a constant cross-sectional area and can be of a cylindrical design, for example.

Conversely, provision can be made for the cross-section of the pressure chamber to be reduced towards the opening. For example, independently of this, a cross-section of the fluid channel and/or connection can also be larger than a cross-section of the pressure chamber and/or the opening. In this manner, the pressure in the region of the opening can be increased. Also, regardless of the geometry of the pressure chamber, the opening can have a smaller cross-sectional area than the region of the pressure chamber adjacent to the opening.

A connection-side opening of the pressure chamber, through which the pneumatic alternating pressure field can be introduced into the pressure chamber, can be arranged opposite the opening of the pressure chamber in the contact region of the applicator body. This arrangement is advantageous for the transmission of the alternating pressure field from the pressure generation device via the port into the pressure chamber to the opening of the pressure chamber, and finally to the penis, since the pressure forces act along an axis. Alternatively, however, provision can be made for the port to be located at a different point in the applicator relative to the pressure chamber, for example at the side of the pressure chamber. If a fluid channel is provided as mentioned above, the fluid channel can either run in a straight line, or take any other curved or angled profile so as to connect the port fluidically to the pressure chamber.

The contact region of the applicator body can define an accommodation chamber bounded by the contact region and configured to receive the penis, at least partially, such that the contact region lies along at least part of the periphery of the penis. Since the opening of the pressure chamber is located in the contact region, it opens directly into the accommodation chamber. In other words, as described above, the pressure chamber is open towards the accommodation chamber, and thus also towards the penis when the applicator is in contact with the penis, such that the alternating pressure field can act directly on the skin of the penis, for example the frenulum. The opening of the pressure chamber and the sealing device can thus be located in particular in an application surface defined by the contact region.

The accommodation chamber can, in particular, have two open ends opposite each other along a longitudinal direction, wherein the penis can enter the applicator through one of the ends and possibly exit from the other end. For this purpose, for example, the accommodation chamber can be designed symmetrically with respect to a plane perpendicular to the longitudinal axis. The accommodation chamber can be closed or open along its periphery. If the accommodation chamber is open along the periphery, the contact region only lies along part of the periphery of the penis, for example in a region that comprises the frenulum.

The accommodation chamber can be wide open, such that the contact region lies against only part of the periphery of the penis, for example along a quarter to half of the periphery. In order to stimulate the frenulum, it can be sufficient if the contact region lies against only the underside of the penis. This allows a particularly compact configuration of the applicator and easy application, without the need to introduce the penis into the applicator.

In other configurations, the attachment region can surround the penis further, and for example, attachment can occur over more than half of the periphery of the penis up to the entire periphery. This can improve the retention of the applicator on the penis, but can require the introduction of the penis into the applicator.

The contact region or accommodation chamber can be formed by a particularly soft material that clings to the surface of the penis, for example a silicone or a silicone mixture with a low Shore hardness, for example one that is less than 5, preferably less than 3, more preferably less than 2. A self-lubricating silicone can also be used to avoid or reduce the use of lubricant, in particular if it is intended to move the applicator. To increase the stimulation when the applicator is moved along the penis, the contact region can be provided with raised structures, such as nubs, ribs, or similar. The pressure chamber and the port of the applicator can be formed in a part of the applicator that is made of a stiffer material, and which can, for example, form a shell around a soft liner, which forms the contact region. The material used for this purpose can be, for example, a silicone or a silicone mixture with a higher Shore hardness, for example one that is greater than 20, preferably greater than 30, more preferably greater than 40, or a hard plastic, such as acrylonitrile-butadiene-styrene (ABS), and similar.

Alternatively, the applicator as a whole can consist of one material, in particular it can be made as one piece. Plastics that on the one hand are not too hard and are suitable for contact with the penis, and on the other hand have sufficient stiffness to form the pressure chamber and the port, such as silicones or suitable silicone mixtures, are particularly suitable for this purpose. The applicator is manufactured by means of an injection moulding process, and in particular also by two or more component injection moulding process, wherein silicones of different hardness are joined together to form one part.

The applicator can also include a retaining device, which is configured to hold the applicator body in place after placing on the penis. The term "retaining device" refers in particular to devices that hold the applicator in place after it has been placed on the penis, without it being held by the user, so that it does not fall off. In particular, the retaining device is designed to hold the applicator at a point on the penis where the opening of the pressure chamber is located above a portion of the penis to be stimulated, for example above the frenulum. This allows the applicator to be used "hands-free", without the user needing to hold the applicator.

Alternatively, the retaining device can serve to facilitate the retention of the applicator by the user. In this case, the retaining device can also, for example, be referred to as a 'gripping device'. Flexible wings can, for example, be provided, which can wrap around at least part of the periphery of the penis, making it easier to hold the applicator by hand. Needless to say, other gripping types of structure that make it easier to hold the applicator are also conceivable.

The retaining device can extend from the body of the applicator and can be configured to engage with at least part of the periphery of the penis. This is particularly advantageous if the contact region of the applicator body only extends over part of the periphery of the penis. The retaining device can then extend from the applicator body over at least part or all of the rest of the periphery of the penis. The retaining device can, for example, have wings, bands, straps, or similar. Where appropriate, means of securing or tightening the bands or straps can be provided. In addition, the retaining device can comprise, for example, a flexible ring-like structure, if necessary, extending around the periphery of the penis. Regardless of the configuration of the retaining device, the retaining device can be detachable or firmly connected to the applicator body.

The retaining device can be configured so as to increase the pressure of the sealing device against the penis. In other words, instead of simply retaining the applicator, the retaining device can be adjusted to change the contact pressure of the sealing device. For example, the retaining device can include means of tightening, wherein, for example, an inner diameter of the accommodation chamber can be reduced such that the contact pressure of the sealing device on the penis increases. Instead of a tightening mechanism, the applicator can also have a pressure device, for example in the form of one or more air cushions, which can be inflated to strengthen the fit of the applicator on the penis and increase the contact pressure.

Provision can, for example, be made for the applicator to have an outer shell, which can consist of two or more parts, which can be moved, for example displaced or swivelled, relative to each other in such a way that an inner diameter of the accommodation chamber is reduced. By increasing the contact pressure, the stimulation effect can be increased as required and the risk of the applicator slipping can be reduced. Alternatively, in particular if the retaining device is only designed as a gripping device, the contact pressure can also be increased by hand.

The retaining device can have a fixing device so as to fix the retaining device in a desired position. In particular, a desired contact pressure can be maintained in this manner, without the user needing to hold the applicator or the retaining device by hand. The fixing device can, for example, include a latching mechanism, which prevents the retaining device from being released after tightening. Appropriate means for releasing the fixing device, such as a knob or lever, can be provided such that the applicator can be removed from the penis, or at least the contact pressure on the penis can be reduced.

As already mentioned above, the stimulation device can include a connector for connecting the applicator to the pressure field generation device. The connector can have a first port, which is arranged to be fluidically connected to the pneumatic output port of the pressure field generation device, and a second port, which is arranged to be fluidically connected to the port of the applicator, such that the pneumatic alternating pressure field can be transmitted by means of the connector from the pressure field generation device to the pressure chamber of the applicator.

The connector can be provided as a separate part and can be detachably connected to both the applicator and the pressure field generation device. This allows a modular design of the stimulation device, in particular if a plurality of, possibly different applicators are to be used. It also makes it easier to clean the stimulation device, thus improving hygiene. However, the connector can be permanently connected to the applicator, or the pressure field generation device, or both. The connector can, for example, take the form of a hose, in particular a flexible hose, a tube or any other suitable structure that has an appropriate cavity for transmitting the alternating pressure field from the pressure generation device to the port of the applicator.

A tube, in particular a longer tube, allows a spatial distance between the applicator and the pressure field generation device, which can facilitate hands-free use of the stimulation device, since the pressure field generation device can be placed next to the user, for example. A short connector or a direct connection of the pressure field generation device to the terminal connector of the applicator allows a compact design of the stimulation device, wherein the stimulation device can, however, possibly need to be held by hand during operation, due to the higher weight of the whole device compared to the applicator alone.

It is advantageous to use plug connectors to connect the connector with the pressure field generation device and the applicator, or to connect the applicator directly with the pressure field generation device. This allows a quick and easy connection, making it easier to use the stimulation device. The plug connectors can have appropriate seals, such as sealing lips, O-rings, or similar, or can be sufficiently tight on their own to transmit the alternating pressure field essentially without losses. Needless to say, other connection mechanisms, such as screw connections, bayonet connections, snap connections, or similar, are also possible.

The connector can have a coupling device, which is arranged between the first port and the second port, and is configured to transmit the pneumatic alternating pressure field and to prevent a fluid flow, in particular a fluid flow from the second port to the first port, that is to say, from the applicator to the pressure field generation device. This prevents water, body fluids, or other contaminants, from passing from the opening of the pressure chamber via the pressure chamber and the port of the applicator into the connector, and possibly even into the pressure field generation device, which could be caused in particular by capillary forces in a thin tube. The coupling device thus serves as a non-return valve.

It is advantageous to place the coupling device between the first and second ports of the connector, closer to the second port, that is to say, closer to the applicator, so as to keep the part of the connector into which liquids can potentially enter as small as possible. If necessary, the coupling device can be formed directly on the second port, or can form the port to the applicator. The coupling device can be separable, such that a first part of the connector can remain connected to the pressure field generation device, and a second part of the connector, which is located between the coupling device and the applicator, can be cleaned separately.

By providing a coupling device, fluids from the applicator can be prevented from flowing through the connector. At the same time, the coupling device in the opposite direction allows the alternating pressure field to be transmitted from the pressure generation device to the applicator. For this purpose the coupling device can have a flexible membrane that is impermeable to fluid. In particular, the membrane can be impermeable to fluids of any viscosity. However, alternatively or additionally, a semi-permeable membrane and/or other filtering device can be provided, which at least retains solids.

The membrane can form a partition between two chambers in the coupling device, wherein one of the chambers is located on the side of the membrane facing the pressure field generation device and the other of the chambers is located on the side of the membrane facing the applicator. The chambers allow a deflection of the flexible membrane so as to transmit the alternating pressure field. For this purpose a cross-sectional area of the coupling device is preferably larger than that of the connector.

The invention is described in what follows, with the aid of the accompanying figures as examples. For a better understanding of the invention, the drawings show only schematically preferred embodiments of the invention, wherein the invention is not limited to the preferred embodiments shown.

DETAILED DESCRIPTION

Figure 1:
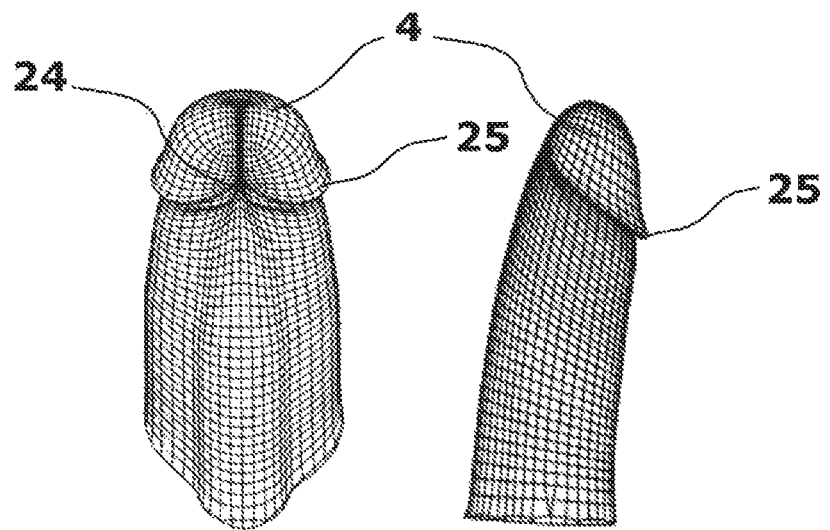
FIG. 1: shows a male penis.

For a better understanding of the invention, relevant aspects of the anatomy of a human male penis, in particular with regard to a desired stimulation by means of a stimulation device in accordance with the invention, are explained with reference to FIG. 1. The glans 4 and the frenulum 24 of the male member are among the strongest erogenous zones of the male body, wherein appropriate stimulation or irritation can lead to sexual arousal or increase sexual arousal. The sexual arousal can lead to the male orgasm and an ejaculation reflex. An under-pressure can also promote blood circulation in the stimulated region and an over-pressure can be used to apply a stimulating force.

The frenulum 24 and the coronal sulcus 25, that is to say, the transition between the glans 4 and the penis shaft, are particularly sensitive to the stimulation or irritation cited.

With a stimulation device in accordance with the invention, in particular with an appropriate applicator in accordance with the invention, it is possible to perfuse and stimulate the glans 4 of the male member, in particular the frenulum, in a constant alternation of over- and under-pressure at a suitable strength, such that a pressure field stimulation suitable in its frequency and amplitude leads to sexual arousal of the man, in the best case up to the male orgasm.

In order to be able to build up a alternating pressure field suitable for sexual stimulation (in the following also simply called a pressure field) with sufficient strength, an applicator with an opening is provided, as explained in what follows, so as to apply a alternating pressure field generated by a pressure field generation device directly to the skin of the penis. The applicator is adapted to the anatomy of the male member and is designed in particular to be placed over the frenulum 24 and the coronal sulcus 25, and also in particular for the accommodation of the frenulum 24. By the provision of a sealing device, the alternating pressure field required for stimulation can be built up to a sufficient extent by sealing a pressure chamber of the applicator from the environment.

The stimulation device is configured such that the stimulation does not cause the mucous membranes to dry out, which would happen, for example, as a result of a constant exchange of air with the environment. In addition, the device is configured for hygienic use, that is to say, cavities that are difficult to access and therefore difficult to clean, in which, for example, body fluid can collect, such as in valves, are avoided. In addition, the temperature of the relatively small volume of air trapped in the pressure chamber of the applicator can quickly adjust to the body temperature, ensuring comfortable use. In addition, the stimulation device is simple in design and therefore easy to use, such that distraction of the user during use, and the effort required for use, are minimised.

As a suitable sexual stimulation of the glans 4 of the male member, at best until orgasm, a comparatively high alternating frequency between 5 Hz to 250 Hz and a pressure difference of 20 mbar to 800 mbar about the ambient pressure of approx. 1 bar, preferably symmetrically about the ambient pressure, is particularly advantageous. Such an alternating pressure field consisting of an alternation of under- and over-pressures, with an alternating frequency of between 5 Hz and 250 Hz, and pressure differences of 20 mbar to 800 mbar, can be generated by means of a pressure field generation device, which is shown schematically in FIGS. 2 to 9. Various embodiments of applicators are shown in FIGS. 10 to 21. It is to be understood that the various embodiments or aspects of the various embodiments can be combined in any way.

Figure 2:
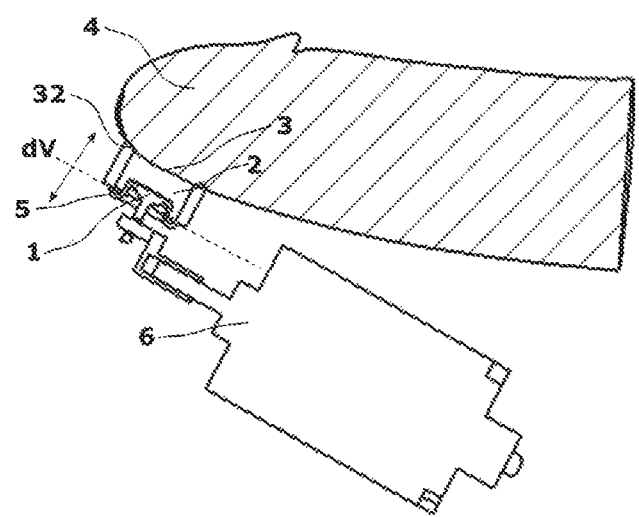
FIG. 2: shows an embodiment of a stimulation device.

FIG. 2 shows a first embodiment of a stimulation device with a pressure field generation device 1. The pressure field generation device 1 has at least one wall 5 or membrane, which consists of an elastic material, for example silicone or rubber, wherein this flexible wall 5 is deflected by means of a drive 6 so as to bring about a positive and negative volume change dV in the pressure field generation device 1 for generating the pressure field, in particular an alternating pressure field of under-pressure and over-pressure phases. A pressure chamber 2 is provided, in which the alternating pressure field generated by deflection of the wall 5 is established. The flexible wall 5 serves in particular only to generate the alternating pressure field in the pressure chamber 2 and is spaced apart from the opening 3, that is to say, it does not contact the penis during operation (that is to say, in particular in any deflected position). The pressure chamber 2 can have a constant cross-section in the flow direction, such that the pressure chamber is essentially of cylindrical design.

The pressure chamber 2 has an opening 3, which is configured in such a way that the pressure chamber 2, when placed on a region of the penis to be stimulated, such as the glans 4, or in particular the frenulum 24, is sealed or approximately sealed from the environment, that is to say, from regions outside the pressure chamber, such that the alternating pressure field can be established. A sealing device 32 is provided for this purpose, which is configured to seal against both over- and under-pressures relative to the ambient pressure. It surrounds the opening 3 and can be placed on the glans 4 in a sealing manner, in particular in such a way that the frenulum 24 is at least partially accommodated in the opening 3. The area of the opening 3 is equal to the cross-sectional area of the pressure chamber 2, and stimulation of the frenulum 24 can have a particularly strong effect in terms of sexual arousal.

Approximately tight fitting over the male glans 4 means, in particular, that an at least largely closed flow system is formed by means of the pressure field generation device 1. Media flows are generated in the flow system, in particular pneumatic flows, that is to say, air flows, which are directed alternately in time towards the male glans 4 (over-pressure) and away from the male glans 4 (under-pressure). It is to be understood that this is equally possible for any other desired region of the penis to be stimulated. In this closed flow system, a removal of body fluid from the pressure field generation device 1 is largely avoided.

Figure 3:
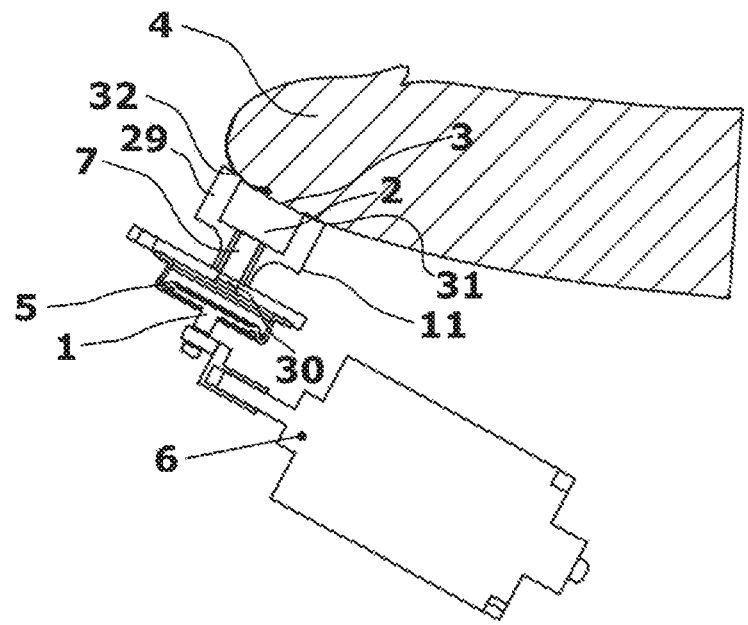
FIG. 3: shows another embodiment of a stimulation device.

FIG. 3 shows an example of a stimulation device in which the pressure field generation device 1 is connected to an applicator 11. The applicator 11 has an applicator body 29, in which the pressure chamber 2 is formed. The applicator 11 also has a port 30, which is connected to the pressure chamber 2 via a fluid channel 7, so as to transmit an alternating pressure field generated by the pressure field generation device 1 to the penis through the opening 3. The port 30 is opposite the opening 3 with respect to a longitudinal axis of the pressure chamber 2. The flexible membrane 5 is located on a side of the port 30 opposite the pressure chamber 2, outside the pressure chamber 2, and is spaced apart from the pressure chamber 2, in particular by the fluid channel 7. In the contact region 31 a sealing device 32, for example a sealing lip or a bead, is formed around the opening 3, so as to seal the pressure chamber 2 from the environment.

Figure 4:
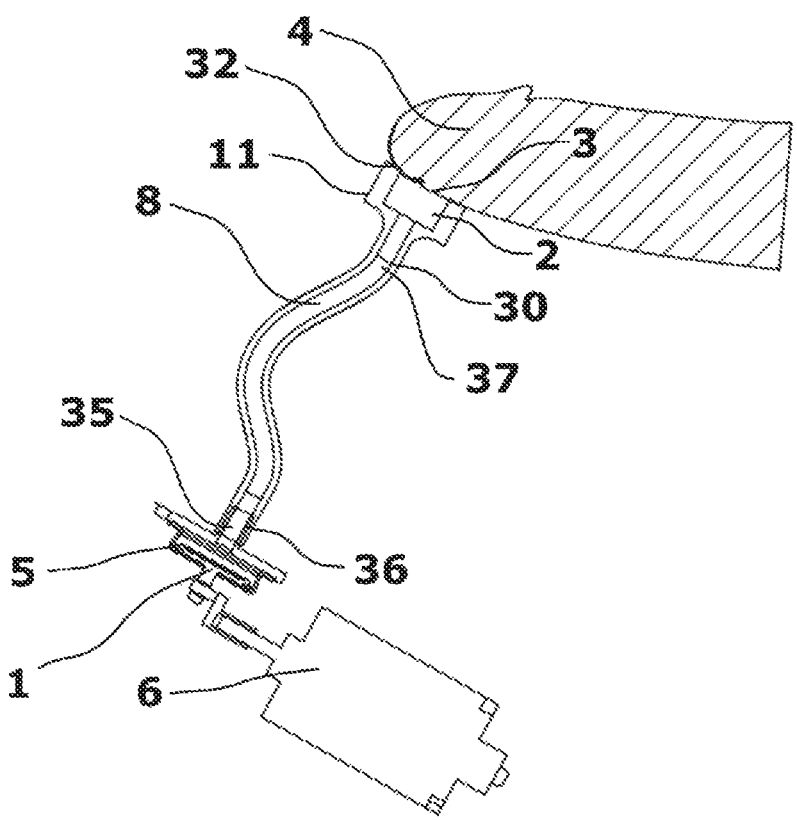
FIG. 4: shows yet another embodiment of a stimulation device.

FIG. 4 shows an embodiment in which the applicator 11 is connected to the pressure field generation device 1 via a connector 8 in the form of a tube, so as to transmit the alternating pressure field generated by the pressure field generation device 1 to the applicator 11, and apply it to the penis through the opening 3. In particular, a first port 36 of the connector 8 is connected to a pneumatic outlet 35 of the pressure field generation device 1, while a second port 37 of the connector 8 is connected to the port 30 of the applicator 11. This can be done, for example, via plug connectors, as described in more detail below. The connector 8 can be configured in sections, or in a completely flexible manner.

The configuration of the stimulation device with a tube as a connector 8 can serve for easy use of the stimulation device, as the user only has to hold the applicator 11 in his hand. If necessary, this can also be possible without a tube if the shape of the stimulation device is suitably configured, possibly with a short connecting piece (see, for example, FIG. 17). If an appropriate retaining device is provided at the same time, as described in more detail below, "hands-free" use can also be possible, in particular, since the pressure field generation device 1 can be placed, for example, next to, or on, the user.

A change in the cross-section of the pressure chamber 2, or of a pressure or flow system, which in addition to the pressure chamber 2 can also include the fluid channel 7, the connector 8, and/or other cavities exposed to the alternating pressure field, can affect the flow velocity of the medium (in particular air), that is to say, a cross-sectional constriction means a flow acceleration and a cross-sectional expansion correspondingly means a flow deceleration.

Since the pressure chamber 2 is placed on the penis in an almost sealed manner and thus an at least largely closed flow system is formed, there is virtually no exchange of air with the environment, which is why the removal of body fluid from the pressure field generation device is avoided, and the stimulation does not lead to the mucous membranes drying out. The temperature of the volume of air enclosed in the closed system quickly adjusts to the body temperature, by virtue of the relatively small volume. Furthermore, the stimulation device can be used without valves, which facilitates hygienic use.

Also with regard to hygienic use, a contact region defined by an accommodation region 31, or an accommodation chamber 34 of the applicator 11, is preferably open in the region of the tip of the glans 4. Thus, when using the stimulation device in accordance with the invention, in particular by virtue of the compact shape of the applicator 11, which is preferably configured to stimulate the frenulum 24, and thus has only to seal a small portion of the penis from the environment, the ejaculate can be discharged during orgasm. Cleaning is thus simplified. This provides a stimulation device that is improved in terms of hygiene, in particular compared to conventional closed stimulation devices.

Figure 5:
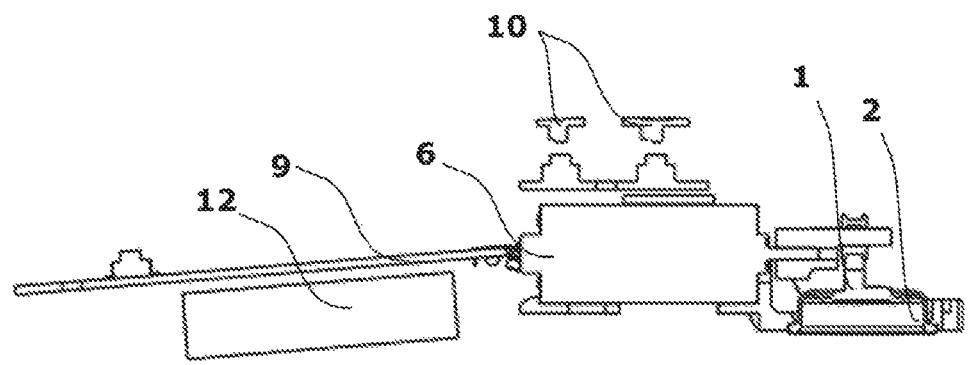
FIG. 5: shows an embodiment of a pressure field generation device.
Figure 6:
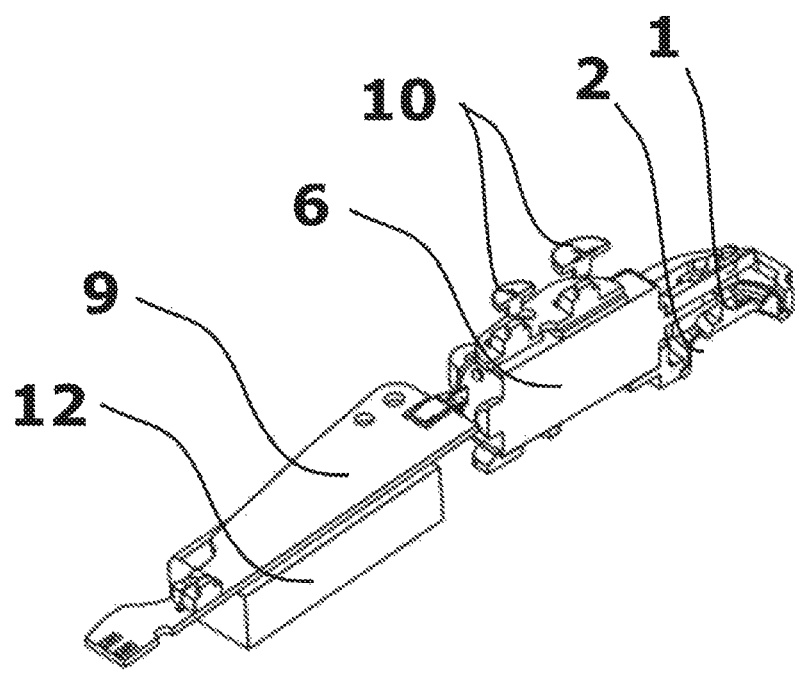
FIG. 6: shows the pressure field generation device from FIG. 5 in a perspective view.

As shown in FIGS. 5 and 6, the stimulation device has, in addition to the pressure field generation device 1, a control device 9, which can control a drive unit 6, and in which the modulation of the pressure field can be pre-stored. The control device 9 has at least one operating element 10, wherein the respective modulation of the pressure field can be changed by means of the operating element 10. In addition, the stimulation device has a housing (not shown), which can comprise the control device 9, the drive unit 6, the pressure field generation device 1 and an internal battery 12, wherein the stimulation device is preferably designed as a portable hand-held device. The control unit 9 makes it possible to set a stimulation pattern from the stimulation patterns of the control unit 9 by means of an operating element 10, wherein the drive unit 6 is controlled in accordance with the set stimulation pattern.

The drive unit 6, coupled to the flexible wall 5 of the pressure field generation device 1, can, for example, consist of a rotating electric motor 13 with a mechanical transmission. The mechanical transformation of the rotation of the electric motor 13 into a translational movement of the flexible wall 5 of the pressure field generation device 1 can take place, for example, by means of an eccentric 14, as shown schematically in FIG. 7.

Figure 7:
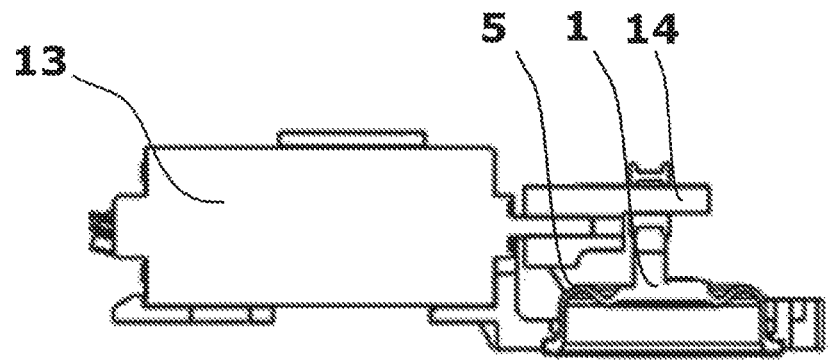
FIG. 7: shows a drive unit of the pressure field generation device.

FIG. 7 shows schematically the drive unit 6 in the form of a rotating electric motor with mechanical transformation and coupling to the flexible wall 5 of the pressure field generation device. By means of the control current supplied by the rotating electric motor 13, for example in the form of direct current, the rotational speed of the electric motor 13 and thus ultimately the frequency of the flexible wall 5 is varied and controlled. The flexible wall 5 can have a bead, which mechanically follows the strokes of the flexible wall 5, as far as possible without mechanical stress. The stroke of the flexible wall 5 is determined by the defined eccentric travel. The fixed piston stroke means a fixed reduction and increase of the chamber volume dV, and thus a corresponding fixed pressure increase or pressure reduction, that is to say, an approximately fixed amplitude of the alternating over- and under-pressure.

Figure 8:
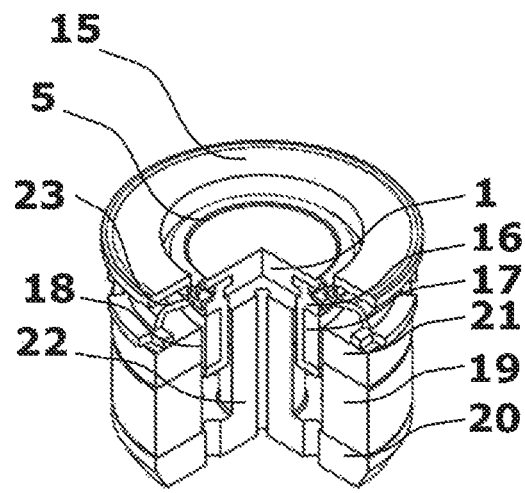
FIG. 8: shows an electric drive of a pressure field generation device.
Figure 9:
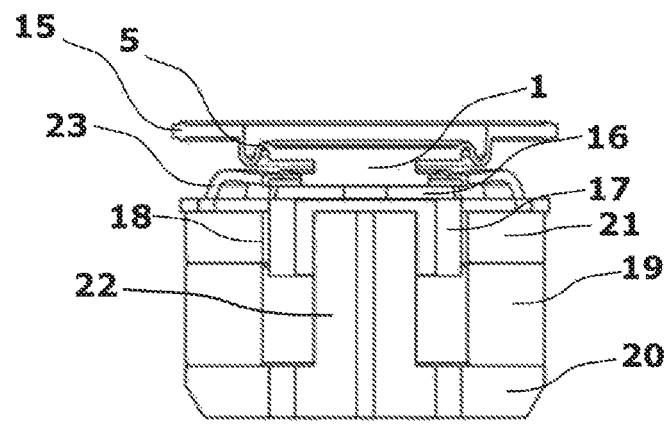
FIG. 9: shows another view of the electric drive from FIG. 8,
FIG. 10: shows an embodiment of an applicator in various views.

Alternatively, the drive unit 6 coupled to the flexible wall 5 of the pressure field generation device 1 can consist of a linear electric motor 15, as shown in FIGS. 8 and 9. In the electromagnetic transducer shown in FIGS. 8 and 9, the flexible wall 5 connected to a carrier 16 is moved back and forth by at least one moving coil or plunger coil 17 attached to it, in accordance with the coil supply, by means of the control current in the air gap 18.

The flexible wall 5 of the pressure field generation device 1 is attached to a carrier 16. The flexible wall 5 can have a bead, which mechanically follows the strokes of the flexible wall 5, as far as possible without mechanical stresses. A moving coil 17 is wound around the carrier 16, which coil is fed by the control current from a control unit during operation. The moving coil 17 consists of electrical conductors of a material that is as electrically conductive as possible (preferably copper), which conductors are insulated from each other and from the carrier 16 with an electrically insulating lacquer. The magnetic field is generated by at least one permanent magnet 19, preferably in ring form.

The magnetic flux, for example, is led by a rear pole plate 20 (preferably in cylindrical form) via the upper pole plate 21 (preferably in ring form) across the preferably ring-form air gap to the cylindrical pole core 22. The rear pole plate 20 and the upper pole plate 21 are made of magnetically highly permeable material (preferably a soft magnetic material alloy), as is the pole core 22. Alternatively, a cylindrical permanent magnet can be used instead of the pole core 22, and accordingly a ring pole can be used instead of the permanent magnet 19.

The carrier 16 with the moving coil 17 is structurally centred and guided in the air gap 18 by at least one mounting or suspension 23 (preferably made of plastic, textile fabric, or paper) to prevent wobbling movements of the moving coil 17. The mounting or suspension 23 is attached to a frame.

To move the flexible wall 5 the moving coil 17 is fed with an alternating control current from a control unit. The moving coil 17 is moved up or down by the Lorentz force, depending on the current direction, that is to say, the current polarity in the magnetic field of the air gap 18. The stroke of the deflection of the moving coil 17 is determined by the amplitude of the control current. The frequency of the alternating current corresponds to the frequency of the moving coil movement, and thus to the frequency of the piston or membrane movement. The frequency and the stroke of the moving coil 17, and thus the movement of the flexible wall 5, can thus be controlled independently of each other relatively easily by means of the current frequency and current amplitude. By virtue of the direct transmission, an extended frequency range is possible with this principle from below 1 Hz up to several hundred Hz. A direct current from a battery or accumulator is converted into an alternating current signal.

Essential for the establishment of the desired alternating pressure field, in particular with the cited under- and over-pressures in the order of magnitude of pressure differences of 20 mbar to 800 mbar, is the sealing of the pressure chamber 2 from the environment, in other words the application of the contact region 31 with the sealing device 32 resting on the penis, in particular on the glans 4, and the formation of an at least largely closed flow system. For this purpose, the contact region 31 and in particular the sealing device 32 is suitably configured with regard to shape and material, as described below with the aid of preferred embodiments. Furthermore, a contact pressure sufficient for the build-up of the above-mentioned under- and over-pressures can be applied to the sealing device 32, as also described below with the aid of preferred embodiments. Needless to say, relevant characteristics, in particular with regard to the transmission of the alternating pressure field to the penis, are common to all embodiments and are not described with regard to each embodiment, simply to avoid repetition.

Figure 10:
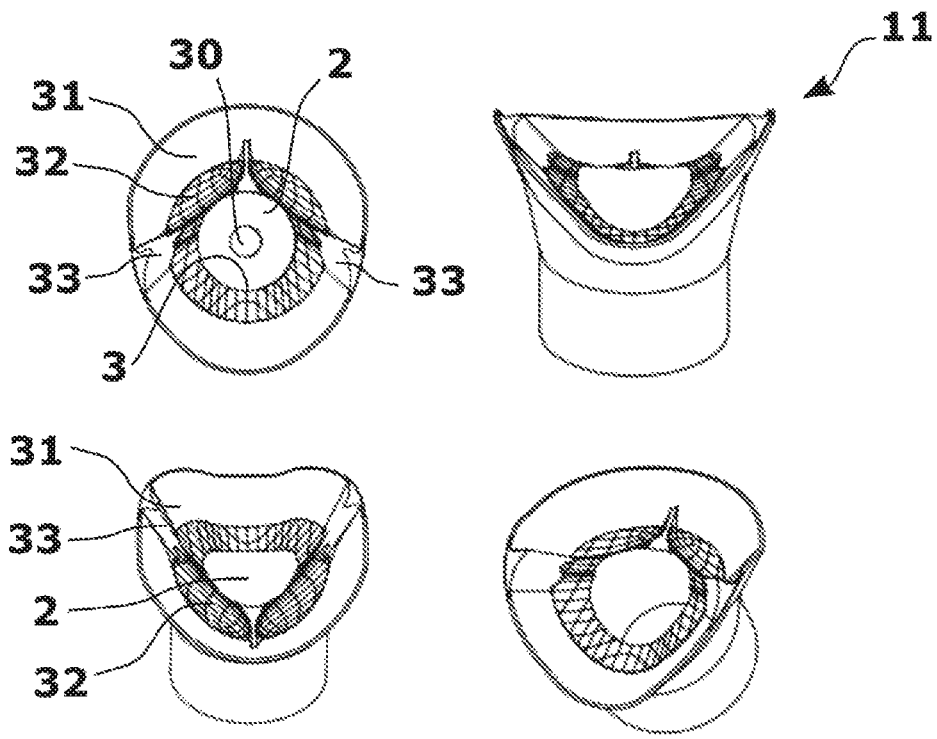

FIG. 10 shows an embodiment of an applicator 11, which, in addition to the sealing device 32, has anatomically shaped projections 33 in the contact region 31. Furthermore, the contact region 31 is configured so as to have a surface shape that supports the seal. A sealing device 32 is provided, which surrounds the opening 3 of the pressure chamber 2 of the applicator 11. The sealing device 32 is designed as a rounded pliable bead around the opening 3, which can adapt to the shape of the penis when the applicator 11 is applied to the penis.

In addition, the projections 33 are provided, which essentially follow the profile of the coronal sulcus 25. This can support the sealing effect of the sealing device 32, such that the projections 33 can also be regarded as part of the sealing device 32. By virtue of their anatomical shape, the projections 33 can facilitate the correct positioning of the applicator 11 on the penis, in particular in such a way that the frenulum 24 is at least partially accommodated in the pressure chamber 2.

The material of the sealing device 32 is preferably soft, for example a soft silicone or rubber. The projections 33 can be made of the same material or of a different material, for example one that is harder or softer. The opening 3 of the pressure chamber 2 is designed in such a way that it can at least partially accommodate the frenulum 24, such that the alternating pressure field in the pressure chamber 2 can act directly on the frenulum 24.

Figure 11:
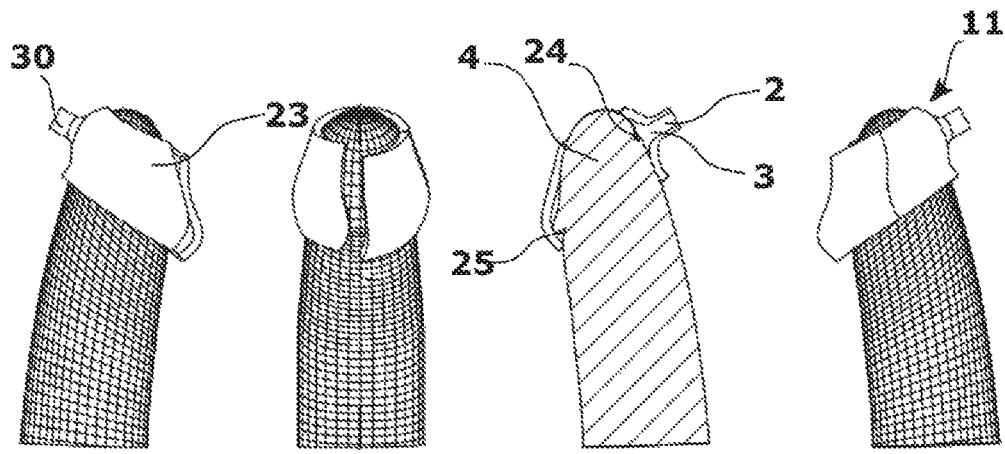
FIG. 11: shows another embodiment of an applicator, applied onto a penis, in various views.

In accordance with one embodiment, the contact pressure required for a seal can be applied by the user himself by means of hand pressure. FIG. 11 schematically shows such an applicator 11, applied to a penis, in which the pressure chamber 2 is sealed against the glans 4 by the pressure applied by hand pressure. A retaining device or gripping device in the form of wing-like extensions 23 is formed, which the user can position in a largely flexible manner on the penis or the glans 4. In this manner, the sealing device is pressed against the penis. The opening 3 is designed to receive the frenulum 24 and parts, or all, of the corona glandis 25. In this embodiment, the pressure chamber 2 expands towards the opening 3, as can be seen in the cross-sectional view in FIG. 11.

Figure 12:
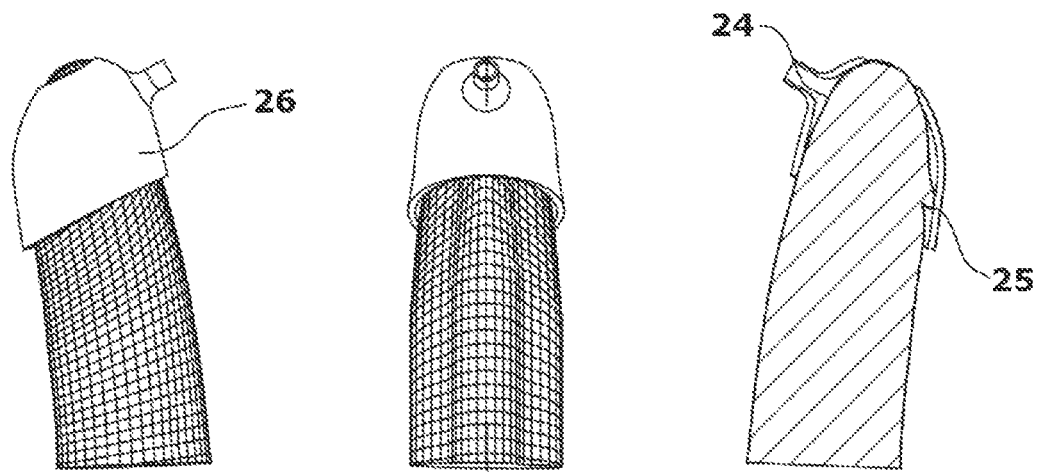
FIG. 12: shows another embodiment of an applicator, applied onto a penis, in various views.

In accordance with another embodiment, as shown in FIG. 12, the necessary contact pressure can be achieved, for example, by an essentially ring-form retaining device 26, wherein the internal material stresses occurring during elastic deformation of the ring 26 act on the penis and on the sealing device. It is advantageous if the retaining device 26 is open in the region of the tip of the glans 4. However, a cap-like structure closed at the tip is also conceivable, which structure is elastically deformable like the ring-form retaining device 26, and thus holds the applicator 11 on the glans 4. In the embodiment shown in FIG. 12, the opening 3 of the pressure chamber 2 is sealed against the glans 4 after extension and placement of the ring-form retaining device 26, wherein the opening 3 accommodates the frenulum 24 and parts, or all, of the corona glandis 25.

Figure 13:
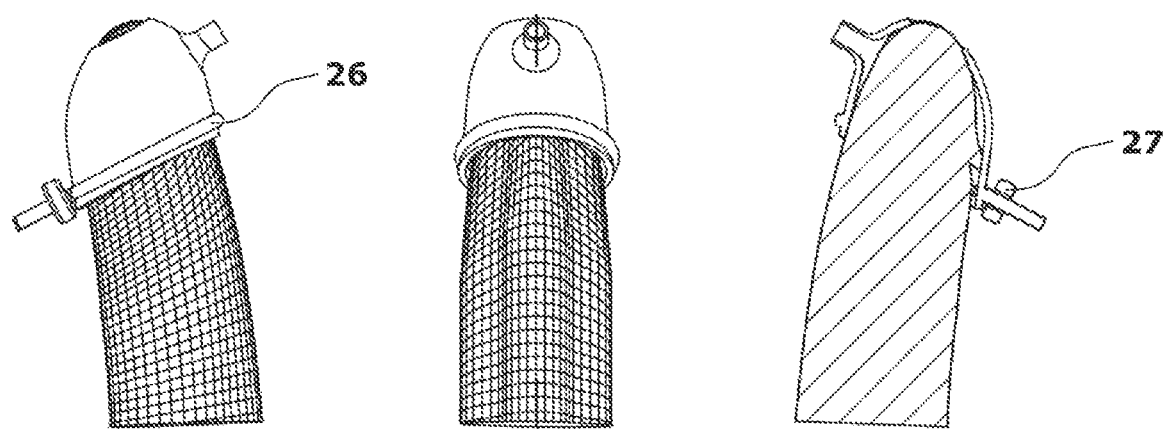
FIG. 13: shows another embodiment of an applicator, applied onto a penis, in various views.

The ring-form and elastically deformable retaining device 26 shown in FIG. 12 can be reinforced by a strap with a tightening mechanism 27, as shown in FIG. 13. Here the sealing is achieved by means of the internal stresses of the material when elastically deformed and additionally by a force applied against the glans 4 of the male member by means of a strap.

Figure 14:
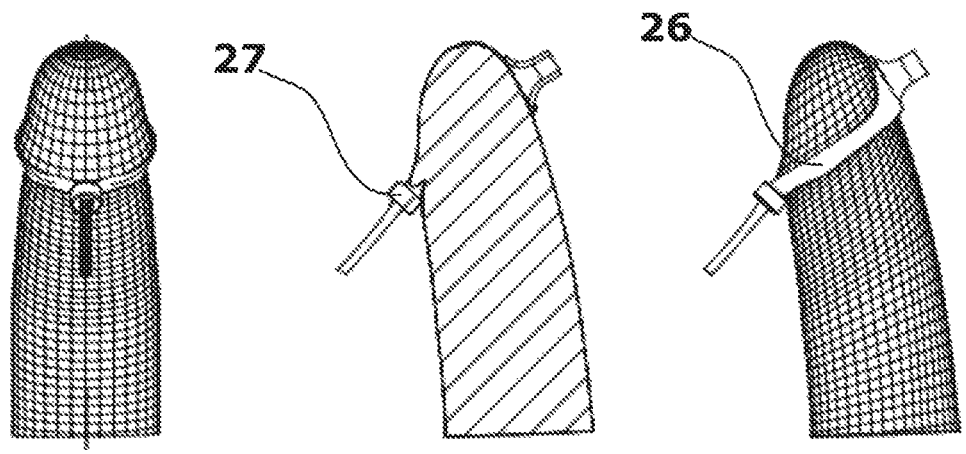
FIG. 14: shows another embodiment of an applicator, applied onto a penis, in various views.

Alternatively, in accordance with another embodiment, the necessary contact pressure can be applied solely by a strap- or band-form retaining device 26 with a fixing or tightening mechanism 27, as shown in FIG. 14. The strap is particularly easy to fix, and therefore position, on the corona glandis 25. In addition, this retaining device 26 of the applicator 11 can be adapted particularly easily to different diameters of the male member in the region of the glans 4.

Figure 15:
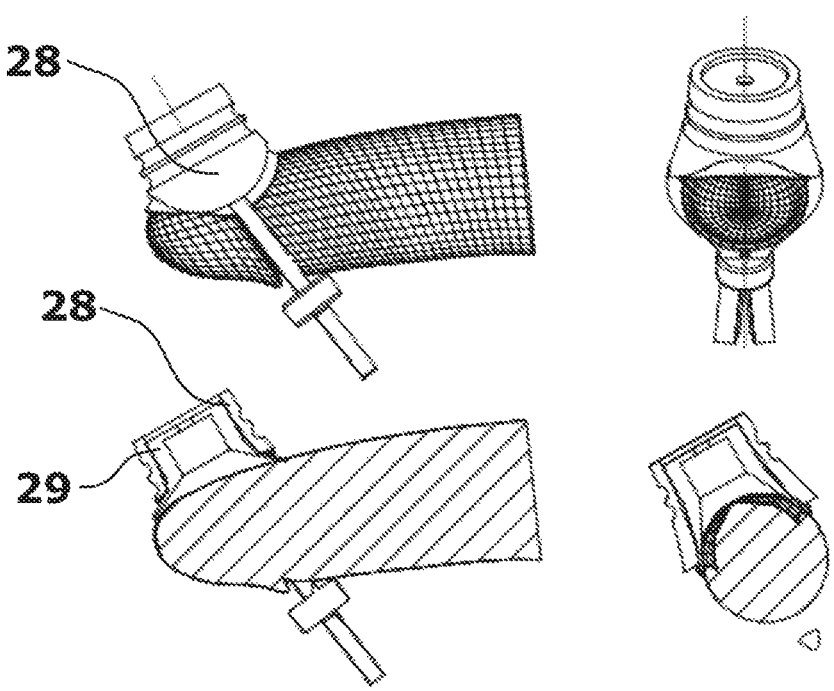
FIG. 15: shows another embodiment of an applicator, applied onto a penis, in various views.

In another variant of the applicator, as shown in FIG. 15, the retaining device can be designed separately from the applicator body 29. This means that, by selecting a suitable retaining device, the seal can be improved even with different member diameters, that is to say, glans diameters, and its use can be simplified with regard to the putting on and taking off of the stimulation device and its cleaning. This multi-piece design is shown in FIG. 15 using the strap sealing system as an example. A retaining body 28 with a strap, separate from the applicator body 29, is arranged above the applicator body 29, such that the necessary contact pressure can be applied to the sealing device. The two parts can be of the same material, or of different materials.

The embodiments shown in FIGS. 10 to 15 are, in particular, designed for stationary or non-moving use of the stimulation device or applicator 11. In other words, the applicator 11 can, in particular as regards its shape, the contact region 31 and the sealing device 32, be configured in such a way that it is placed on the penis and, if necessary, secured by a retaining device, but without being moved. Here, for stimulation, the alternating pressure field is applied via the opening 3, in particular onto the frenulum 24.

However, it may be desired that the applicator can be moved over the shaft of the penis, the coronal sulcus 25, the corona glandis and the glans 4. At the same time, however, when applying a contact pressure or a compressive force, a sealing connection should be created so as to achieve stimulation, as in the other embodiments, by applying the alternating pressure field via the opening 3. The applicator in accordance with the embodiments of FIGS. 16 to 21 is configured in such a way that it can be moved along the shaft of the penis, in particular by releasing, or at least relaxing, the contact pressure. However, movement can also be possible while maintaining the contact pressure.

For this purpose, the sealing device 32 is preferably configured in such a way that, on the one hand, it adapts itself to the surface of the coronal sulcus and other regions on the penis, by virtue of the applied contact pressure and bead-like lips around the opening 3 of the pressure chamber 2, and applies a seal, and, on the other hand, can be moved when the contact pressure is released or relaxed, or when a contact pressure is applied or maintained. Advantageously, the contact region 31 extends around the entire periphery of the penis and defines a peripherally closed accommodation chamber 34 (FIGS. 16 to 20), but can also be open at the periphery (FIG. 21). The retaining devices described in what follows are also suitable for fixing the applicator to the penis, but can be relaxed or released so as to allow the applicator to be moved along the penis shaft. During a movement the alternating pressure field can still be generated or switched off. The sealing device can form a sliding seal, such that at least a partial sealing effect up to the same, or almost the same, sealing effect as in stationary operation can be achieved even when moving, and the alternating pressure field can be built up in the pressure chamber 2 and applied to the penis through the opening 3.

Figure 16:
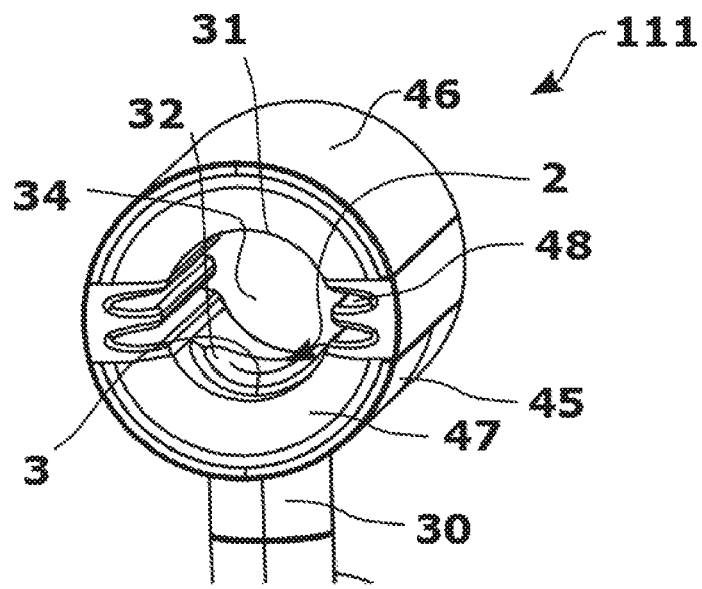
FIG. 16: shows another embodiment of an applicator.

In FIG. 16 an example of an applicator 111 is shown, which has a peripherally (or circumferentially) continuous contact region 31 and thus a peripherally closed accommodation chamber 34, into which the penis can be introduced. In a similar manner to the embodiments described above, the applicator 111 has a port 30, via which an alternating pressure field generated by a pressure field generation device 1 can be applied to a pressure chamber 2 of the applicator 111 and finally, via the opening 3, to a portion of the penis to be stimulated, such as the frenulum. To seal the pressure chamber 2 from the environment, a sealing device 32 is formed around the opening 3 in the contact region 31.

The applicator 111 has a rigid shell, which comprises a first part 45 with the port 30, and an opposing second part 46. A soft insert 47, made, for example, of silicone, is arranged in the shell, which has the contact region 31, and rests against the penis during use. The parts 45, 46 of the shell are spaced apart when the applicator 111 is in the unloaded state, and can be moved together by hand. This compresses the soft insert 47 such that the contact pressure of the sealing device 32 on the penis is increased. The compression of the insert 47 can be facilitated by providing one or a plurality of indentations 48. By the application of sufficient contact pressure, the pressure chamber 2 is sealed from the environment and an alternating pressure field can be applied to the penis.

The sealing device 32 is also designed in such a way, for example so as to be soft and rounded, that the applicator 111 can also be moved along the penis shaft. It is possible that sufficient contact pressure and thus sufficient sealing of the pressure chamber 2 for the application of an alternating pressure field can be achieved even during movement. However, if the contact pressure is too low, the establishment of the alternating pressure field can be impaired. In use, a combined stimulation can thus be achieved, wherein the applicator 111, for example, can be moved such that, in addition to the friction generated, it rests on the penis in a sealing position, at least in phases, such that in these positions a pneumatic stimulation is generated by means of the pressure field. The sealing position can also be in motion, depending on the location of the penis. For example, a moving seal can be easier in the penile shaft region than in the glans region. However, a user may wish to switch off the pressure field generation device 1 and use the applicator for manual stimulation only. If necessary, structures such as nubs, ribs, and similar (not shown) can be provided on the surface of the insert 47, that is to say, in the contact region 31, so as to increase the stimulation by friction in this case.

Figure 17:
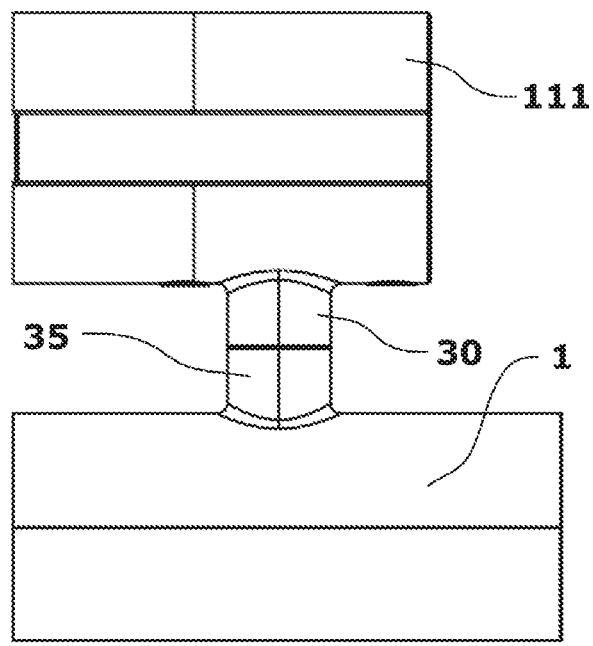
FIG. 17: shows a stimulation device with the applicator from FIG. 16.

FIG. 17 shows the applicator 111 connected with a pressure field generation device 1. The hand of a user is indicated, which holds the applicator 111 or presses it together as required. Here the pneumatic output port 35 of the pressure field generation device 1 is directly connected to the port 30 of the applicator 111. It is to be understood that a connector 8, for example a tube, can be placed between the pressure field generation device 1 and the applicator 111 for connection, as described above.

Figure 18:
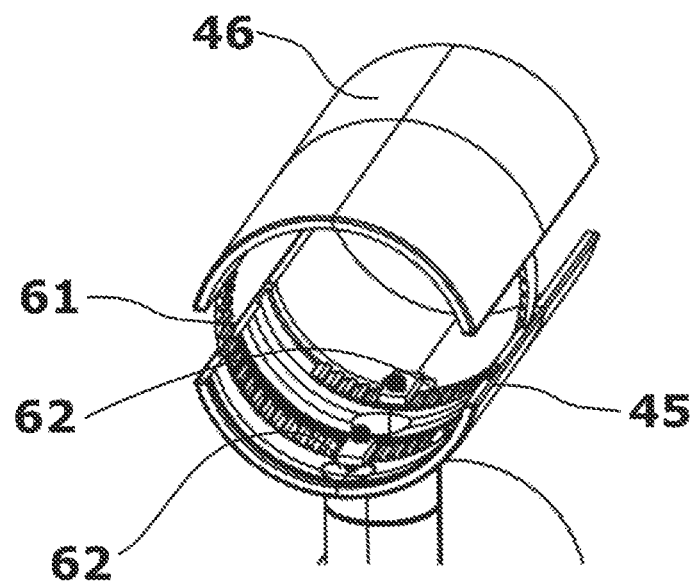
FIG. 18: shows a retaining device of an applicator.

FIG. 18 shows one part of an embodiment of an applicator 111, which is similar to the one shown in FIG. 16, here too an increase in contact pressure is achieved by manually pressing the two parts 45, 46 of the shell together. However, a fixing device is provided which fixes the shell in a desired position, and maintains the contact pressure even after the applicator is released. In particular, a latching mechanism 61 is provided, whereby the clamping force resulting from compression is maintained, even if no external force is applied to the shell. This is achieved by the interlocking of corresponding surface profiles, such as teeth. A mechanism 62 is provided, which releases the latching mechanism 61 by suitable displacement of the surface profiles relative to one another.

Figure 19:
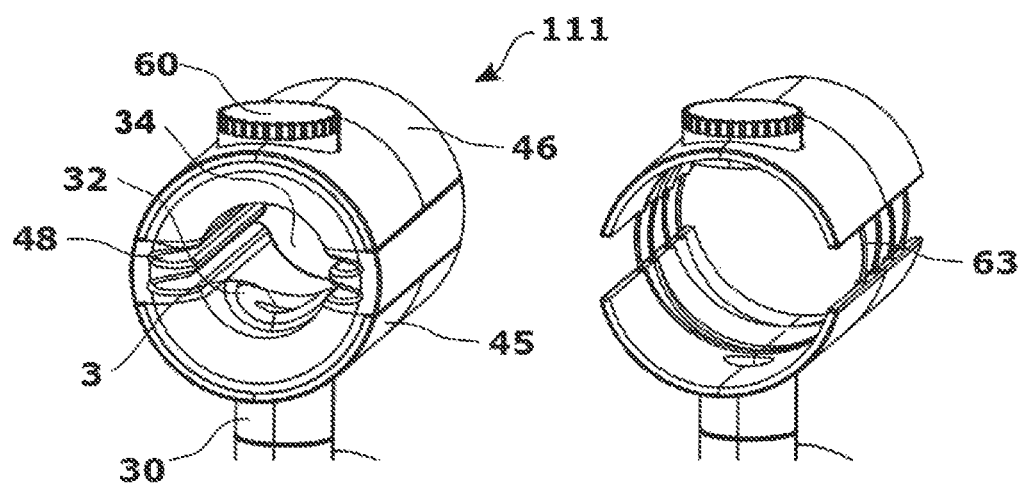
FIG. 19: shows another embodiment of an applicator and its retaining device.

In the embodiment of an applicator 111 shown in FIG. 19, which is otherwise similar to that shown in FIG. 16, an increase in the contact pressure is achieved by means of a clamping device. By actuating the clamping device, for example by means of a rotary knob 60, pull cords 63 are tensioned. The pull cords 63 can be located in a guide channel (not shown) in both parts 45 and 46 of the shell. A turning movement of the knob 60 tensions the pull cords 63, moving the parts 45 and 46 towards one another and increasing the contact pressure on the penis. The clamping device preferably has a fixing device (not shown) with a latching function that prevents the applied clamping force from being released unintentionally. Advantageously a mechanism for releasing the latching function is provided.

Figure 20:
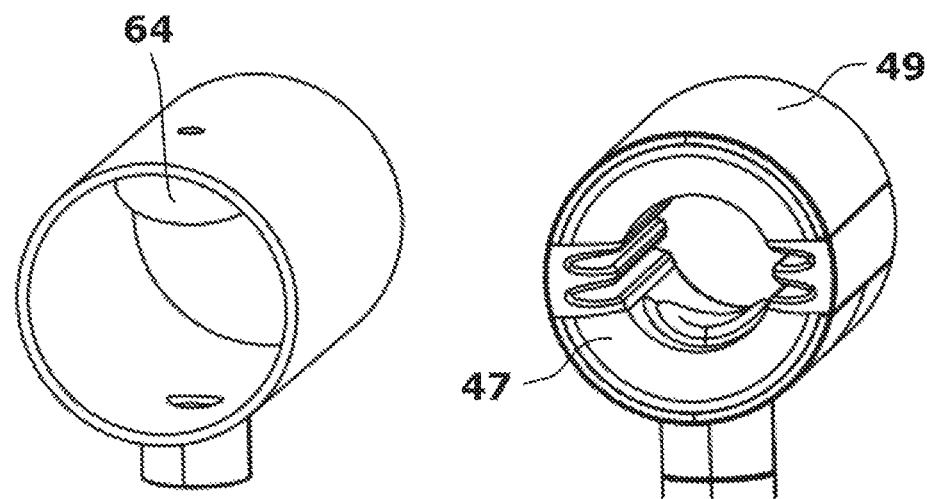
FIG. 20: shows another embodiment of an applicator.
Figure 21:
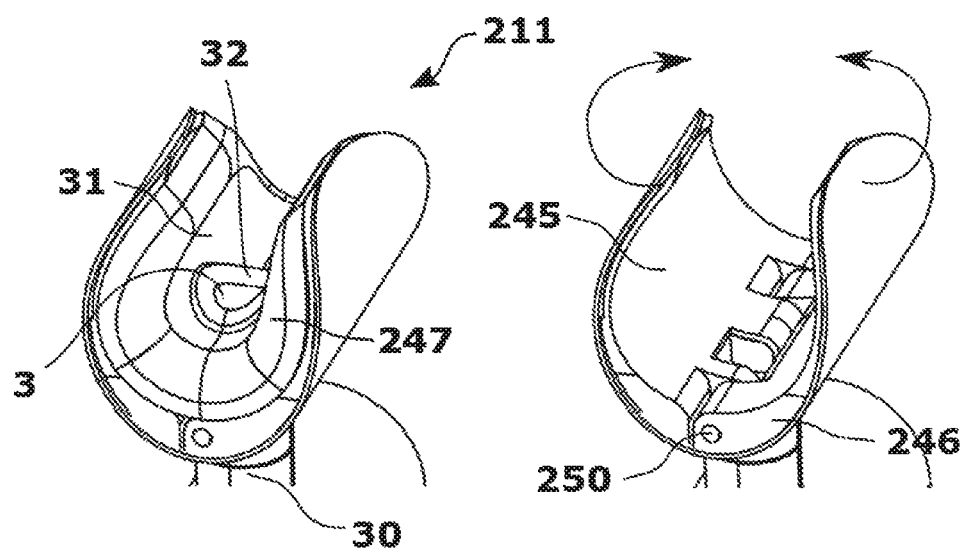
FIG. 21: shows another embodiment of an applicator.

In the embodiment of an applicator 111 shown in FIG. 20, which is otherwise similar to the one shown in FIG. 16, an increase in the contact pressure is achieved by means of at least one air cushion 64, which is arranged between the shell 49, which here is designed in one piece, and the insert 47. By inflating the air cushion 64, in particular with air, the diameter of the cavity 34 of the applicator 111 can be reduced at least in some sections, and the contact pressure on the penis can be increased. A one-way valve (not shown) can be provided so as to release the air from the air cushion 64 and thus reduce the contact pressure again.

In accordance with the embodiment shown in FIG. 21, the applicator 211 has a wing-like shell with a first part 245 and a second part 246, which are connected to each other via a hinge 250 such that they can move, in particular can swivel together. The contact region 31 does not completely enclose the penis. A torsion spring (not shown) is preferably provided, which forces a movement of the parts 245 and 246 of the shell away from one another into an open position. A fixing device (not shown) with a latching function can be provided, which fixes the applicator 211 in a constricted position caused by a user by the application of a force. A mechanism for releasing the latched position can also be provided.

Figure 22:
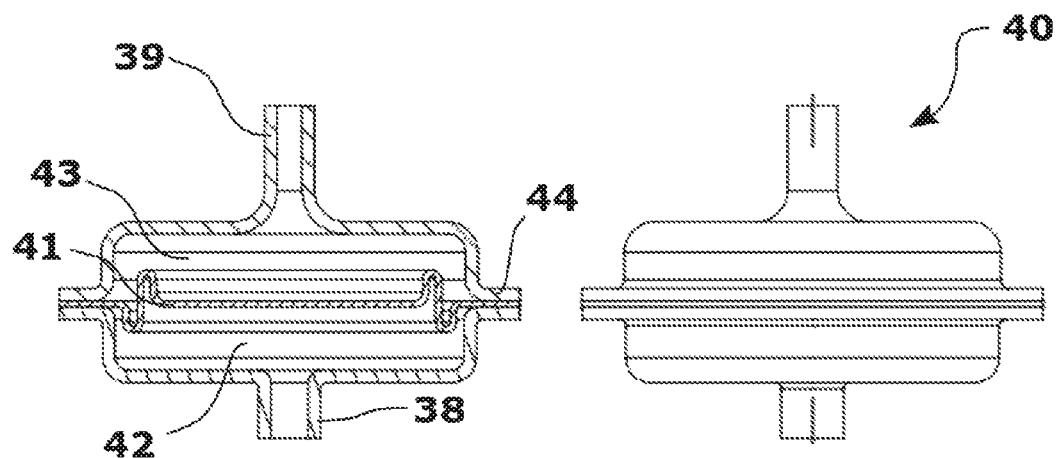
FIG. 22: shows a coupling device for a connector between an applicator and a pressure field generation device.

FIG. 22 shows a coupling device 40, which serves in particular as a backflow valve. For hygienic reasons, when using a connector 8 in the form of a tube, care must be taken to ensure that no secretions are sucked into the tube as a result of capillary action, and are not deposited in the latter. The coupling device 40 is placed between the tube 8 and the applicator 11, or between two sections 38, 39 of the tube 8, wherein the section 38 leads to the pressure field generation device 1, while the section 39 leads to the applicator 11. It is advantageous to position the coupling device 40 close to the applicator 11 such that the section 39 of the tube 8 to be cleaned, which points towards the applicator 11, is as short as possible.

The coupling device 40 has a membrane 41, which divides a cavity of the coupling device 40 into two chambers 42, 43, such that no fluid can pass from the chamber 43 into the chamber 42, that is to say, in the direction from the applicator 11 to the pressure field generation device 1. A pressure change, in particular due to the alternating pressure field generated by the pressure field generation device 1, causes a deflection of the membrane 41, such that the alternating pressure field is transmitted despite prevention of a fluid flow. In particular for cleaning, the coupling device 40 can be separated by releasing a fastening mechanism 44, and the section 39 of the tube 8 can be cleaned with the applicator 11. It is not necessary to clean the section 38 of the tube 8, as no fluid can enter the section 38 by virtue of the fluid-impermeable membrane 41.

Figure 23:
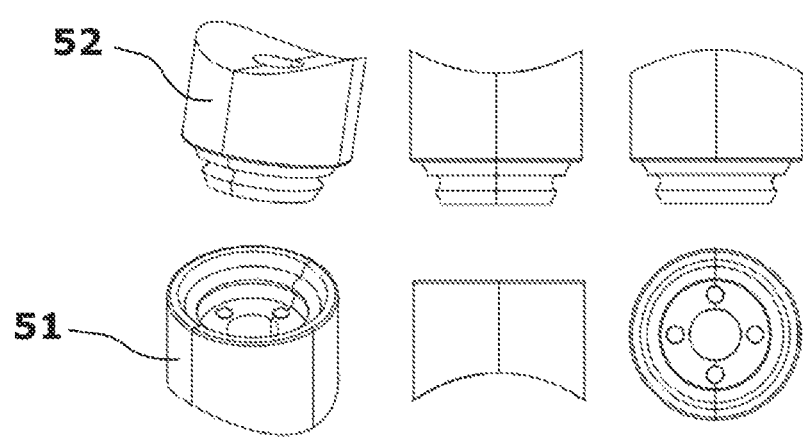
FIG. 23: shows an embodiment of a plug connector.

FIG. 23 shows an example of the design of a connection mechanism in the form of a fluid-tight plug connector. By means of the connecting mechanism, any applicator 11, for example one of the applicators described above, can be connected directly to a pressure field generation device 1. Alternatively, the connection mechanism can be used to connect a connector 8, for example a tube, to an applicator 11, or a pressure field generation device 1, or both. A plug connector allows an easy assembly of a stimulation device. The connector shown in FIG. 23 has a first part 51 with a socket, into which an extension of a second part 52 can be introduced. For sealing, an O-ring can, for example, be provided in at least one of the connector parts, or in both.

It is to be understood that any aspects of the preferred embodiments described above can be combined in an appropriate manner. In particular, the preferred embodiments are only exemplary. For example, various aspects of the applicator, such as the sealing device, pressure chamber, opening, contact region, accommodation chamber, and retaining device, can be combined in any manner so as to create an applicator in accordance with the invention for applying an alternating pressure field to a region of a penis to be stimulated, in particular the glans, preferably the frenulum. Regardless of the specific configuration of the applicator, the applicator can also be directly connected, or can be connected, to a pressure field generation device, or a connector such as a tube can be provided for this purpose. Provision can also be made for one or a plurality of the applicators described, or even a plurality of applicators of the same type, to be provided in a set, together with a pressure field generation device and, if required, a suitable connector.

The invention claimed is:

1. A stimulation device for a penis, the stimulation device comprising:
   an applicator including:
      an applicator body to receive at least a portion of the penis therein, the applicator body having first end and a second end opposite the first end, the applicator body defining an opening extending through the first end and the second end;
      a pressure chamber formed in the applicator body; and
      an applicator port fluidly coupled to the pressure chamber via a portion of the applicator different than the opening, the applicator port in fluid communication with the opening;
   a pressure field generation device to generate a pneumatic alternating pressure field of under-pressures and over-pressures relative to an ambient pressure, the pressure field generation device including a pneumatic output port to output the pneumatic alternating pressure field, the applicator coupled to the pneumatic output port, the pneumatic alternating pressure field to be transmitted from the pressure field generation device to the pressure chamber of the applicator via the applicator port; and
   a coupling device disposed between the applicator port and the pneumatic output port, the coupling device to transmit the pneumatic alternating pressure field and to prevent a fluid flow from the applicator to the pressure field generation device, the coupling device including a flexible and fluid-impermeable membrane.

2. The stimulation device of claim 1, wherein the applicator body includes a contact region, the contact region to at least partially contact the penis when the applicator body is placed on the penis, the applicator further including a sealing device to seal the pressure chamber from an ambient environment when the applicator body is placed on the penis.

3. The stimulation device of claim 2, wherein the sealing device is formed in the contact region of the applicator body, the sealing device to contact at least a portion of the penis when the applicator body is placed on the penis to seal the pressure chamber from the ambient environment.

4. The stimulation device of claim 2, wherein the sealing device is formed peripherally around the pressure chamber.

5. The stimulation device of claim 2, further including at least one anatomically shaped projection disposed in the contact region of the applicator body.

6. The stimulation device of claim 5, wherein at least a portion of the at least one anatomically shaped projection is configured to follow a profile of a coronal sulcus of the penis.

7. The stimulation device of claim 2, wherein the pressure chamber is to at least partially accommodate a frenulum of the penis when the applicator body is placed on the penis.

8. The stimulation device of claim 2, wherein the contact region of the applicator body defines an accommodation chamber, the accommodation chamber adjacent to the contact region of the applicator body and to at least partially accommodate the penis, the contact region to contact at least a portion of a periphery of the penis.

9. The stimulation device of claim 2, further including a retaining device to hold the applicator body when the applicator body is placed on the penis.

10. The stimulation device of claim 9, wherein the retaining device extends from the applicator body, the retaining device to contact at least a portion of a periphery of the penis.

11. The stimulation device of claim 9, wherein the retaining device includes a fixing device to fix the retaining device in a first position.

12. The stimulation device of claim 9, wherein the retaining device is to increase a contact pressure of the sealing device against the penis when the applicator body is placed on the penis.

13. The stimulation device of claim 1, further including a fluid channel defined in the applicator body, the applicator port and the pressure chamber fluidly coupled via the fluid channel.

14. The stimulation device of claim 1, further including a connector, the connector including:
   a first port to be fluidly coupled to the pneumatic output port of the pressure field generation device; and
   a second port to be fluidly coupled to the applicator port, the pneumatic alternating pressure field to be transmitted from the pressure field generation device to the pressure chamber of the applicator via the connector.

15. The stimulation device of claim 14, wherein the connector includes the coupling device disposed between the first port and the second port of the connector.

16. The stimulation device of claim 1, wherein the applicator is removably coupled to the pneumatic output port.

17. The stimulation device of claim 16, wherein the applicator is a first applicator and further including a second applicator, the second applicator different from the first applicator, the second applicator removably couplable to the pneumatic output port.

18. The stimulation device of claim 1, wherein the applicator port is removably coupled to the pneumatic output port.

19. The stimulation device of claim 1, wherein the pressure field generation device includes a rotating electric motor.

20. The stimulation device of claim 1, wherein the pressure field generation device includes a linear electric motor.

21. The stimulation device of claim 1, wherein the pressure field generation device is to generate the pneumatic alternating pressure field with a frequency between 5 Hz and 250 Hz.

\* \* \* \* \*